(12) United States Patent
Leung et al.

(10) Patent No.: US 9,580,499 B2
(45) Date of Patent: Feb. 28, 2017

(54) VEGFR2/ANG2 COMPOUNDS

(71) Applicant: Eli Lilly and Company, Indianapolis, IN (US)

(72) Inventors: Donmienne Doen Mun Leung, San Diego, CA (US); Ling Liu, Carmel, IN (US); Jirong Lu, Carmel, IN (US); Ying Tang, San Diego, CA (US); Jianghuai Xu, San Diego, CA (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 14/709,511

(22) Filed: May 12, 2015

(65) Prior Publication Data
US 2015/0329626 A1   Nov. 19, 2015

Related U.S. Application Data

(60) Provisional application No. 62/000,227, filed on May 19, 2014.

(51) Int. Cl.
| | |
|---|---|
| *A61K 39/00* | (2006.01) |
| *C07K 16/00* | (2006.01) |
| *C07K 16/22* | (2006.01) |
| *C07K 16/40* | (2006.01) |
| *C07K 16/28* | (2006.01) |

(52) U.S. Cl.
CPC ........... *C07K 16/22* (2013.01); *C07K 16/2863* (2013.01); *C07K 16/40* (2013.01); *A61K 2039/505* (2013.01); *C07K 2317/14* (2013.01); *C07K 2317/31* (2013.01); *C07K 2317/33* (2013.01); *C07K 2317/56* (2013.01); *C07K 2317/622* (2013.01); *C07K 2317/64* (2013.01); *C07K 2317/76* (2013.01); *C07K 2317/92* (2013.01); *C07K 2317/94* (2013.01); *C07K 2319/00* (2013.01)

(58) Field of Classification Search
None
See application file for complete search history.

(56) References Cited

FOREIGN PATENT DOCUMENTS

| EP | 2433968 A1 | 3/2012 |
|---|---|---|
| WO | WO 2010/040508 A1 | 4/2010 |
| WO | WO 2011/117339 A2 | 9/2011 |
| WO | WO 2012/009705 A1 | 1/2012 |

OTHER PUBLICATIONS

Jendreyko, N. et al., "Intradiabodies, bispecific, tetravalent antibodies for the simultaneous functional knockout of two cell surface receptors", Journal of Biological Chemistry; 278(48), pp. 47812-47819 (Nov. 28, 2003).
Brown, J., et al., "A Human Monoclonal Anti-ANG2 Antibody Leads to Broad Antitumor Activity in Combination with VEGF Inhibitors and Chemotherapy Agents in Preclinical Models," Mol Cancer Ther; 9(1), pp. 145-156 (2010).
Gerald, D., et al., "Angiopoietin-2: An Attractive Target for Improved Antiangiogenic Tumor Therapy," Cancer Research; 57(1), pp. 1649-1657 (2013).
Daly, C., et al., "Angiopoietin-2 Functions as a Tie2 Agonist in Tumor Models, Where It Limits the Effects of VEGF Inhibition," Cancer Research; 73(1), pp. 108-118 (2013).
Demarest, S., et al., "Emerging antibody combinations in oncology," mAbs; 3(4), pp. 338-351 (Jul./Aug. 2011).
Eroglu, Z., et al., "Targeting angiopoietin-2 signaling in cancer therapy," Expert Opinion; 22, pp. 813-825 (2013).
Huang, H., et al., "Targeting the ANGPT—TIE2 pathway in malignancy," Natural Reviews Cancer; 10, pp. 575-585 (2010).
Leow, C., et al., "MEDI3617, a human anti-Angiopoietin 2 monoclonal antibody, inhibits angiogenesis and tumor growth in human tumor xenograft models," Int.J. Oncol.; 40(5), pp. 1321-1330 (May 10, 2012).
Zhu, A., et al., "A Phase II and Biomarker Study of Ramucirumab, a Human Monoclonal Antibody Targeting the VEGF Receptor-2, as First-Line Monotherapy in Patients with Advanced Hepatocellular Cancer," Clinical Cancer Research; 19, pp. 6614-6623 (Dec. 1, 2013).
Doppalapudi., et al., "Chemical generation of bispecific antibodies" Proceedings of the National Academy of Sciences, 107(52), pp. 22611-22616 (Dec. 28, 2010).

*Primary Examiner* — Hong Sang
(74) *Attorney, Agent, or Firm* — Robert Brian Johnson

(57) ABSTRACT

The present invention relates to compounds that bind to human vascular endothelial growth factor receptor-2 (VEGFR2) and human angiopoietin-2 (Ang2), and may be useful for treating cancer, especially solid tumors driven by VEGFR2 and Ang2, including gastric, hepatocellular carcinoma, ovarian, colorectal, non-small cell lung, biliary tract, and breast cancers.

10 Claims, No Drawings

VEGFR2/ANG2 COMPOUNDS

SEQUENCE LISTING

This application incorporates by reference the Sequence Listing submitted in Computer Readable form as file 2015.05.12.092816_Sequence Listing.txt on May 12, 2015 (102,882 bytes).

The present invention relates to the field of medicine. More particularly, the present invention relates to compounds that bind to human vascular endothelial growth factor receptor-2 (VEGFR2) and human angiopoietin-2 (Ang2), and may be useful for treating cancer, especially solid tumors driven by VEGFR2 and Ang2, including gastric, hepatocellular carcinoma, ovarian, colorectal, non-small cell lung, biliary tract, and breast cancers.

A hallmark of cancer is persistent new blood vessel formation, called angiogenesis. The vascular endothelial growth factor (VEGF) pathway is an important signaling cascade in the regulation of angiogenesis; human VEGFR2 is a key receptor in the VEGF pathway. Ramucirumab (IMC-1121B) is an IgG1 antibody that targets human VEGFR2, and has been shown to have an antitumor effect in certain clinical studies (see, for example, Zhu et al., Clin Cancer Res (2013) 19:6614).

Angiopoietin-1 (Ang1) and Ang2 are members of another key pathway that regulate angiogenesis; Ang1 and Ang2 are secreted factors that bind to the endothelial cell-specific receptor tyrosine kinase Tie2. Ang1 is constitutively secreted by pericytes and stabilizes blood vessel integrity via the Tie2 receptor. Ang2 is released from endothelial cells only in response to stimulus (e.g. wound healing, tumor growth) and facilitates blood vessel sprouting and inhibits pericyte-endothelial cell interaction via Tie2 signaling. An antibody against human Ang2, when dosed in combination with the VEGF blocker aflibercept, has been shown to inhibit tumor growth and to decrease tumor vascularity in mouse xenograft tumor models (Daly et al., Cancer Res (2013) 73(1):108). Multiple investigational Ang2 antibodies are currently in clinical trials.

Inhibition of both the VEGF and Ang/Tie2 pathways of angiogenesis has been proposed for the potential to improve the outcome against cancer (see, for example, Daly et al., Cancer Res (2013) 73:108). Currently, co-administration of a VEGFR2 antibody and Ang-2 antibody would require either injections or infusions of two separate products or administration of a co-formulation of an antibody mixture. Separate administration would permit flexibility of dose amount and timing, but would be a potential issue for patient compliance and inconvenience due to increased infusion time. A co-formulation might provide some flexibility of dosage amounts, but can be challenging to find formulation conditions that permit chemical and physical stability of both antibodies due to different molecular characteristics of the two different antibodies. Furthermore, co-administration or co-formulation involves the additive costs of two drug therapies.

WO2012/009705 disclosed complexes containing one or more modular recognition domains (MRDs) attached to scaffolds that include antibodies. Ang2 was listed as contemplated for the MRD portion of the complex, and a VEGFR2 antibody was specified as an antibody which MRDs could be attached. A MRD against Ang2 attached to a VEGFR2 antibody was not exemplified. Brown et al. (Mol Cancer Ther (2010) 9(1):145) disclosed a human monoclonal Ang2 antibody, 3.19.3. In a SW620 xenograft study, 3.19.3 was dosed in combination with DC101, a monoclonal antibody that binds murine VEGFR2.

When generating compounds (Compound A and B) that contain a VEGFR2 antibody portion containing the light chain variable region (LCVR) and heavy chain variable region (HCVR) of the IMC-1121B antibody in an IgG1 or IgG4 backbone, fused to a single chain Fv (scFv) portion binding human Ang2, expression and stability problems were observed by Applicant as part of the present invention. Specifically, chemical instability and unacceptable product quality in recombinantly expressed materials due to free light chain mis-pairing were surprisingly observed. As observed by Applicant as part of the present invention, compound engineering to improve chemical instability and product quality in the materials obtained from cell culture unexpectedly led to certain compounds with increased product heterogeneity due to Mab-diabody formation.

There remains a need to provide compounds that inhibit two angiogenesis pathways by binding and neutralizing both human VEGFR2 and human Ang2. In particular, there remains a need to provide compounds that inhibit two angiogenesis pathways by binding and neutralizing both human VEGFR2 and human Ang2, and without compromising significant Ang2 in vitro binding activity due to the use of an Ang2 scFv, and without compromising significant in vitro cell-based assay activity due to the combination of the VEGFR2 antibody and Ang2 scFv into one compound. There also remains a need to provide compounds that inhibit two angiogenesis pathways by binding and neutralizing both human VEGFR2 and human Ang2, and avoid at least one of the above listed stability and product heterogeneity problems.

Accordingly, an embodiment of the present invention provides a compound, comprising an antibody fused by two linkers to two single chain fragment variable (scFv) polypeptides, wherein:

a) the antibody comprises two identical heavy chains (HCs) and two identical light chains (LCs), wherein each HC comprises a heavy chain variable region (HCVR) whose amino acid sequence is given in SEQ ID NO: 1, SEQ ID NO: 2, SEQ ID NO: 3, or SEQ ID NO: 4, and wherein each LC comprises a light chain variable region (LVCR) whose amino acid sequence is given in SEQ ID NO: 13, SEQ ID NO: 14, or SEQ ID NO: 15, b) the two scFv polypeptides are identical and each comprise an HCVR operably linked to an LCVR, wherein each HCVR has the amino acid sequence given in SEQ ID NO: 21, or SEQ ID NO: 22, and wherein each LCVR has the amino acid sequence given in SEQ ID NO: 23, or SEQ ID NO: 24, and c) the two linkers are identical glycine-rich linkers that each operably link the carboxy-terminus of one HC of the antibody to the amino-terminus of one of the scFv polypeptides.

In a further embodiment, the present invention provides a compound comprising an antibody fused by two linkers to two scFv polypeptides, wherein the two scFv polypeptides each comprise the carboxy-terminus of the LCVR of one scFv polypeptide operably linked to the amino-terminus of the HCVR of one scFv polypeptide.

In an embodiment, the present invention provides a compound comprising an antibody fused by two linkers to two scFv polypeptides, wherein each HCVR of the antibody has the amino acid sequence given in SEQ ID NO: 1, each LCVR of the antibody has the amino acid sequence given in SEQ ID NO: 13, the HCVR of each of the scFv polypeptides has the amino acid sequence given in SEQ ID NO: 21, and the LCVR of each of the scFv polypeptides has the amino acid sequence given in SEQ ID NO: 23

In an embodiment, the present invention provides a compound comprising an antibody fused by two linkers to two scFv polypeptides, wherein each HCVR of the antibody has the amino acid sequence given in SEQ ID NO: 2, each LCVR of the antibody has the amino acid sequence given in SEQ ID NO: 14, the HCVR of each of the scFv polypeptides has the amino acid sequence given in SEQ ID NO: 21, and the LCVR of each of the scFv polypeptides has the amino acid sequence given in SEQ ID NO: 23.

In an embodiment, the present invention provides a compound comprising an antibody fused by two linkers to two scFv polypeptides, wherein each HCVR of the antibody has the amino acid sequence given in SEQ ID NO: 3, each LCVR of the antibody has the amino acid sequence given in SEQ ID NO: 15, the HCVR of each of the scFv polypeptides has the amino acid sequence given in SEQ ID NO: 21, and the LCVR of each of the scFv polypeptides has the amino acid sequence given in SEQ ID NO: 23.

In an embodiment, the present invention provides a compound comprising an antibody fused by two linkers to two scFv polypeptides, wherein each HCVR of the antibody has the amino acid sequence given in SEQ ID NO: 4, each LCVR of the antibody has the amino acid sequence given in SEQ ID NO: 13, the HCVR of each of the scFv polypeptides has the amino acid sequence given in SEQ ID NO: 22, and the LCVR of each of the scFv polypeptides has the amino acid sequence given in SEQ ID NO: 24.

In an embodiment, the present invention provides a compound comprising an antibody fused by two linkers to two scFv polypeptides, wherein the antibody comprises two heavy chains (HCs) and two light chains (LCs), wherein each HC has the amino acid sequence given in one of SEQ ID NO: 5, SEQ ID NO: 6, SEQ ID NO: 7, or SEQ ID NO: 8, and each LC has the amino acid sequence given in one of SEQ ID NO: 16, SEQ ID NO: 17, or SEQ ID NO: 18.

In an embodiment, the present invention provides a compound comprising an antibody fused by two linkers to two scFv polypeptides, wherein each HC of the antibody has the amino acid sequence given in SEQ ID NO: 5, and each LC of the antibody has the amino acid sequence given in SEQ ID NO: 16.

In an embodiment, the present invention provides a compound comprising an antibody fused by two linkers to two scFv polypeptides, wherein each HC of the antibody has the amino acid sequence given in SEQ ID NO: 6, and each LC of the antibody has the amino acid sequence given in SEQ ID NO: 17.

In an embodiment, the present invention provides a compound comprising an antibody fused by two linkers to two scFv polypeptides, wherein each HC of the antibody has the amino acid sequence given in SEQ ID NO: 7, and each LC of the antibody has the amino acid sequence given in SEQ ID NO: 18.

In an embodiment, the present invention provides a compound comprising an antibody fused by two linkers to two scFv polypeptides, wherein each HC of the antibody has the amino acid sequence given in SEQ ID NO: 8, and each LC of the antibody has the amino acid sequence given in SEQ ID NO: 16.

In an embodiment, the present invention provides a compound comprising an antibody fused by two linkers to two scFv polypeptides, wherein each scFv polypeptide has the identical amino acid sequence given in one of SEQ ID NO: 19 or SEQ ID NO: 20. In an embodiment, the present invention provides a compound comprising an antibody fused by two linkers to two scFv polypeptides, wherein each scFv polypeptide has the amino acid sequence given in SEQ ID NO: 19. In an embodiment, the present invention provides a compound comprising an antibody fused by two linkers to two scFv polypeptides, wherein each scFv polypeptide has the amino acid sequence given in SEQ ID NO: 20.

In an embodiment, the present invention provides a compound comprising two first polypeptides and two second polypeptides wherein each of the first polypeptides has the amino acid sequence of SEQ ID NO: 9, SEQ ID NO: 10, SEQ ID NO: 11, or SEQ ID NO: 12, and each of the second polypeptides has the amino acid sequence of SEQ ID NO: 16, SEQ ID NO: 17, or SEQ ID NO: 18. As shown in Table 1, the two first polypeptides comprise the HC of the antibody, the linker, and the scFv polypeptide; the two second polypeptides comprise the LC of the antibody.

In an embodiment, the present invention provides a compound comprising two first polypeptides and two second polypeptides wherein each of the first polypeptides has the amino acid sequence of SEQ ID NO: 9, and each of the second polypeptides has the amino acid sequence of SEQ ID NO: 16. In an embodiment, the present invention provides a compound comprising two first polypeptides and two second polypeptides wherein each of the first polypeptides has the amino acid sequence of SEQ ID NO: 10, and each of the second polypeptides has the amino acid sequence of SEQ ID NO: 17. In an embodiment, the present invention provides a compound comprising two first polypeptides and two second polypeptides wherein each of the first polypeptides has the amino acid sequence of SEQ ID NO: 11, and each of the second polypeptides has the amino acid sequence of SEQ ID NO: 18. In an embodiment, the present invention provides a compound comprising two first polypeptides and two second polypeptides wherein each of the first polypeptides has the amino acid sequence of SEQ ID NO: 12, and each of the second polypeptides has the amino acid sequence of SEQ ID NO: 16.

In an embodiment, the present invention further provides a compound comprising two first polypeptides and two second polypeptides wherein each of the first polypeptides forms an inter-chain disulfide bond with each of the second polypeptides, and the first polypeptide forms two inter-chain disulfide bonds with the other first polypeptide, and each of the first polypeptides forms an intra-chain disulfide bond.

In an embodiment, the present invention provides a compound that binds human VEGFR2 and human Ang2 comprising an antibody that binds human VEGFR2 (SEQ ID NO: 32) fused by two linkers to two scFv polypeptides that bind human Ang2 (SEQ ID NO: 33), wherein:
a) the antibody comprises two identical heavy chains (HCs) and two identical light chains (LCs), wherein each HC comprises a heavy chain variable region (HCVR) whose amino acid sequence is given in SEQ ID NO: 1, SEQ ID NO: 2, SEQ ID NO: 3, or SEQ ID NO: 4, and wherein each LC comprises a light chain variable region (LVCR) whose amino acid sequence is given in SEQ ID NO: 13, SEQ ID NO: 14, or SEQ ID NO: 15,
b) the two scFv polypeptides are identical and each comprise an HCVR operably linked to an LCVR, wherein each HCVR has the amino acid sequence given in SEQ ID NO: 21, or SEQ ID NO: 22, and wherein each LCVR has the amino acid sequence given in SEQ ID NO: 23, or SEQ ID NO: 24, and c) the two linkers are identical glycine-rich linkers that each operably link the carboxy-terminus of one HC of the antibody to the amino-terminus of one of the scFv polypeptides.

In a further embodiment, the present invention provides a compound that binds human VEGFR2 and human Ang2 comprising an antibody that binds human VEGFR2 (SEQ ID NO: 32) fused by two linkers to two scFv polypeptides that bind human Ang2 (SEQ ID NO: 33), wherein the carboxy-terminus of the LCVR of each scFv polypeptide is operably linked to the amino-terminus of the HCVR.

In an embodiment, the present invention provides a compound that binds human VEGFR2 and human Ang2 comprising an antibody that binds human VEGFR2 (SEQ ID NO: 32) fused by two linkers to two scFv polypeptides that bind human Ang2 (SEQ ID NO: 33), wherein each HCVR of the antibody has the amino acid sequence given in SEQ ID NO: 1, each LCVR of the antibody has the amino acid sequence given in SEQ ID NO: 13, the HCVR of each of the scFv polypeptides has the amino acid sequence given in SEQ ID NO: 21, and the LCVR of each of the scFv polypeptides has the amino acid sequence given in SEQ ID NO: 23

In an embodiment, the present invention provides a compound that binds human VEGFR2 and human Ang2 comprising an antibody that binds human VEGFR2 (SEQ ID NO: 32) fused by two linkers to two scFv polypeptides that bind human Ang2 (SEQ ID NO: 33), wherein each HCVR of the antibody has the amino acid sequence given in SEQ ID NO: 2, each LCVR of the antibody has the amino acid sequence given in SEQ ID NO: 14, the HCVR of each of the scFv polypeptides has the amino acid sequence given in SEQ ID NO: 21, and the LCVR of each of the scFv polypeptides has the amino acid sequence given in SEQ ID NO: 23.

In an embodiment, the present invention provides a compound that binds human VEGFR2 and human Ang2 comprising an antibody that binds human VEGFR2 (SEQ ID NO: 32) fused by two linkers to two scFv polypeptides that bind human Ang2 (SEQ ID NO: 33), wherein each HCVR of the antibody has the amino acid sequence given in SEQ ID NO: 3, each LCVR of the antibody has the amino acid sequence given in SEQ ID NO: 15, the HCVR of each of the scFv polypeptides has the amino acid sequence given in SEQ ID NO: 21, and the LCVR of each of the scFv polypeptides has the amino acid sequence given in SEQ ID NO: 23.

In an embodiment, the present invention provides a compound that binds human VEGFR2 and human Ang2 comprising an antibody that binds human VEGFR2 (SEQ ID NO: 32) fused by two linkers to two scFv polypeptides that bind human Ang2 (SEQ ID NO: 33), wherein each HCVR of the antibody has the amino acid sequence given in SEQ ID NO: 4, each LCVR of the antibody has the amino acid sequence given in SEQ ID NO: 13, the HCVR of each of the scFv polypeptides has the amino acid sequence given in SEQ ID NO: 22, and the LCVR of each of the scFv polypeptides has the amino acid sequence given in SEQ ID NO: 24.

In an embodiment, the present invention provides a compound that binds human VEGFR2 and human Ang2 comprising an antibody that binds human VEGFR2 (SEQ ID NO: 32) fused by two linkers to two scFv polypeptides that bind human Ang2 (SEQ ID NO: 33), wherein the antibody comprises two heavy chains (HCs) and two light chains (LCs), wherein each HC has the amino acid sequence given in one of SEQ ID NO: 5, SEQ ID NO: 6, SEQ ID NO: 7, or SEQ ID NO: 8, and each LC has the amino acid sequence given in one of SEQ ID NO: 16, SEQ ID NO: 17, or SEQ ID NO: 18.

In an embodiment, the present invention provides a compound that binds human VEGFR2 and human Ang2 comprising an antibody that binds human VEGFR2 (SEQ ID NO: 32) fused by two linkers to two scFv polypeptides that bind human Ang2 (SEQ ID NO: 33), wherein each HC of the antibody has the amino acid sequence given in SEQ ID NO: 5, and each LC of the antibody has the amino acid sequence given in SEQ ID NO: 16.

In an embodiment, the present invention provides a compound that binds human VEGFR2 and human Ang2 comprising an antibody that binds human VEGFR2 (SEQ ID NO: 32) fused by two linkers to two scFv polypeptides that bind human Ang2 (SEQ ID NO: 33), wherein each HC of the antibody has the amino acid sequence given in SEQ ID NO: 6, and each LC of the antibody has the amino acid sequence given in SEQ ID NO: 17.

In an embodiment, the present invention provides a compound that binds human VEGFR2 and human Ang2 comprising an antibody that binds human VEGFR2 (SEQ ID NO: 32) fused by two linkers to two scFv polypeptides that bind human Ang2 (SEQ ID NO: 33), wherein each HC of the antibody has the amino acid sequence given in SEQ ID NO: 7, and each LC of the antibody has the amino acid sequence given in SEQ ID NO: 18.

In an embodiment, the present invention provides a compound that binds human VEGFR2 and human Ang2 comprising an antibody that binds human VEGFR2 (SEQ ID NO: 32) fused by two linkers to two scFv polypeptides that bind human Ang2 (SEQ ID NO: 33), wherein each HC of the antibody has the amino acid sequence given in SEQ ID NO: 8, and each LC of the antibody has the amino acid sequence given in SEQ ID NO: 16.

In an embodiment, the present invention provides a compound that binds human VEGFR2 and human Ang2 comprising an antibody that binds human VEGFR2 (SEQ ID NO: 32) fused by two linkers to two scFv polypeptides that bind human Ang2 (SEQ ID NO: 33), wherein each scFv polypeptide has the identical amino acid sequence given in one of SEQ ID NO: 19 or SEQ ID NO: 20. In an embodiment, the present invention provides a compound that binds human VEGFR2 and human Ang2 comprising an antibody that binds human VEGFR2 (SEQ ID NO: 32) fused by two linkers to two scFv polypeptides that bind human Ang2 (SEQ ID NO: 33), wherein each scFv polypeptide has the amino acid sequence given in SEQ ID NO: 19. In an embodiment, the present invention provides a compound that binds human VEGFR2 and human Ang2 comprising an antibody that binds human VEGFR2 (SEQ ID NO: 32) fused by two linkers to two scFv polypeptides that bind human Ang2 (SEQ ID NO: 33), wherein each scFv polypeptide has the amino acid sequence given in SEQ ID NO: 20.

In an embodiment, the present invention provides a compound that binds human VEGFR2 (SEQ ID NO: 32) and human Ang2 (SEQ ID NO: 33) comprising two first polypeptides and two second polypeptides wherein each of the first polypeptides has the amino acid sequence of SEQ ID NO: 9, SEQ ID NO: 10, SEQ ID NO: 11, or SEQ ID NO: 12, and each of the second polypeptides has the amino acid sequence of SEQ ID NO: 16, SEQ ID NO: 17, or SEQ ID NO: 18. In an embodiment, the present invention provides a compound that binds human VEGFR2 (SEQ ID NO: 32) and human Ang2 (SEQ ID NO: 33) comprising two first polypeptides and two second polypeptides wherein each of the first polypeptides has the amino acid sequence of SEQ ID NO: 9, and each of the second polypeptides has the amino acid sequence of SEQ ID NO: 16. In an embodiment, the present invention provides a compound that binds human VEGFR2 (SEQ ID NO: 32) and human Ang2 (SEQ ID NO: 33) comprising two first polypeptides and two second polypeptides wherein each of the first polypeptides has the amino acid sequence of SEQ ID NO: 10, and each of the second polypeptides has the amino acid sequence of SEQ ID NO: 17. In an embodiment, the present invention provides a compound that binds human VEGFR2 (SEQ ID NO: 32) and human Ang2 (SEQ ID NO: 33) comprising two first polypeptides and two second polypeptides wherein each of the first polypeptides has the amino acid sequence of SEQ ID NO: 11, and each of the second polypeptides has the amino acid sequence of SEQ ID NO: 18. In an embodiment, the present invention provides a compound that binds human VEGFR2 (SEQ ID NO: 32) and human Ang2 (SEQ ID NO: 33) comprising two first polypeptides and two second polypeptides wherein each of the first polypeptides has the amino acid sequence of SEQ ID NO: 12, and each of the second polypeptides has the amino acid sequence of SEQ ID NO: 16.

In an embodiment, the present invention further provides a compound that binds human VEGFR2 (SEQ ID NO: 32) and human Ang2 (SEQ ID NO: 33) comprising two first polypeptides and two second polypeptides wherein each of the first polypeptides forms an inter-chain disulfide bond with each of the second polypeptides, and the first polypeptide forms two inter-chain disulfide bonds with the other first polypeptide, and each of the first polypeptides forms an intra-chain disulfide bond.

In a further embodiment, the present invention provides a compound of the present invention that has a dissociation equilibrium constant, $K_D$, of about 300 pM to about 1400 pM for human VEGFR2 and a $K_D$ of about 300 pM to about 800 pM for human Ang2. The compound of the present invention is further characterized by a $k_{on}$ rate to human VEGFR2 of about $0.1 \times 10^5$ $M^{-1}$ $sec^{-1}$ to about $0.5 \times 10^5$ $M^{-1}$ $sec^{-1}$ and a $k_{on}$ rate to human Ang2 of about $1 \times 10^5$ $M^{-1}$ $sec^{-1}$ to about $3 \times 10^5$ $M^{-1}$ $sec^{-1}$. The compound of the present invention is further characterized by a $k_{off}$ rate to human VEGFR2 of about $0.1 \times 10^{-4}$ $sec^{-1}$ to about $0.5 \times 10^{-4}$ $sec^{-1}$ and a $k_{off}$ rate to human Ang2 of about $0.8 \times 10^{-4}$ $sec^{-1}$ to about $1.2 \times 10^{-4}$ $sec^{-1}$. The $K_D$, $k_{on}$ and $k_{off}$ values are established by binding kinetics at 25° C. as described in "Binding kinetics, affinity, and selectivity" in the Assays section.

The compound of the present invention binds to human VEGFR2 and human Ang2 with high affinity. For the purposes of the present disclosure, the term "high affinity" refers to a $K_D$ of less than about 1500 pM for human VEGFR2 and of less than about 1000 pM for human Ang2. The $K_D$ values are established by binding kinetics at 25° C. as described in "Binding kinetics, affinity, and selectivity" in the Assays section.

In an embodiment, the present invention provides a mammalian cell comprising a DNA molecule comprising a polynucleotide sequence a encoding a polypeptide selected from the group consisting of a polypeptide consisting of SEQ ID NO: 9, SEQ ID NO: 10, SEQ ID NO: 11 and SEQ ID NO: 12 and a polynucleotide sequence encoding a polypeptide selected from the group consisting of a polypeptide consisting of SEQ ID NO: 16, SEQ ID NO: 17 and SEQ ID NO: 18, wherein the cell is capable of expressing a compound comprising a first polypeptide having an amino acid sequence selected from the group consisting of SEQ ID NO: 9, SEQ ID NO: 10, SEQ ID NO: 11 and SEQ ID NO: 12 and a second polypeptide having an amino acid sequence selected from the group consisting of SEQ ID NO: 16, SEQ ID NO: 17 and SEQ ID NO: 18.

In an embodiment, the present invention provides a mammalian cell comprising a DNA molecule comprising a polynucleotide sequence encoding a polypeptide having an amino acid sequence of SEQ ID NO: 9 and a polynucleotide sequence encoding a polypeptide having an amino acid sequence of SEQ ID NO: 16, wherein the cell is capable of expressing a compound comprising a first polypeptide having an amino acid sequence of SEQ ID NO: 9 and a second polypeptide having an amino acid sequence of SEQ ID NO: 16.

In an embodiment, the present invention provides a mammalian cell comprising a DNA molecule comprising a polynucleotide sequence encoding a polypeptide having an amino acid sequence of SEQ ID NO: 10 and a polynucleotide sequence encoding a polypeptide having an amino acid sequence of SEQ ID NO: 17, wherein the cell is capable of expressing a compound comprising a first polypeptide having an amino acid sequence of SEQ ID NO: 10 and a second polypeptide having an amino acid sequence of SEQ ID NO: 17.

In an embodiment, the present invention provides a mammalian cell comprising a DNA molecule comprising a polynucleotide sequence encoding a polypeptide having an amino acid sequence of SEQ ID NO: 11 and a polynucleotide sequence encoding a polypeptide having an amino acid sequence of SEQ ID NO: 18, wherein the cell is capable of expressing a compound comprising a first polypeptide having an amino acid sequence of SEQ ID NO: 11 and a second polypeptide having an amino acid sequence of SEQ ID NO: 18.

In an embodiment, the present invention provides a mammalian cell comprising a DNA molecule comprising a polynucleotide sequence encoding a polypeptide having an amino acid sequence of SEQ ID NO: 12 and a polynucleotide sequence encoding a polypeptide having an amino acid sequence of SEQ ID NO: 16, wherein the cell is capable of expressing a compound comprising a first polypeptide having an amino acid sequence of SEQ ID NO: 12 and a second polypeptide having an amino acid sequence of SEQ ID NO: 16.

In an embodiment, the present invention provides a process for producing a compound comprising two first polypeptides selected from the group consisting of SEQ ID NO: 9, SEQ ID NO: 10, SEQ ID NO: 11 and SEQ ID NO: 12 and two second polypeptides selected from the group consisting of SEQ ID NO: 16, SEQ ID NO: 17 and SEQ ID NO: 18, comprising cultivating the mammalian cell of the present invention under conditions such that the compound is expressed, and recovering the expressed compound.

In an embodiment, the present invention provides a process for producing a compound comprising two first polypeptides of SEQ ID NO: 9 and two second polypeptides of SEQ ID NO: 16, comprising cultivating the mammalian cell of the present invention under conditions such that the compound is expressed, and recovering the expressed compound.

In an embodiment, the present invention provides a process for producing a compound comprising two first polypeptides of SEQ ID NO: 10 and two second polypeptides of SEQ ID NO: 17, comprising cultivating the mammalian cell of the present invention under conditions such that the compound is expressed, and recovering the expressed compound.

In an embodiment, the present invention provides a process for producing a compound comprising two first polypeptides of SEQ ID NO: 11 and two second polypeptides of SEQ ID NO: 18, comprising cultivating the mammalian cell of the present invention under conditions such that the compound is expressed, and recovering the expressed compound.

In an embodiment, the present invention provides a process for producing a compound comprising two first polypeptides of SEQ ID NO: 12 and two second polypeptides of SEQ ID NO: 16, comprising cultivating the mammalian cell of the present invention under conditions such that the compound is expressed, and recovering the expressed compound.

In an embodiment of the above-described processes, the two polynucleotide sequences in the mammalian cell of the present invention are part of the same nucleic acid molecule.

In an embodiment, the present invention provides a compound obtainable by one of the aforementioned processes.

In an embodiment, the present invention provides a pharmaceutical composition, comprising a compound of the present invention, and an acceptable carrier, diluent, or excipient.

In an embodiment, the present invention provides a method of treating cancer, comprising administering to a patient in need thereof, an effective amount of a compound of the present invention. In a further embodiment, the present invention provides a method of treating cancer, comprising administering to a patient in need thereof, an effective amount of a compound of the present invention, wherein the cancer is breast cancer, ovarian cancer, gastric cancer, colorectal cancer, or hepatocellular carcinoma. In a further embodiment, the present invention provides a method of treating cancer, comprising administering to a patient in need thereof, an effective amount of a compound of the present invention, wherein the cancer is breast cancer, ovarian cancer, gastric cancer, colorectal cancer, non-small cell lung cancer, biliary tract cancer, or hepatocellular carcinoma. In a further embodiment, these methods comprise the administration of an effective amount of the compound of the present invention in simultaneous, separate, or sequential combination with one or more anti-tumor agents selected from the group consisting of cisplatin, carboplatin, liposomal doxorubicin, docetaxel, cyclophosphamide and doxorubicin, navelbine, eribulin, paclitaxel protein-bound particles for injectable suspension, ixabepilone, capecitabine, ramucirumab, FOLFOX (leucovorin, fluorouracil, and oxaliplatin), FOLFIRI (leucovorin, fluorouracil, and irinotecan), and cetuximab.

In a further embodiment, these methods comprise the administration of an effective amount of the compound of the present invention in simultaneous, separate, or sequential combination with one or more immuno-oncology agents selected from the group consisting of nivolumab, ipilimumab, pidilizumab, pembrolizumab, and durvalumab.

In a further embodiment, the present invention provides a method of treating cancer, comprising administering to a patient in need thereof, an effective amount of a compound of the present invention in simultaneous, separate, or sequential combination with one or more immuno-oncology agents, wherein the cancer is bladder cancer, kidney cancer, prostate cancer, or testicular cancer, and wherein the immuno-oncology agents are selected from the group consisting of nivolumab, ipilimumab, pidilizumab, pembrolizumab, and durvalumab.

In an embodiment, the present invention provides a method of treating breast cancer, comprising administering to a patient in need thereof, an effective amount of a compound of the present invention. In a further embodiment, these methods of treating breast cancer comprise the administration of an effective amount of the compound of the present invention in simultaneous, separate, or sequential combination with one or more anti-tumor agents selected from the group consisting of docetaxel, cyclophosphamide and doxorubicin, navelbine, eribulin, paclitaxel protein-bound particles for injectable suspension, ixabepilone, and capecitabine.

In an embodiment, the present invention provides a method of treating ovarian cancer, comprising administering to a patient in need thereof, an effective amount of a compound of the present invention. In a further embodiment, these methods of treating ovarian cancer comprise the administration of an effective amount of the compound of the present invention in simultaneous, separate, or sequential combination with one or more anti-tumor agents selected from the group consisting of cisplatin, carboplatin, and liposomal doxorubicin.

In an embodiment, the present invention provides a method of treating gastric cancer, comprising administering to a patient in need thereof, an effective amount of a compound of the present invention. In a further embodiment, these methods of treating gastric cancer comprise the administration of an effective amount of the compound of the present invention in simultaneous, separate, or sequential combination with ramucirumab.

In an embodiment, the present invention provides a method of treating hepatocellular carcinoma, comprising administering to a patient in need thereof, an effective amount of a compound of the present invention. In a further embodiment, these methods of treating hepatocellular carcinoma comprise the administration of an effective amount of the compound of the present invention in simultaneous, separate, or sequential combination with ramucirumab.

In an embodiment, the present invention provides a method of treating colorectal cancer, comprising administering to a patient in need thereof, an effective amount of a compound of the present invention. In a further embodiment, these methods of treating colorectal cancer comprise the administration of an effective amount of the compound of the present invention in simultaneous, separate, or sequential combination with one or more anti-tumor agents selected from the group consisting of FOLFOX (leucovorin, fluorouracil, and oxaliplatin), FOLFIRI (leucovorin, fluorouracil, and irinotecan), and cetuximab.

In an embodiment, the present invention provides a compound of the present invention, for use in therapy. In an embodiment, the present invention provides a compound of the present invention, for use in the treatment of cancer. In a further embodiment, the present invention provides a compound of the present invention, for use in the treatment of cancer, wherein the cancer is breast cancer, ovarian cancer, gastric cancer, colorectal cancer, or hepatocellular carcinoma. In a further embodiment, the present invention provides a compound of the present invention, for use in the treatment of cancer, wherein the cancer is breast cancer, ovarian cancer, gastric cancer, colorectal cancer, non-small cell lung cancer, biliary tract cancer, or hepatocellular carcinoma. In a further embodiment, for use in the treatment of cancer, the compound of the present invention in simultaneous, separate, or sequential combination with one or more anti-tumor agents selected from the group consisting of cisplatin, carboplatin, liposomal doxorubicin, docetaxel, cyclophosphamide and doxorubicin, navelbine, eribulin, paclitaxel protein-bound particles for injectable suspension, ixabepilone, capecitabine, ramucirumab, FOLFOX (leucovorin, fluorouracil, and oxaliplatin), FOLFIRI (leucovorin, fluorouracil, and irinotecan), and cetuximab.

In a further embodiment, for use in the treatment of cancer, the compound of the present invention in simultaneous, separate, or sequential combination with one or more immuno-oncology agents selected from the group consisting of nivolumab, ipilimumab, pidilizumab, pembrolizumab, and durvalumab.

In a further embodiment, for use in the treatment of cancer, the compound of the present invention in simultaneous, separate, or sequential combination with one or more immuno-oncology agents, wherein the cancer is bladder cancer, kidney cancer, prostate cancer, or testicular cancer, and wherein the immuno-oncology agents are selected from the group consisting of nivolumab, ipilimumab, pidilizumab, pembrolizumab, and durvalumab.

In an embodiment, the present invention provides a compound of the present invention, for use in the treatment of breast cancer. In a further embodiment, for use in the treatment of breast cancer, the compound of the present invention in simultaneous, separate, or sequential combination with one or more anti-tumor agents selected from the group consisting of docetaxel, cyclophosphamide and doxorubicin, navelbine, eribulin, paclitaxel protein-bound particles for injectable suspension, ixabepilone, and capecitabine.

In an embodiment, the present invention provides a compound of the present invention, for use in the treatment of ovarian cancer. In a further embodiment, for use in the treatment of ovarian cancer, the compound of the present invention in simultaneous, separate, or sequential combination with one or more anti-tumor agents selected from the group consisting of cisplatin, carboplatin, and liposomal doxorubicin.

In an embodiment, the present invention provides a compound of the present invention, for use in the treatment of gastric cancer. In a further embodiment, for use in the treatment of gastric cancer, the compound of the present invention in simultaneous, separate, or sequential combination with ramucirumab.

In an embodiment, the present invention provides a compound of the present invention, for use in the treatment of hepatocellular carcinoma. In a further embodiment, for use in the treatment of hepatocellular carcinoma, the compound of the present invention in simultaneous, separate, or sequential combination with one or more anti-tumor agents selected from the group ramucirumab.

In an embodiment, the present invention provides a compound of the present invention, for use in the treatment of colorectal cancer. In a further embodiment, for use in the treatment of colorectal cancer, the compound of the present invention in simultaneous, separate, or sequential combination with one or more anti-tumor agents selected from the group consisting of FOLFOX (leucovorin, fluorouracil, and oxaliplatin), FOLFIRI (leucovorin, fluorouracil, and irinotecan), and cetuximab.

In an embodiment, the present invention provides the use of a compound of the present invention for the manufacture of a medicament for the treatment of cancer. In a further embodiment, the present invention provides the use of a compound of the present invention for the manufacture of a medicament for the treatment of cancer, wherein the cancer is breast cancer, ovarian cancer, gastric cancer, colorectal cancer, or hepatocellular carcinoma. In a further embodiment, the present invention provides the use of a compound of the present invention for the manufacture of a medicament for the treatment of cancer, wherein the cancer is breast cancer, ovarian cancer, gastric cancer, colorectal cancer, non-small cell lung cancer, biliary tract cancer, or hepatocellular carcinoma.

In a further embodiment, the present invention provides the use of a compound of the present invention in simultaneous, separate, or sequential combination with one or more anti-tumor agents selected from the group consisting of cisplatin, carboplatin, liposomal doxorubicin, docetaxel, cyclophosphamide and doxorubicin, navelbine, eribulin, paclitaxel protein-bound particles for injectable suspension, ixabepilone, capecitabine, ramucirumab, FOLFOX (leucovorin, fluorouracil, and oxaliplatin), FOLFIRI (leucovorin, fluorouracil, and irinotecan), and cetuximab for the manufacture of a medicament for the treatment of cancer.

A compound of the present invention is an engineered, non-naturally occurring polypeptide complex. A DNA molecule of the present invention is a non-naturally occurring DNA molecule that comprises a polynucleotide sequence encoding a polypeptide having the amino acid sequence of one of the polypeptides in a compound of the present invention.

The antibody portion of the compound of the present invention is designed to have engineered CDRs and have some portions of the antibody (all or parts of the frameworks, hinge regions, and constant regions) to be of human origin that are identical with or substantially identical (substantially human) with frameworks and constant regions derived from human genomic sequences. Fully human frameworks, hinge regions, and constant regions are those human germline sequences as well as sequences with naturally-occurring somatic mutations and those with engineered mutations. The antibody portion of the compound of the present invention may comprise framework, hinge, or constant regions derived from a fully human framework, hinge, or constant region containing one or more amino acid substitutions, deletions, or additions therein. Further, the antibody portion of the compound of the present invention is preferably substantially non-immunogenic in humans.

The antibody portion of the compound of the present invention is an IgG type antibody and has four amino acid chains (two "heavy" chains and two "light" chains) that are covalently stabilized via intra- and inter-chain disulfide bonds. Each heavy chain is comprised of an N-terminal HCVR and a heavy chain constant region ("HCCR"). Each light chain is comprised of a LCVR and a light chain constant region ("LCCR"). When expressed in certain biological systems, antibodies having native human Fc sequences are glycosylated in the Fc region. Typically, glycosylation occurs in the Fc region of the antibody at a highly conserved N-glycosylation site. N-glycans typically attach to asparagine. Antibodies may be glycosylated at other positions as well.

Optionally, the antibody portion of the compound of the present invention contains an Fc portion which is derived from human $IgG_4$ Fc region because of a reduced ability to engage Fc receptor-mediated inflammatory mechanisms or to activate complement resulting in reduced effector function.

Further, the antibody portion of certain compounds of the present invention contains an $IgG_4$-PAA Fc portion. The $IgG_4$-PAA Fc portion has a serine to proline mutation at position 224, a phenylalanine to alanine mutation at position 230, and a leucine to alanine mutation at position 231. The S224P mutation is a hinge mutation that prevents half-antibody formation (phenomenon of dynamic exchange of half-molecules in IgG$_4$ antibodies). The F230A and L231A mutations further reduce effector function of the already low human IgG$_4$ isotype.

An isolated DNA molecule encoding a HCVR region can be converted to a full-length heavy chain gene by operably linking the HCVR-encoding DNA to another DNA molecule encoding heavy chain constant regions. The sequences of human, as well as other mammalian, heavy chain constant region genes are known in the art. DNA fragments encompassing these regions can be obtained e.g., by standard PCR amplification.

An isolated DNA encoding a LCVR region may be converted to a full-length light chain gene by operably linking the LCVR-encoding DNA to another DNA molecule encoding a light chain constant region. The sequences of human, as well as other mammalian, light chain constant region genes are known in the art. DNA fragments encompassing these regions can be obtained by standard PCR amplification. The light chain constant region can be a kappa or lambda constant region.

A "single chain fragment variable" or "scFv" or "scFv polypeptide" refers to an engineered, non-naturally occurring single folded polypeptide comprising the LCVR and the HCVR of an antibody linked through a scFv linker molecule. The scFv polypeptide portion of the compound of the present invention is an engineered, non-naturally occurring scFv that has been designed to have engineered CDRs and have some portions of the scFv (all or parts of the frameworks) to be of human origin that are identical with or substantially identical (substantially human) with frameworks derived from human genomic sequences. Fully human frameworks are those human germline sequences as well as sequences with naturally-occurring somatic mutations and those with engineered mutations. The scFv polypeptide portion of the compound of the present invention may comprise framework derived from a fully human framework containing one or more amino acid substitutions, deletions, or additions therein. Further, the scFv polypeptide portion of the compound of the present invention is preferably substantially non-immunogenic in humans. Optionally, the scFv polypeptide portion of the compound can have 44-100 disulfides from cysteine 44 in HCVR and cysteine 100 in LCVR (Cys44 and Cys100 numbering corresponds with a numbering that starts with the first amino acid of the scFv polypeptide). In such a scFv polypeptide, the HCVR and LCVR domains can be either in the HCVR-scFv linker-LCVR or LCVR-scFv linker-HCVR order. The scFv linker can be a flexible glycine-rich peptide linker which enables the HCVR and LCVR chains to be folded as a functional monomeric unit for recognizing an antigen. Optionally, the scFv linker is a glycine-rich linker such as a 2× G4S linker, a 3× G4S linker, a 4× G4S linker, or a 5× G4S linker.

Fusion of a scFv to an antibody can allow for multiple structures to form during expression and secretion. Firstly, scFv elements fused to an antibody can fold independently via an intramolecular interaction by which individual HCVR and LCVR elements located within the same polypeptide fold to form two separate and autonomous units, referred here to as Mab-scFv. Secondly, via an alternative folding pathway, scFv elements fused to an antibody can fold via intermolecular interactions by which a HCVR present in one polypeptide will fold with a LCVR present in the adjacent polypeptide to form a single co-folded species, here referred to as Mab-Diabody.

The term "linker" and "scFv linker" both refer to glycine-rich peptide linkers. The "linkers" are utilized in certain embodiments of the invention to link the antibody to the scFv, and the "scFv linkers" are utilized in certain embodiments of the invention to link the LCVR of the scFv to the HCVR of the scFv. Preferably, the peptide linkers are glycine-rich peptides with at least 5 amino acids, preferably of at least 10 amino acids, more preferably between 10 and 50 amino acids. In some embodiments of the present invention, said glycine-rich peptide linker is $(G_xS)_n$ with G=glycine, S=serine, (x=3 and n=3, 4, 5 or 6) or (x=4 and n=2, 3, 4 or 5). For example, in some embodiments of the present invention, said glycine-rich peptide linker is $(G_xS)_n$ with G=glycine, S=serine, x=4 and n=2, 3, 4 or 5 (i.e., GGGGSGGGGS (SEQ ID NO: 34), GGGGSGGGGSGGGGS (SEQ ID NO: 35), GGGGSGGGGSGGGGSGGGGS (SEQ ID NO: 36), or GGGGSGGGGSGGGGSGGGGSGGGGS (SEQ ID NO: 37), respectively.

The polynucleotides of the present invention will be expressed in a host cell after the sequences have been operably linked to an expression control sequence. The expression vectors are typically replicable in the host organisms either as episomes or as an integral part of the host chromosomal DNA. Commonly, expression vectors will contain selection markers, e.g., tetracycline, neomycin, and dihydrofolate reductase, to permit detection of those cells transformed with the desired DNA sequences.

The compound of the present invention may readily be produced in mammalian cells such as CHO, NS0, HEK293 or COS cells. The host cells are cultured using techniques well known in the art.

The vectors containing the polynucleotide sequences of interest (e.g., the polynucleotides encoding the polypeptides of the compound and expression control sequences) can be transferred into the host cell by well-known methods, which vary depending on the type of cellular host.

Various methods of protein purification may be employed and such methods are known in the art and described, for example, in Deutscher, *Methods in Enzymology* 182: 83-89 (1990) and Scopes, *Protein Purification: Principles and Practice,* 3rd Edition, Springer, N.Y. (1994).

In another embodiment of the present invention, the compound, or the nucleic acids encoding the same, is provided in isolated form. As used herein, the term "isolated" refers to a protein, peptide, or nucleic acid which is free or substantially free from any other macromolecular species found in a cellular environment. "Substantially free" as used herein means the protein, peptide, or nucleic acid of interest comprises more than 80% (on a molar basis) of the macromolecular species present, preferably more than 90%, and more preferably more than 95%.

The compound of the present invention, or pharmaceutical compositions comprising the same, may be administered by parenteral routes (e.g., subcutaneous and intravenous). A compound of the present invention may be administered to a patient alone with pharmaceutically acceptable carriers, diluents, or excipients in single or multiple doses. Pharmaceutical compositions of the present invention can be prepared by methods well known in the art (e.g., *Remington: The Science and Practice of Pharmacy,* 19$^{th}$ ed. (1995), A. Gennaro et al., Mack Publishing Co.) and comprise a compound, as disclosed herein, and one or more pharmaceutically acceptable carriers, diluents, or excipients.

The term "treating" (or "treat" or "treatment") refers to slowing, interrupting, arresting, alleviating, stopping, reducing, or reversing the progression or severity of an existing symptom, disorder, condition, or disease. A patient refers to a mammal, preferably a human with a disease, disorder, or condition that would benefit from inhibition of VEGFR2 and/or Ang2.

"Binds" as used herein in reference to the affinity of a compound, antibody, or scFv polypeptide for human VEGFR2 or human Ang2 is intended to mean, unless indicated otherwise, a $K_D$ of less than about $1 \times 10^{-8}$ M, preferably, less than about $1 \times 10^{-9}$ M as determined by common methods known in the art, including by use of a surface plasmon resonance (SPR) biosensor at 25° C. or 37° C. essentially as described herein. The term "selective" or "selectivity" used herein in reference to a compound of the present invention refers to a compound that binds a target, such as human Ang2, with a $K_D$ about 1000-, 500-, 200-, 100-, 50-, or about 10-fold lower than the compound binds other proteins, including member of the target family such as human Ang1, as measured by surface plasmon resonance at 25° C. or 37° C. Additionally, or alternatively, an Ang2 selective compound of the present invention binds human Ang2 but does not bind or only minimally binds human Ang1 when assayed by the methods described in the Example herein below.

"Effective amount" means the amount of a compound of the present invention or pharmaceutical composition comprising a compound of the present invention that will elicit the biological or medical response of or desired therapeutic effect on a tissue, system, animal, mammal or human that is being sought by the researcher, medical doctor, or other clinician. An effective amount of the compound may vary according to factors such as the disease state, age, sex, and weight of the individual, and the ability of the compound to elicit a desired response in the individual. An effective amount is also one in which any toxic or detrimental effect of the compound is outweighed by the therapeutically beneficial effects.

This invention is further illustrated by the following non-limiting examples.

EXAMPLE 1

Compound Expression and Purification

The polypeptides of the antibody portions, the scFv portions, and the antibody-linker-scFv of Compound C, Compound D, Compound E, and Compound F, and the nucleotide sequences encoding the same, are listed below in the section entitled "Amino Acid and Nucleotide Sequences." In addition, the SEQ ID NOs for the antibody portions, the scFv portions, and the antibody-linker-scFv of Compound C, Compound D, Compound E, and Compound F are shown in Table 1.

The compounds of the present invention, including, but not limited to Compound C, Compound D, Compound E, and Compound F, can be made and purified essentially as follows. An appropriate host cell, such as HEK 293 or CHO, can be either transiently or stably transfected with an expression system for secreting compounds using an optimal predetermined HC-linker-scFv:LC vector ratio (such as 1:3 or 1:2) or a single vector system encoding both HC-linker-scFv and LC. Clarified media, into which the compound has been secreted, may be purified using any of many commonly-used techniques. For example, the medium may be conveniently applied to a MabSelect column (GE Healthcare), or KappaSelect column (GE Healthcare) for Fab fragment, that has been equilibrated with a compatible buffer, such as phosphate buffered saline (pH 7.4). The column may be washed to remove nonspecific binding components. The bound compound may be eluted, for example, by pH gradient (such as 20 mM Tris buffer pH 7 to 10 mM sodium citrate buffer pH 3.0, or phosphate buffered saline pH 7.4 to 100 mM glycine buffer pH 3.0). Compound fractions may be detected, such as by SDS-PAGE, and then may be pooled. Further purification is optional, depending on the intended use. The compound may be concentrated and/or sterile filtered using common techniques. Soluble aggregate and multimers may be effectively removed by common techniques, including size exclusion, hydrophobic interaction, ion exchange, multimodal, or hydroxyapatite chromatography. The purity of the compound after these chromatography steps is greater than 95%. The product may be immediately frozen at −70° C. or may be lyophilized.

TABLE 1

| | SEQ ID NOs | | | |
|---|---|---|---|---|
| | Compound C | Compound D | Compound E | Compound F |
| HCVR of antibody | 1 | 2 | 3 | 4 |
| HC of antibody | 5 | 6 | 7 | 8 |
| HC of antibody + linker + scFv polypeptide | 9 | 10 | 11 | 12 |
| LCVR of antibody | 13 | 14 | 15 | 13 |
| LC of antibody | 16 | 17 | 18 | 16 |
| scFv polypeptide | 19 | 19 | 19 | 20 |
| HCVR of scFv polypeptide | 21 | 21 | 21 | 22 |
| LCVR of scFv polypeptide | 23 | 23 | 23 | 24 |

Assays

Binding Kinetics, Affinity, and Selectivity

The binding kinetics, affinity, and selectivity to human Ang2 and to human VEGFR2, for compounds of the present invention, may be determined by use of a surface plasmon resonance (SPR) biosensor such as a Biacore® 2000, Biacore® 3000, or a Biacore® T100 (GE HealthCare) according to methods known in the art.

The kinetics and equilibrium dissociation constant ($K_D$) for multiple species of soluble Ang2 (human, cyno, mouse, rabbit and dog) and VEGFR2 extracellular domain (ECD) (human, cyno, rabbit and dog) may be determined for compounds of the present invention at 25° C. or 37° C. using Biacore surface plasmon resonance methods. Human Ang2 and VEGFR2-ECD may be purchased from R&D Systems and Sino Biological, respectively. Protein A surface for capture of antibodies may be prepared using the following methods. Immobilization of soluble Protein A (Calbiochem, Cat: 539202) on a CM4 (Biacore #BR-1005-34) or CM5 (Biacore #BR-1000-99) may be prepared using EDC/NHS amine coupling method (Biacore #BR-1000-50). Briefly, the surfaces of all four flow cells may be activated by injecting a 1:1 mixture of EDC/NHS for seven minutes at 10 µL/min. After which, soluble protein A may be diluted to 50-100 µg/mL in 10 mM acetate buffer, pH 4.5, and immobilized for seven minutes onto flow cell (Fc) 2, 3 or 4 at a flow rate of 10 µL/min. Un-reacted sites still remaining on the chip surface may be blocked with a seven minute injection of ethanolamine at 10 µL/min. Running buffer may be HBS-EP+ (Biacore #BR-1006-69). Compound samples may be prepared at 1 µg/mL by dilution into running buffer. Discrete concentrations of Ang2 ligands ranging from 50 nM to 1.56 nM may be prepared using a two-fold serial dilution into running buffer. Each analysis cycle may consist of a series of five separate steps: (1) capture of compound onto separate flow cells (Fc2, Fc3, and Fc4), (2) injection (using kinject) of 250 μL (300-second surface contact time) of discrete concentrations of Ang2 or VEGFR2-ECD over all Fc at 50 μL/min, (3) return to buffer flow for 20 minutes to monitor dissociation phase, (4) regeneration of chip surfaces with a 10 μL (30-second contact time) injection of 10 mM glycine, pH1.5, (5) equilibration of chip surface with a 15 μL (45-second contact time) injection of HBS-EP+ running buffer. Resultant data may be processed using standard double-referencing and fit to a 1:1 binding model using Biacore 2000 Evaluation software, version 4.1, to determine the association rate ($k_{on}$, $M^{-1}$ $s^{-1}$ units), dissociation rate ($k_{off}$, $s^{-1}$ units). Calculation of the equilibrium dissociation constant ($K_D$) may be calculated from the following relationship, $K_D=k_{off}/k_{on}$, and is presented in molar units.

In experiments performed essentially as described in this assay, Compound C, Compound D, Compound E, and Compound F bind human Ang2 at 25° C. with a $K_D$ in the range of 407 pM to 673 pM (Table 2). Compound C, Compound D, Compound E, and Compound F bind human VEGFR2-ECD at 25° C. with a $K_D$ in the range of 528 pM to 1110 pM (Table 3). These compounds of the present invention demonstrate high affinity for both human Ang2 and human VEGFR2.

In experiments performed essentially as described in this assay, Compound F exhibited comparable binding kinetics and affinities for human Ang2 relative an Ang2 antibody with the same HCDRs and LCDRs as the scFv polypeptide portion of Compound F (Tables 4 and 5). This demonstrates that the potent binding kinetics of the Ang2 antibody with the same HCDRs and LCDRs as the scFv polypeptide portion of Compound F is retained in Compound F.

In experiments performed essentially as described in this assay, Compound F binds human, cynomolgus monkey, mouse rabbit and dog Ang2 with comparable high affinities, and Compound F binds human, cynomolgus monkey, rabbit and dog VEGFR2 with comparable high affinities.

TABLE 2

Biacore SPR hAng2 at 25° C.

| | $k_{on}$ ($10^5$ 1/Ms) | $k_{off}$ ($10^{-4}$ 1/s) | $K_D$ (pM) |
|---|---|---|---|
| Compound A | 1.83 | <0.1 | <100 pM |
| Compound B | 2.85 | <0.1 | <100 pM |
| Compound C | 2.26 | 1.05 | 462 |
| Compound D | 1.75 | 0.86 | 489 |
| Compound E | 2.39 | 0.97 | 407 |
| Compound F | 1.56 | 1.05 | 673 |

TABLE 3

Biacore SPR hVEGFR2-ECD at 25° C.

| | $k_{on}$ ($10^5$ 1/Ms) | $k_{off}$ ($10^{-4}$ 1/s) | $K_D$ (pM) |
|---|---|---|---|
| Compound A | 0.68 | 0.48 | 711 |
| Compound B | 0.81 | 0.41 | 513 |
| Compound C | 0.38 | 0.20 | 528 |
| Compound D | 0.34 | 0.29 | 860 |
| Compound E | 0.32 | 0.35 | 1110 |
| Compound F | 0.25 | 0.18 | 721 |

TABLE 4

Ang2 antibody (same HCDRs/LCDRs as scFv polypeptide portion of Cmpd F) Biacore SPR Ang2 Binding at 37° C. (n = 3)

| | $k_{on}$ (1/Ms) | $k_{off}$ (1/s) | $K_D$ (pM) |
|---|---|---|---|
| human Ang2 | 1.0 (±0.4) × $10^6$ | 0.7 (±0.2) × $10^{-4}$ | 80 ± 50 |
| cyno Ang2 | 2.7 (±0.2) × $10^6$ | 2.9 (±0.1) × $10^{-4}$ | 107 ± 6 |
| mouse Ang2 | 1.0 (±0.2) × $10^6$ | 1.1 (±0.1) × $10^{-4}$ | 109 ± 9 |
| rabbit Ang2 | 7.3 (±1.9) × $10^5$ | 1.5 (±0.1) × $10^{-4}$ | 210 ± 40 |
| dog Ang2 | 7.9 (±3.2) × $10^5$ | 1.1 (±0.4) × $10^{-4}$ | 140 ± 10 |

TABLE 5

Compound F Biacore SPR Ang2 Binding at 37° C. (n = 3)

| | $k_{on}$ (1/MS) | $k_{off}$ (1/s) | $K_D$ (pM) |
|---|---|---|---|
| human Ang2 | 8.2 (±2.4) × $10^5$ | 0.7 (±0.3) × $10^{-4}$ | 100 ± 70 |
| cyno Ang2 | 9.6 (±1.3) × $10^5$ | 2.8 (±0.1) × $10^{-4}$ | 300 ± 30 |
| mouse Ang2 | 3.6 (±0.9) × $10^5$ | 0.8 (±0.1) × $10^{-4}$ | 230 ± 20 |
| rabbit Ang2 | 2.7 (±0.7) × $10^5$ | 1.1 (±0.1) × $10^{-4}$ | 420 ± 60 |
| dog Ang2 | 3.6 (±1.6) × $10^5$ | 0.9 (±0.3) × $10^{-4}$ | 240 ± 30 |

TABLE 6

Compound F Biacore SPR VEGFR2-ECD Binding at 37° C. (n = 3)

| | $k_{on}$ (1/Ms) | $k_{off}$ (1/s) | $K_D$ (nM) |
|---|---|---|---|
| human VEGFR2 | 2.5 (±0.1) × $10^4$ | 1.2 (±0.2) × $10^{-4}$ | 4.6 ± 0.7 |
| cyno VEGFR2 | 3.4 (±0.2) × $10^4$ | 1.1 (±0.1) × $10^{-4}$ | 3.3 ± 0.4 |
| rabbit VEGFR2 | 3.8 (±0.5) × $10^4$ | 2.3 (±0.1) × $10^{-4}$ | 6.1 ± 1.0 |
| dog VEGFR2 | 4.1 (±0.3) × $10^4$ | 1.5 (±0.7) × $10^{-3}$ | 37 ± 1 |

Inhibition of Human Ang2 to Human Tie2 Interaction

The blocking of human Ang2 binding to its receptor human Tie 2 by a compound of the present invention may be measured in a solid phase in vitro ELISA assay. The aforementioned in vitro cell-based assay may also be used to establish comparable blocking activity of a compound of the present invention to an Ang2 antibody with the same HCDRs and LCDRs sequences as the scFv polypeptide portion of the compound.

For the assay, high binding 96-well ELISA plates (Costar #2592) may be coated with 4 μg/ml (in 100 μl) recombinant human Tie2-Fc (R&D Systems #313-TI), overnight at room temperature. The plates may be washed 3× with TBST (Tris buffered saline containing 0.05% Tween 20) and then may be blocked with 300 μl per well of blocking buffer (0.5% BSA/D-PBS) (BSA: Jackson ImmunoResearch #001-000-162; IgG-free, protease-free) for 1-2 hours at room temperature on an orbital shaker. During the blocking step, in separate polypropylene multiwell plates, 75 μl of 2× test antibodies (serially diluted 1:3 in blocking buffer) may be added with 75 μl of 2× biotinylated human Ang2 (R&D Systems #BT623) (also diluted in blocking buffer). The antibody/biotinylated Ang2 mixtures may then be incubated for 1 hour at 37° C. (final biotinylated Ang2 concentration was 100 ng/ml). The blocking solution may be removed from the Tie2-Fc coated ELISA plates, after which 50 μl per well of the antibody/biotinylated Ang2 mixtures may be added (in duplicate wells). The plates may then be incubated for 2 hours at room temperature, covered with plate sealers, on an orbital shaker. Plates may then be washed 3×, after which 100 µl per well of streptavidin-HRP (R&D Systems #DY998, may be diluted 1:200 in blocking buffer) may be added. Plates may then be incubated for 45 minutes at room temperature, covered with plate sealers, on an orbital shaker. Plates may then be washed again 3×.

Plates may then be developed by adding 100 µl per well of One Component TMB substrate (may be warmed to room temperature) (Surmodics/BioFX Labs #TMBW-1000-01). Development may be allowed to progress for 10 minutes at room temperature (plates may be covered with aluminum foil). Development may be stopped with 100 µl per well of acid stop solution (TMB stop solution, Surmodics/BioFX Labs #LSTP-1000-01). Plates may be mixed on an orbital shaker after which they may be read at 450 nm on an ELISA reader (Molecular Devices SpectraMax 190), using SOFTmax PRO 5.4.1 software (Molecular Devices Corp.). The A450 values reflect the amount of biotinylated Ang2 that remained bound to Tie-2-Fc. Reduction of A450 values reflected blocking of biotinylated Ang2 binding to Tie-2-Fc.

IC50 values for inhibition of Ang2 binding to Tie-2 may be calculated with GraphPad Prism 6, using Log-transformed X values. Nonlinear regression (curve fit) analysis (sigmoidal dose response, variable slope) may be performed on the log-transformed data to obtain IC50 values. If an experiment is performed more than once, the geometric mean IC50 value (and 95% confidence interval) between experiments may be calculated.

In experiments performed essentially as described in this assay, Compound F and an Ang2 antibody with the same HCDRs and LCDRs as the scFv polypeptide portion of Compound F result in geometric mean IC50 values (n=2) of 0.034 nM and 0.027 nM respectively. Compound F dose dependently blocks human Ang2 binding to human Tie-2 comparably to the Ang2 antibody with the same HCDRs and LCDRs as the scFv polypeptide portion of Compound F. This data indicates that the Ang2 scFv polypeptide portion of the compound has maintained potency in this assay that is comparable to that of the Ang2 antibody.

Neutralization of Ang2 Induced Phosphorylation of Tie2, but not Ang1 Mediated Phosphorylation The in vitro cell-based inhibition of human Ang2 by a compound of the present invention may be measured in a cell-based assay where Ang1 and Ang2 bind to and induce human Tie2 phosphorylation in a dose-dependent manner. The in vitro cell-based assay may be used to evaluate the ability of compounds of the present invention to selectively neutralize Ang2 and not Ang1 mediated phosphorylation of the Tie-2 receptor in a dose-dependent manner. An Ang2 antibody, an Ang1 antibody, and a control human IgG4 PAA isotype antibody may be included as positive and negative controls respectively.

The CHO-Tie2 cell line may be generated by stable transfection of a full-length human Tie2 receptor (with a 3×FLAG tag at the C-terminus). CHO-Tie2 cells may be maintained in complete medium of Hams F-12 (CellGro/Mediatech #10-080-CV), 10% heat inactivated FBS (Life Technologies/Invitrogen #10082-147), 1× antibiotic-antimycotic (Life Technologies/Invitrogen #15240-062), 1.25 mg/ml G418 (Corning Cellgro #30-234-CI), 10 µg/ml puromycin (Calbiochem #540411), and 0.078% sodium bicarbonate (Thermo Hyclone #SH30033.01).

For the assay, CHO-Tie2 cells may be resuspended to 10,000 cells per well (in 100 ul growth medium), into the inner 60 wells of poly-lysine coated 96-well plates (BD Biocoat #356640). 200 µl of D-PBS may be placed into the edge wells to reduce evaporation. Cells may be incubated overnight at 37° C., 95% RH, 5% $CO_2$. The next day, cells may be washed once and medium may be replaced with 100 µl serum-free growth medium containing 0.1% BSA (Sigma #A7979, low endotoxin). Cells may then be starved for 7.5 to 24 hours in serum-free medium at 37° C., 95% RH, 5% $CO_2$. During the starvation period, compounds (at 6× the final concentrations) may be serially diluted 1:2 in polypropylene plates in serum-free growth medium containing 0.1% BSA. Human Ang2 (R&D Systems #623-AN, reconstituted in D-PBS/0.1% BSA) and human Ang1 (R&D Systems #923-AN, reconstituted in D-PBS/0.1% BSA) may also be diluted to 6× the final concentration in serum-free growth medium containing 0.1% BSA. Compounds and the Ang2 or Ang1 ligand may then be mixed at a 1:1 ratio in polypropylene plates and may be incubated for 1 hour at 37° C. The compound/ligand mixtures may then be added at 50 µl per well to the cells (in triplicate wells per treatment) and may be incubated for 13 minutes to 21 hours at 37° C., 95% RH, 5% $CO_2$. The final concentration range of compounds may be 0.0625-283 nM, and the final concentration of human Ang2 and Ang1 may be 0.3 µg/ml (approx. 6 nM) and 0.5 µg/ml (approx. 8.9 nM), respectively. After the incubation time, medium may be quickly and fully removed from the cells, and cells may be lysed in 60 µl per well of cold 1× Tris Lysis Buffer (Meso Scale Discovery #R60TX; 150 mM NaCl, 20 mM Tris pH 7.5, 1 mM EDTA, 1 mM EGTA, 1% Triton X-100) which may contain freshly added protease and phosphatase inhibitors (1× protease inhibitor cocktail, Sigma #P8340; 1× phosphatase inhibitor cocktail 2, Sigma #P5726; 1× phosphatase inhibitor cocktail 3, Sigma #P0044; 1 mM final activated sodium orthovanadate (EMD Chemicals #567540)). Plates may then be placed on ice for 10 minutes, after which they may be placed on an orbital shaker at low speed for 25 minutes at 4° C. The plates may then be sealed and frozen at −80° C.

The day before analysis for phospho-Tie2 (with a human phospho-Tie2 DuoSet ELISA kit from R&D Systems, #DYC2720), high binding ELISA plates (Greiner BioOne, #655081) may be coated overnight at 4° C. with 4 µg/ml mouse anti-human total Tie2 capture antibody in 1×ELISA coating buffer (Surmodics/BioFX Labs #COAT-1000-01).

The day of phospho-Tie2 measurement, plates containing lysates may be thawed on ice. The coated ELISA plates may be washed with wash buffer (1×TBST containing 0.05% Tween 20) and blocked with 300 µl per well of blocking buffer (1% BSA (Jackson ImmunoResearch #001-000-162; IgG-free, protease-free), 0.01% sodium azide) for a minimum of 1 hour at room temperature on an orbital shaker (while covered with plate sealers). During blocking, lysates may be diluted 1:5 or 1:10 in polypropylene plates in cold lysis buffer containing protease and phosphatase inhibitors. ELISA plates may be blocked and washed 4×, and 100 µl per well of diluted lysates (or phospho-Tie2 ELISA standards) may be added and incubated for 2 hours at room temperature, covered with sealers, on an orbital shaker. Plates may be washed 4× and 100 µl per well of HRP conjugated mouse anti-phospho tyrosine (diluted as recommended on the vial, in TBST/0.1% BSA) may be added. Plates may then be covered with sealers, and incubated for 2 hours at room temperature on an orbital shaker. Plates may then be washed 6× and removal of liquid from the wells may be ensured. Plates may then be developed by adding 100 µl per well of One Component TMB substrate (Surmodics/BioFX Labs #TMBW-1000-01). Plates may be allowed to develop for 20 or 30 minutes at room temperature covered with aluminum foil. Development may be stopped with 100 µl per well of acid stop solution (TMB stop solution, Surmodics/BioFX Labs #LSTP-1000-01). Plates may then be mixed on an orbital shaker. The ELISA plates may be read at 450 nm on an ELISA reader (Molecular Devices SpectraMax 190), using SOFTmax PRO 5.4.1 software (Molecular Devices Corp.). Phospho-Tie2 values for the samples may be obtained from the standard curve (4-parameter logistic fit), and multiplied by the dilution factor of 5 or 10. Percent inhibition may be calculated by the following formula: (pTie2 value of treatment-mean pTie2 value of Ang2 alone treatment)/(mean medium alone pTie2 value-mean pTie2 value of Ang2 alone treatment)*100.

IC50 values for inhibition of Ang2 induced phospho-Tie2 may be calculated with GraphPad Prism 4, using Log-transformed X values. Nonlinear regression (curve fit) analysis (sigmoidal dose response, variable slope) may be performed on the log-transformed data to obtain $IC_{50}$ values. If an experiment was performed more than once, the geometric mean $IC_{50}$ value (and 95% confidence interval) between experiments may be calculated.

In experiments performed essentially as described in this assay, Compound F dose-dependently neutralizes human Ang2 induced phospho-Tie2 in CHO-Tie2 cells with an IC50 of 0.587 nM (n=3) while an Ang2 antibody with the same HCDRs and LCDRs as the scFv polypeptide portion of Compound F has an IC50 of 0.773 nM. The results indicate that Compound F neutralizes Ang2 induced phospho-Tie2, but does not neutralize human Ang1 induced phospho-Tie2 in CHO-Tie-2 cells when compared to the positive control Ang1 antibody. Moreover, this data indicates that the Ang2 scFv polypeptide portion of Compound F has maintained potency in this assay that is comparable to that of the Ang2 antibody with the same HCDRs and LCDRs as the scFv polypeptide portion of Compound F.

Neutralization of VEGF165 Induced Phosphorylation of VEGFR2

The in vitro cell-based inhibition of human VEGFR2 may be measured in a cell-based assay where binding of VEGF165 to the VEGFR2 on a VEGFR2 expressing cell line, induces VEGFR2 phosphorylation in a dose-dependent manner. The aforementioned assay may be used to evaluate the ability of a compound of the present invention to selectively neutralize VEGF165 mediated phosphorylation of the VEGFR2 receptor in a dose-dependent manner. A VEGFR2 antibody and an irrelevant antibody human IgG4 PAA isotype may be included as a positive and negative control, respectively.

For the assay, VEGFR2 expressing human ECFC (endothelial colony forming cells, derived from umbilical cord blood endothelial progenitors) (Endgenitor Technologies, Lot 100506-14-P4, passages 10-12) may be seeded at 14,000 cells per well (in 100 µl growth medium), into the inner 60 wells of collagen I coated 96-well plates (BD Biocoat #35-4407) in growth medium: EGM-2MV BulletKit (Lonza #CC-4147). Components of the included EGM-2MV Singlequot bag may be added to 500 ml of EBM-2 basal medium, adjusted to 10% final FBS concentration (Life Technologies/Invitrogen #10082-147, heat inactivated). 250 µl of growth medium may be placed into the edge wells to reduce evaporation. Cells may be incubated ON at 37° C., 95% RH, 5% $CO_2$. The next day, medium may be removed and replaced with 100 µl serum-free EBM-2 basal medium containing 0.1% BSA (Sigma #A7979, low endotoxin). Cells may be starved for 6½ hours at 37° C., 95% RH, 5% $CO_2$. During the starvation period, compounds (at 6× the final concentrations) may be serially diluted 1:4 in polypropylene plates in EBM-2/0.1% BSA. Human VEGF165 may be diluted to 6× the final concentration in EBM-2/0.1% BSA. Compounds (or EBM-2/0.1% BSA medium alone) may be added in triplicate at 25 µl to the cells, and cells may be incubated for 45 minutes at 37° C., 95% RH, 5% $CO_2$. Cells may be treated with 25 µl of 6×VEGF165 for 5 minutes at 37° C., 95% RH, 5% $CO_2$. (The final concentration range of compounds may be 0.018-300 nM, and the final concentration of human VEGF165 may be 0.16 nM). Medium may be removed from the cells, and cells may be lysed in 60 µl per well of cold 1× Tris Lysis Buffer (Meso Scale Discovery #R60TX; 150 mM NaCl, 20 mM Tris pH 7.5, 1 mM EDTA, 1 mM EGTA, 1% Triton X-100) containing freshly added 1× protease and phosphatase inhibitors (included with the phospho-VEGFR2 assay kit). Plates may be placed on ice for 10 minutes, then on an orbital shaker at low speed for 20 minutes at 4° C. Plates may then be sealed and frozen at −80° C.

The day of phospho-VEGFR2 measurement, plates containing lysates may be thawed on ice. Phospho-VEGFR2 levels may be measured using a phospho-VEGFR2 (Tyr1054) whole cell lysate kit, (Meso Scale Discovery #K151DJD). Meso Scale assay plates, pre-coated with an antibody against phospho-VEGFR2, may be blocked with 150 µl per well of blocking buffer (3% blocker A in TBST) for a minimum of 1 hour at room temperature on an orbital shaker (while covered with plate sealers). The plates may be washed 3× with 1× Meso Scale wash buffer, and 50 µl of lysates may be added per well (may be incubated for 1 hour at room temperature, covered with sealers, on an orbital shaker). The plates may be washed, and 3×, 25 µl per well of 1×MSD SULFO-TAG™ conjugated anti-total VEGFR2 (diluted in the manufacturer's recommended antibody diluent) may be added, and incubated for 1 hour at room temperature, covered with sealers, on an orbital shaker. Plates may be washed 3× and removal of liquid from the wells may be ensured. 150 ul per well of 1× Read Buffer T may be added to the plates, and they may be read immediately on a Meso Scale Discovery SECTOR Imager MA6000. Percent inhibition may be calculated by the following formula: (signal value of treatment-mean signal value of VEGF+huIgG treatment)/(mean starve medium alone signal value-mean signal value of VEGF+huIgG treatment)*100.

IC50 values for inhibition of VEGF165 induced phospho-VEGFR2 may be calculated with GraphPad Prism 6, using Log-transformed X values. Nonlinear regression (curve fit) analysis (sigmoidal dose response, variable slope) may be performed on the log-transformed data to obtain IC50 values. If an experiment was performed more than once, the geometric mean IC50 value (and 95% confidence interval) between experiments may be calculated.

In experiments performed essentially as described in this assay, Compound F dose dependently neutralizes human VEGF165-induced phospho-VEGFR2 in ECFC with an IC50 mean of 0.83 nM (n=3), while IMC-1121B has an IC50 mean of 0.52 nM (n=3). This indicates that the VEGFR2 antibody portion of the compound has maintained potency in Compound F that is comparable to that of IMC-1121B in this cell based assay.

Neutralization of VEGF165 Induced Cell Proliferation

The in vitro cell-based inhibition of human VEGFR2 by a compound of the present invention may be measured in a cell-based assay where VEGF165 induces human VEGFR2 proliferation in a dose-dependent manner. The ability of a compound of the present invention to neutralize human VEGF165 induced proliferation via VEGFR2 may be measured in human HMVEC-d (dermal microvascular endothelial cells). VEGFR2, Ang2, and irrelevant human IgG4 PAA antibodies may be included as positive and negative controls.

Human dermal microvascular endothelial cells may be isolated from newborn male foreskin, and may be confirmed for CD31, VEGFR2, and acetylated LDL expression. HMVEC-d may be maintained in complete growth medium MCDB131 (Mediatech #15-100-CV), 2 mM L-glutamine (Thermo Scientific #SH30034.01), 1× penicillin-streptomycin (Life Technologies/Invitrogen #15140), MGVS supplement (Life Technologies/Invitrogen #S-005-25) as directed for 500 ml medium; which may be supplemented to contain 4.9% FBS, 1 μg/ml hydrocortisone, 3 ng/ml human FGF, 10 μg/ml heparin, 1 ng/ml human EGF, and 0.08 mM dibutyryl cyclic AMP.

For the assay, HMVEC-d cells at passage 5 may be washed once in pre-warmed growth medium, and may be resuspended to 2,000 cells per well (in 100 μl growth medium), into the inner 60 wells of white-walled, clear bottom 96-well plates (BD #35-3377). 250 μl of supplement-free medium may be added to the edge wells to reduce evaporation. Compounds and human VEGF165 (Lot ALY-BE01241-033) at 4× the final concentrations may be serially diluted 1:4 in polypropylene plates in supplement-free medium. Compounds (or supplement-free medium alone) may be added to the cells in triplicates at 50 μl per well, which may be followed by 50 μl per well of the 4× VEGF165. The plates may then be incubated for 5 days at 37° C., 95% RH, 5% CO2. The final concentration range of compounds may be 0.012-800 nM, and the final concentration of human VEGF165 may be 0.5 nM.

After the incubation period, the plates and CellTiter Glo substrate (Promega #G7571) may be equilibrated to room temperature for 30 minutes. 100 μl per well of CellTiter Glo reagent may be added, and plates may be placed on an orbital shaker for 2 minutes at room temperature. Plates may be incubated for an additional 10 minutes, then luminescence may be recorded (1 second integration time) on a Perkin Elmer Wallac Victor 3 Model 1420 reader.

$IC_{50}$ values for inhibition of VEGF165 induced proliferation may be calculated with GraphPad Prism 6, using Log-transformed X values. Medium alone values may be included as the highest point of curves; the X-value (concentration) for medium alone may be set to 100× higher than the highest X value. Also, the VEGF alone values may be included as the lowest point of the curves; the concentration for VEGF alone may be set to 100× lower than the lowest X value. Nonlinear regression (curve fit) analysis (sigmoidal dose response, variable slope) may be performed on the log-transformed data to obtain IC50 values.

In experiments performed essentially as described in this assay, Compound F dose dependently neutralizes human VEGF165-induced proliferation of HMVEC-d similarly to IMC-1121B with $IC_{50}$ means of 19.24 nM and 31.36 nM, respectively (n=2). This indicates that the VEGFR2 antibody portion of the compound has maintained potency in Compound F that is comparable to IMC-1121B in this cell based assay.

Inhibition of VEGF165 Induced Cord Formation

The in vitro inhibition of VEGF induced cord formation may be measured in an in vitro co-culture system. The aforementioned assay may be used to measure inhibition of VEGF induced cord formation by a compound of the present invention. A VEGFR2 antibody may be included as a positive control.

For this assay, adipose derived stem cells (ADSC; Lonza #PT5006, lot#OF4505-01) may be cultured on Corning culture flasks (Corning #431082) in EGM-2MV medium (Lonza #CC3202). Endothelial colony forming cells (ECFC; Lonza, lot#EGT-ECFC100506r) may be cultured on Collagen I coated flasks (BD Biosciences #356486) in EGM-2MV medium supplemented with 5% heat inactivated FBS (Gibco #10082-147). ADSC at passages 4-6 may be harvested from culture flasks which may be rinsed with DPBS (Hyclone #SH30028.03) followed by TrypLE Express (Gibco #12605-010). ADSC cells may be suspended in Basal Medium (MCDC-131 (Gibco #10372-019) supplemented with 10 μg/ml insulin, 1 μM dexamethasone, 30 μg/ml ascorbic acid, 10 μg/ml human transferrin and 50 μg/ml tobramycin). Viable cell count may be determined and cells may be seeded onto black, clear bottomed 96-well plates (BD Falcon #353219) at $4 \times 10^4$ cells per well in 100 μl Basal Medium. Cells may be incubated at 37° C. in 5% $CO_2$ overnight to allow attachment. Next day, ECFC at passages 7-10 may be harvested in Basal Medium as above and viable cell count may be adjusted to $4 \times 10^4$ cells per ml. Medium may be removed from ADSC cells and 100 μl ECFC cell suspension may be added to each well. Plates may be incubated at 37° C. in 5% $CO_2$ for 2-3 hours to allow cells to settle on top of the ADSC monolayer. IMC-1121B and compounds of the present invention may be diluted to 80 μg/ml in Basal Medium, and then may be serially diluted 1:3 with Basal Medium to produce a nine point dose response series. 50 μl of each dilution of compound may be added to the co-culture. 50 μl of an 80 ng/ml solution of rhVEGF (R&D #293-VE/CF, 50 μg/ml in DPBS) prepared in Basal Medium may be added to the co-culture+compound combination. Final concentrations for compounds and rhVEGF may be 20 μg/ml and 20 ng/ml respectively. Positive control for the assay may include 20 ng/ml rhVEGF in the absence of compound. Negative control for the assay may include Basal Medium without rhVEGF. Plates may then be incubated at 37° C. in 5% $CO_2$ for 3 days to allow cords to form.

At the end of the incubation period, medium may be aspirated from each well and 100 ul room temperature 80% ethanol may be carefully added. Plates may be incubated at room temperature for 20 minutes. Ethanol solution may be aspirated and wells may be washed twice with 150 ul DPBS. Anti-huCD31 (R&D #AF806 Affinity purified sheep IgG, 200 ug/ml) and MAB Anti-Actin, alpha-Smooth Muscle-Cy3 (Sigma #C6198) may be each diluted 1:250 in 2.5% FBS/DPBS. 100 μl antibody mix may be added to wells and plates may be incubated at 37° C. in 5% $CO_2$ for 2 hours. Plates may then be aspirated and wells may be washed twice with 150 ul DPBS. Alexa Fluor 488 donkey anti-sheep IgG (H+L) (Life Technologies #A11015) may be diluted 1:400 and Hoescht 33342 (Life Technologies #H3570) may be diluted 1:1000 in 2.5% FBS/DPBS and 100 μl per well may be added to plates. Plates may be incubated at room temperature protected from light for 30 minutes. Wells may then be washed twice with 150 μl DPBS. 150 μl DPBS may be added to each well and plates may be sealed with black adhesive seals (PerkinElmer #6050173).

Plates may be read on the ArrayScan VTI HCS Reader (Cellomics-Thermo Fisher) using the Tube Formation Bioapplication. Total Tube Area data may be plotted against compound concentrations in nM in GraphPad Prism 6. Compound concentrations may be transformed into log data and $IC_{50}$ values for inhibition may be calculated by nonlinear regression (sigmoidal dose response, variable slope). Each experiment may represent the mean of triplicates and triplicate experiments may be expressed as the geometric means and 95% confidence intervals may be calculated.

In experiments performed essentially as described in this assay, Compound F dose dependently inhibits human VEGF-induced cord formation in the ADSC/ECFC co-culture system, comparably to IMC-1121B with mean $IC_{50}$ of 6.04 nM and 5.6 nM, respectively (n=3). This indicates that the VEGFR2 antibody portion of the compound has maintained potency in Compound F that is comparable to IMC-1121B in this cell based assay.

Repression of Ang2 Induced Blood Vessel Development

The in vivo repression of physiological angiogenesis by an Ang2 antibody may be measured in a model of blood vessel development in the mouse retina. The aforementioned assay may be used to study the ability of compounds of the present invention to repress physiological angiogenesis in the mouse retina.

For this assay, the day of mouse pup delivery by the pregnant females may be marked P0 (postnatal day 0). Following delivery, at days two and four (P2 and P4) pups may be injected with vehicle control (PBS) or 10 mg/kg of Ang2 antibody or 13.5 mg/kg of the compound to maintain comparable molar amounts of the molecules. At P5 mice may be sacrificed and eyes may be harvested and may be fixed in formalin for 5 hours and may be washed with PBS.

Retinas may then be dissected, and may be stained with anti-CD31 diluted at 1:200 (BD Pharmingen; clone MEC 13.3; Catalog 553370), and anti-SMA-FTIC diluted at 1:200 (Sigma; Clone1A4 Catalog F3777). For the anti-CD31 treated retinas an anti-Rat Alexa-647 diluted at 1:400 (Jackson Immuno Research; Catalog 712-606-153) may be used as a secondary antibody. Acquisition of the retinas may be done by using Nikon Ti, and quantifications of vascular progression, number of sprouting tip cells, and vascular density of remodeling plexus may be performed by using FIJI software. High magnification images may be acquired using a confocal Nikon A1.

In experiments performed essentially as described in this assay, Compound F and an Ang-2 Ab with the same HCDRs and LCDRs as the scFv polypeptide portion of Compound F comparably repress vascular progression, reduce both the number of endothelial tip cells and vascular density, as well as increase pericyte coverage (Table 7). These results from this in vivo model indicate that the Ang2 scFv polypeptide portion of Compound F has maintained function and potency that is comparable to an Ang2 antibody with the same HCDRs and LCDRs as the scFv polypeptide portion of Compound F.

TABLE 7

| Parameters | Vehicle | Ang2 mAb | Compound F |
|---|---|---|---|
| Vascular progression | | | |
| Mean (%) | 100 | 57.29 | 49.01 |
| Std. Error of Mean | 2.956 | 4.296 | 3.679 |
| P value (Vehicle vs. Compounds) (Dunnett's test) | | <0.0001 | <0.0001 |
| P value (Ang2 mAb vs. Compound F) (Dunnett's test) | | | 0.2543 |

TABLE 7-continued

| Parameters | Vehicle | Ang2 mAb | Compound F |
|---|---|---|---|
| Number of tip cells | | | |
| Mean (%) | 100 | 61.77 | 47.26 |
| Std. Error of Mean | 6.749 | 6.658 | 4.719 |
| P value (Vehicle vs. Compounds) (Dunnett's test) | | <0.0001 | <0.0001 |
| P value (Ang2 mAb vs. Compound F) (Dunnett's test) | | | 0.1354 |
| Vascular density | | | |
| Mean (%) | 100 | 60.52 | 62.97 |
| Std. Error of Mean | 5.728 | 2.178 | 2.935 |
| P value (Vehicle vs. Compounds) (Dunnett's test) | | <0.0001 | <0.0001 |
| P value (Ang2 mAb vs. Compound F) (Dunnett's test) | | | 0.9476 |

Physical Stability, Chemical Stability, and Product Quality

Product qualities, including aggregate level, homogeneity during expression, physical stability, and chemical stability, are evaluated to identify any issues and ensure suitability for therapeutic uses.

Free Light Chain Mis-Pairing

During the purification and analysis of Compound A (two first polypeptides of SEQ ID NO: 38 and two second polypeptides of SEQ ID NO: 39), and Compound B (two first polypeptides of SEQ ID NO: 40 and two second polypeptides of SEQ ID NO: 39), the presence of non-covalent light chains from the antibody portion of the compound is detected. Purification to remove the mis-folded species results in poor final yield of the desired compound. The instability of the interface between VH and VL of the antibody portion of the compound, and the folding of the domains of the scFv polypeptide are both found to contribute to the problem. Mutations in the framework of the antibody portion of the compound are used to eliminate this light chain mis-pairing problem, however, the problem was only reduced and not resolved. A number of germline frameworks in the scFv polypeptide are tried, but the expression profiles are not improved. Engineering of the CDRs and frameworks of the antibody portion of the compound in combination with scFv polypeptide engineering is required to produce the desired result of acceptable levels of light chain mis-pairing.

Mass-spec analysis confirms the existence of free LC associated with Compound A, either as non-covalently linked association or as covalently linked species. To further quantify the percentage of LC associations, a HIC-HPLC (TSKgel butyl-NPR 4.6 mm ID×10 cm, 2.5 um; TOSOH cat#42168) method is employed. In this analysis, a protein sample is injected onto a Butyl-NPR column and eluted according to their hydrophobicity. Through weak hydrophobic interaction, monomer, aggregates and various states of LC associated species are resolved sequentially during elution. Method development such that test articles are prepared in 1 mg/ml solution in buffer 50 mM Potassium Phosphate, 1 M ammonium sulphate, pH 6.7 and 50 µg of sample is injected onto a TSKgel butyl-NPR column at flow rate of 1 ml/min on Agilent LC 1260 system. With a salt gradient from 1 M ammonium sulphate to zero in 50 mM Potassium Phosphate buffer, pH 6.7, three protein peaks are resolved and fractionated. Each fractionated peak is analyzed by LCMS and identified as monomer Mab-scFv, bi-cysteinylated Mab-scFv with one extra cysteinylated LC, and bi-cysteinylated Mab-scFv with two extra cysteinylated LC. With peak assignments confirmed by LCMS, the final chromatograph (A214 detection) is integrated to calculate the total percentage of LC association.

In experiments performed as described above, the compound with an M111L mutation of Compound B to fix oxidation was found to exhibit 55% LC association. Through engineering of the variable domain of VR2 and the frameworks, the final molecules Compound C, Compound D, Compound E, and Compound F were found to exhibit no detectable LC association as detected by HIC-HPLC analysis (Table 8).

TABLE 8

|  | LC % |
|---|---|
| Compound B with M111L | 55 |
| Compound C | 0 |
| Compound D | 0 |
| Compound E | 0 |
| Compound F | 0 |

Mab-Diabody Formation

To facilitate measurement of Mab-Diabody/Mab-scFv ratios in compounds of the present invention, the following treatments are performed. Typically 20 µg of the compound of the present invention is buffer exchanged into 50 mM sodium phosphate containing 150 mM sodium chloride, pH 6.6 using an Amicon Ultra-0.5 mL centrifugal filter device. Samples are concentrated to approximately 30 µl and then mixed with 1 µl of freshly prepared FABricator enzyme (Genovis, Cat: A0-FR1-020; 2000 U dissolved in 30 µl of ddH$_2$O) and incubated at 37° C. overnight. Digested samples (1 µl) are subjected to LC/UV/MS analysis using the Waters Acquity UPLC coupled to a Waters Xevo G2-S mass spectrometer. The samples are loaded onto a PLRP-S 50×1.0 mm, 1000 Å, 5 um reverse phase column (Proxeon, Cat: PL1312-1502) at a flow rate of 0.3 ml/min and column temperature of 80° C. Samples are eluted from the column using a gradient of TFA in Acetonitrile. The eluate is analyzed first by UV at 214 nm with the flow then directed to the mass spectrometer for analysis using sensitivity mode, positive polarity with an acquisition range of 400-4000 m/z.

In experiments performed essentially as described in this assay, Compound B exhibits less than 1% Mab-Diabody. Compound C, Compound D, and Compound E, incorporating all the modifications made to Compound B to reduce oxidation and light chain mis-pairing problems, surprisingly had approximately 5-6% Mab-Diabody. The sequence changes incorporated into Compound F had a Mab-Diabody percentage of less than 1% Mab-Diabody which is comparable to Compound B.

Oxidation

Chemical stability of compounds of the present invention may be evaluated by producing varied formulation conditions which may be subjected to temperature hold stress. Changes in chemical stability may be monitored by established LCMS peptide mapping techniques. Briefly, test articles may be obtained and diluted to a final concentration of 1 mg/ml in the following formulation buffers: 10 mM Citrate, pH 5.0, 10 mM Citrate, pH 6.5, 1×PBS, pH 7.4 and 10 mM Tris, pH 8.0 and then subjected to exhaustive dialysis at 4° C. in each respective buffer to ensure complete buffer exchange. Buffer exchanged samples may then be subjected to incubation at either 4° C. or 40° C. for four weeks, after which samples may be analyzed by LCMS as follows. Stressed material may be buffer exchanged into 8M guanidine to denature prior to reduction with DTT followed by subsequent alkylation by iodoacetamide. Reduced and alkylated protein may then be buffer exchanged into Tris, pH 7.5 and digested with trypsin at a 20:1 molar ratio at 37° C. for four hours. Digestion may be quenched with the addition of 1 µL glacial acetic acid. Separation of digested peptide fragments may be achieved by capture onto a Zorbax 1.8 µm C18 2.1 mm×50 mm pre-equilibrated 0.2% Formic Acid in water and subsequent elution using a 0.2% Formic acid in acetonitrile gradient operated at 0.3 ml/min. Eluted peptides may be immediately analyzed using a Agilent ESI-QTOF set to scan in positive ion mode from 300 m/z to 2000 m/z at 1 scan/second. The ESI source may be set at 4000 V and the temperature at 350° C., nebulizer gas at 40 psi and cone gas at 12 psi. Agilent Mass Hunter Bio-confirm software may be used to align the tryptic peptide mass spectrum to the protein sequence.

In experiments performed essentially as described in this assay, Compound B exhibits 14.2% oxidation at position M111 on the heavy chain of the VEGFR2 antibody portion of the compound when subjected to temperature stress at 40° C. at pH 8.0. To circumvent issues related to oxidation at this position, a single point mutation that changes methionine 111 to leucine in Compounds C, D, E, and F is made to eliminate the possibility of chemical modification at this position.

Plasma Pharmacokinetics (PK) and Pharmacodynamics (PD) Following a Single Intravenous Dose to Male Cynomolgus Monkeys The PK and PD of compounds of the present invention may be measured in Cynomolgus Monkeys after a single intravenous dose.

Male Cynomolgus Monkeys (n=2/group) may be administered a single intravenous dose of a compound of the present invention. Blood may be sampled between 2-672 hours post-dose and plasma isolated for quantifying compound plasma levels using three ELISA methods.

The total human IgG method may utilize an ELISA format to measure the concentration of the compound of the present invention (total human IgG). Standards, controls, and test samples may be incubated with goat anti-human F(ab')2 which has been immobilized on a microtiter plate. After incubation, a mouse anti-human IgG$_4$-HRP (horseradish peroxidase) may be added to the wells. Once unbound enzyme is washed away, SureBlue® TMB (tetramethylbenzidine) substrate solution may be added to the wells. The color development may be stopped by the addition of an acidic solution and the optical density measured at 450 nm with wavelength correction set to 630 nm. The assay range may be 30-700 ng/ml.

The VEGFR2 antigen capture method may utilize an ELISA format to measure the concentration of the compounds of the present invention (VEGFR2 antigen capture). Standards, controls and test samples may be incubated on a microtiter plate coated with human VEGFR2. After incubation, a mouse anti-human IgG$_4$-HRP (horseradish peroxidase) may be added to the wells. Once unbound enzyme is washed away, SureBlue® TMB (tetramethylbenzidine) substrate solution may be added to the wells. The color development may be stopped by the addition of an acidic solution and the optical density measured at 450 nm with wavelength correction set to 630 nm. The assay range may be 80-2000 ng/ml.

The Ang2 antigen capture method utilizes an ELISA format to measure the concentration of the compounds of the present invention (Ang2 antigen capture). Standards, controls and test samples may be incubated on a microtiter plate coated with Ang2. After incubation, a mouse anti-human IgG$_4$-HRP (horseradish peroxidase) is added to the wells. Once unbound enzyme is washed away, SureBlue® TMB (tetramethylbenzidine) substrate solution may be added to the wells. The color development may be stopped by the addition of an acidic solution and the optical density measured at 450 nm with wavelength correction set to 630 nm. The assay range may be 30-700 ng/ml.

Noncompartmental analysis may be performed using Phoenix WinNonlin 6.3. Plots may be generated using SigmaPlot v11, and data processing may be performed using Microsoft Excel 2010.

In experiments performed essentially as described in this assay, the PK was measured for Compound E and Compound F after one dose at 1, 10, and 25 mg/kg. For Compound E, terminal half-life, as measured in all three assays, was within the range of 8.96-37.9 h depending on the dose group (Table 9), while the terminal half-life for Compound F was within the range of 18.6-79.5 h depending on the dose group (Table 10). These results from three different binding assays, that each measure different parts of the compound, each demonstrate a higher terminal half-life for Compound F compared to Compound E.

TABLE 9

| | Assay | Dose (mg/kg) | Mean t$_{1/2}$ (n = 2) (h) |
|---|---|---|---|
| Compound E | Ang2 Ag Capt | 1 | 8.96 |
| | | 10 | 24.4 |
| | | 25 | 35.9 |
| | Total Human IgG | 1 | 35.8 |
| | | 10 | 30.2 |
| | | 25 | 36.7 |
| | VEGFR2 Ag Capture | 1 | 15.6 |
| | | 10 | 23.2 |
| | | 25 | 37.9 |

TABLE 10

| | Assay | Dose (mg/kg) | Mean t$_{1/2}$ (n = 2) (h) |
|---|---|---|---|
| Compound F | Ang2 Ag Capt | 1 | 20.1 |
| | | 10 | 54.3 |
| | | 25 | 75.2 |
| | Total Human IgG | 1 | 18.6 |
| | | 10 | 52.6 |
| | | 25 | 79.5 |
| | VEGFR2 Ag Capture | 1 | 27.5 |
| | | 10 | 54.3 |
| | | 25 | 71.2 |

```
                   Amino Acid and Nucleotide Sequences (HCVR of antibody- Compound C)
                                                          SEQ ID NO: 1
EVQLVQSGGGLVKPGGSLRLSCAASGFTFSSYSMNWVRQAPGKGLEWVSAISSS

SSYIYYADSVKGRFTISRDNAKNSLYLQMNSLRAEDTAVYYCARVTEAFDIWGQ

GTLVTVSS (HCVR of antibody- Compound D)
                                                          SEQ ID NO: 2
EVQLVQSGGGLVKPGGSLRLSCAASGFTFSSYSMLWVRQAPGKGLEWVSAISSS

SSYTYYADSVKGRFTISRDNAKNSLYLQMNSLRAEDTAVYYCARVTDAFDIWGQ

GTLVTVSS (HCVR of antibody- Compound E)
                                                          SEQ ID NO: 3
EVQLVQSGGGLVKPGGSLRLSCAASGFTFSSYSMNWVRQAPGKGLEWVSAISSS

SSYIYYADSVKGRFTISRDNAKNSLYLQMNSLRAEDTAVYYCARVTDAFDIWGQ

GTLVTVSS (HCVR of antibody- Compound F)
                                                          SEQ ID NO: 4
EVQLVQSGGGLVKPGGSLRLSCAASGFTFSSYSMLWVRQAPGKGLEWVSAISSS

SSYIYYADSVKGRFTISRDNAKNSLYLQMNSLRAEDTAVYYCARVTDAFDIWGQ

GTLVTVSS (HC of antibody- Compound C)
                                                          SEQ ID NO: 5
EVQLVQSGGGLVKPGGSLRLSCAASGFTFSSYSMNWVRQAPGKGLEWVSAISSS

SSYIYYADSVKGRFTISRDNAKNSLYLQMNSLRAEDTAVYYCARVTEAFDIWGQ
```

| Amino Acid and Nucleotide Sequences |
| --- |

GTLVTVSSASTKGPSVFPLAPCSRSTSESTAALGCLVKDYFPEPVTVSWNSGAL

TSGVHTFPAVLQSSGLYSLSSVVTVPSSSLGTKTYTCNVDHKPSNTKVDKRVES

KYGPPCPPCPAPEAAGGPSVFLFPPKPKDTLMISRTPEVTCVVVDVSQEDPEVQ

FNWYVDGVEVHNAKTKPREEQFNSTYRVVSVLTVLHQDWLNGKEYKCKVSNKGL

PSSIEKTISKAKGQPREPQVYTLPPSQEEMTKNQVSLTCLVKGFYPSDIAVEWE

SNGQPENNYKTTPPVLDSDGSFFLYSRLTVDKSRWQEGNVFSCSVMHEALHNHY

TQKSLSLSLG (HC of antibody- Compound D)
SEQ ID NO: 6

EVQLVQSGGGLVKPGGSLRLSCAASGFTFSSYSMLWVRQAPGKGLEWVSAISSS

SSYTYYADSVKGRFTISRDNAKNSLYLQMNSLRAEDTAVYYCARVTDAFDIWGQ

GTLVTVSSASTKGPSVFPLAPCSRSTSESTAALGCLVKDYFPEPVTVSWNSGAL

TSGVHTFPAVLQSSGLYSLSSVVTVPSSSLGTKTYTCNVDHKPSNTKVDKRVES

KYGPPCPPCPAPEAAGGPSVFLEPPKPKDTLMISRTPEVTCVVVDVSQEDPEVQ

FNWYVDGVEVHNAKTKPREEQFNSTYRVVSVLTVLHQDWLNGKEYKCKVSNKGL

PSSIEKTISKAKGQPREPQVYTLPPSQEEMTKNQVSLTCLVKGFYPSDIAVEWE

SNGQPENNYKTTPPVLDSDGSFFLYSRLTVDKSRWQEGNVFSCSVMHEALHNHY

TQKSLSLSLG (HC of antibody- Compound E)
SEQ ID NO: 7

EVQLVQSGGGLVKPGGSLRLSCAASGFTFSSYSMNWVRQAPGKGLEWVSAISSS

SSYIYYADSVKGRFTISRDNAKNSLYLQMNSLRAEDTAVYYCARVTDAFDIWGQ

GTLVTVSSASTKGPSVFPLAPCSRSTSESTAALGCLVKDYFPEPVTVSWNSGAL

TSGVHTFPAVLQSSGLYSLSSVVTVPSSSLGTKTYTCNVDHKPSNTKVDKRVES

KYGPPCPPCPAPEAAGGPSVFLEPPKPKDTLMISRTPEVTCVVVDVSQEDPEVQ

FNWYVDGVEVHNAKTKPREEQFNSTYRVVSVLTVLHQDWLNGKEYKCKVSNKGL

PSSIEKTISKAKGQPREPQVYTLPPSQEEMTKNQVSLTCLVKGFYPSDIAVEWE

SNGQPENNYKTTPPVLDSDGSFFLYSRLTVDKSRWQEGNVFSCSVMHEALHNHY

TQKSLSLSLG (HC of antibody- Compound F)
SEQ ID NO: 8

EVQLVQSGGGLVKPGGSLRLSCAASGFTFSSYSMLWVRQAPGKGLEWVSAISSS

SSYIYYADSVKGRFTISRDNAKNSLYLQMNSLRAEDTAVYYCARVTDAFDIWGQ

GTLVTVSSASTKGPSVFPLAPCSRSTSESTAALGCLVKDYFPEPVTVSWNSGAL

TSGVHTFPAVLQSSGLYSLSSVVTVPSSSLGTKTYTCNVDHKPSNTKVDKRVES

KYGPPCPPCPAPEAAGGPSVFLEPPKPKDTLMISRTPEVTCVVVDVSQEDPEVQ

FNWYVDGVEVHNAKTKPREEQFNSTYRVVSVLTVLHQDWLNGKEYKCKVSNKGL

PSSIEKTISKAKGQPREPQVYTLPPSQEEMTKNQVSLTCLVKGFYPSDIAVEWE

SNGQPENNYKTTPPVLDSDGSFFLYSRLTVDKSRWQEGNVFSCSVMHEALHNHY

TQKSLSLSLG

| Amino Acid and Nucleotide Sequences |
|---|

(HC of antibody/linker/scFv polypeptide- Compound C)
SEQ ID NO: 9
EVQLVQSGGGLVKPGGSLRLSCAASGFTFSSYSMNWVRQAPGKGLEWVSAISSS

SSYIYYADSVKGRFTISRDNAKNSLYLQMNSLRAEDTAVYYCARVTEAFDIWGQ

GTLVTVSSASTKGPSVFPLAPCSRSTSESTAALGCLVKDYFPEPVTVSWNSGAL

TSGVHTFPAVLQSSGLYSLSSVVTVPSSSLGTKTYTCNVDHKPSNTKVDKRVES

KYGPPCPPCPAPEAAGGPSVFLFPPKPKDTLMISRTPEVTCVVVDVSQEDPEVQ

FNWYVDGVEVHNAKTKPREEQFNSTYRVVSVLTVLHQDWLNGKEYKCKVSNKGL

PSSIEKTISKAKGQPREPQVYTLPPSQEEMTKNQVSLTCLVKGFYPSDIAVEWE

SNGQPENNYKTTPPVLDSDGSFFLYSRLTVDKSRWQEGNVFSCSVMHEALHNHY

TQKSLSLSLGGGGSGGGGSGGGGSQVQLVQSGAEVKKPGASVKVSCKASGYSFT

DYNMVWVRQAPGQCLEWMGYIDPYNGGTGYNQKFEGRVTMTTDTSTSTAYMELR

SLRSDDTAVYYCARTRDRYDVWYFDVWGQGTLVTVSSGGGGSGGGGSGGGGSGG

GGSGGGGSDIQMTQSPSSVSASVGDRVTITCKASQDVYIAVAWYQQKPGKAPKL

LIYWASTRDTGVPSRFSGSGSGTDFTLTISSLQPEDFATYYCHQYSSYPPTFGC

GTKVEIK (HC of antibody/linker/scFv polypeptide- Compound D)
SEQ ID NO: 10
EVQLVQSGGGLVKPGGSLRLSCAASGFTFSSYSMLWVRQAPGKGLEWVSAISSS

SSYTYYADSVKGRFTISRDNAKNSLYLQMNSLRAEDTAVYYCARVTDAFDIWGQ

GTLVTVSSASTKGPSVFPLAPCSRSTSESTAALGCLVKDYFPEPVTVSWNSGAL

TSGVHTFPAVLQSSGLYSLSSVVTVPSSSLGTKTYTCNVDHKPSNTKVDKRVES

KYGPPCPPCPAPEAAGGPSVFLFPPKPKDTLMISRTPEVTCVVVDVSQEDPEVQ

FNWYVDGVEVHNAKTKPREEQFNSTYRVVSVLTVLHQDWLNGKEYKCKVSNKGL

PSSIEKTISKAKGQPREPQVYTLPPSQEEMTKNQVSLTCLVKGFYPSDIAVEWE

SNGQPENNYKTTPPVLDSDGSFFLYSRLTVDKSRWQEGNVFSCSVMHEALHNHY

TQKSLSLSLGGGGSGGGGSGGGGSQVQLVQSGAEVKKPGASVKVSCKASGYSFT

DYNMVWVRQAPGQCLEWMGYIDPYNGGTGYNQKFEGRVTMTTDTSTSTAYMELR

SLRSDDTAVYYCARTRDRYDVWYFDVWGQGTLVTVSSGGGGSGGGGSGGGGSGG

GGSGGGGSDIQMTQSPSSVSASVGDRVTITCKASQDVYIAVAWYQQKPGKAPKL

LIYWASTRDTGVPSRFSGSGSGTDFTLTISSLQPEDFATYYCHQYSSYPPTFGC

GTKVEIK (HC of antibody/linker/scFv polypeptide- Compound E)
SEQ ID NO: 11
EVQLVQSGGGLVKPGGSLRLSCAASGFTFSSYSMNWVRQAPGKGLEWVSAISSS

SSYIYYADSVKGRFTISRDNAKNSLYLQMNSLRAEDTAVYYCARVTDAFDIWGQ

GTLVTVSSASTKGPSVFPLAPCSRSTSESTAALGCLVKDYFPEPVTVSWNSGAL

TSGVHTFPAVLQSSGLYSLSSVVTVPSSSLGTKTYTCNVDHKPSNTKVDKRVES

KYGPPCPPCPAPEAAGGPSVFLFPPKPKDTLMISRTPEVTCVVVDVSQEDPEVQ

FNWYVDGVEVHNAKTKPREEQFNSTYRVVSVLTVLHQDWLNGKEYKCKVSNKGL

PSSIEKTISKAKGQPREPQVYTLPPSQEEMTKNQVSLTCLVKGFYPSDIAVEWE

| Amino Acid and Nucleotide Sequences |
|---|
| SNGQPENNYKTTPPVLDSDGSFFLYSRLTVDKSRWQEGNVFSCSVMHEALHNHY |
| TQKSLSLSLGGGGSGGGGSGGGGSQVQLVQSGAEVKKPGASVKVSCKASGYSFT |
| DYNMVWVRQAPGQCLEWMGYIDPYNGGTGYNQKFEGRVTMTTDTSTSTAYMELR |
| SLRSDDTAVYYCARTRDRYDVWYFDVWGQGTLVTVSSGGGGSGGGGSGGGGSGG |
| GGSGGGGSDIQMTQSPSSVSASVGDRVTITCKASQDVYIAVAWYQQKPGKAPKL |
| LIYWASTRDTGVPSRFSGSGSGTDFTLTISSLQPEDFATYYCHQYSSYPPTFGC |
| GTKVEIK |
| |
| (HC of antibody/linker/scFv polypeptide- Compound F) |
| SEQ ID NO: 12 |
| EVQLVQSGGGLVKPGGSLRLSCAASGFTFSSYSMLWVRQAPGKGLEWVSAISSS |
| SSYIYYADSVKGRFTISRDNAKNSLYLQMNSLRAEDTAVYYCARVTDAFDIWGQ |
| GTLVTVSSASTKGPSVFPLAPCSRSTSESTAALGCLVKDYFPEPVTVSWNSGAL |
| TSGVHTFPAVLQSSGLYSLSSVVTVPSSSLGTKTYTCNVDHKPSNTKVDKRVES |
| KYGPPCPPCPAPEAAGGPSVFLFPPKPKDTLMISRTPEVTCVVVDVSQEDPEVQ |
| FNWYVDGVEVHNAKTKPREEQFNSTYRVVSVLTVLHQDWLNGKEYKCKVSNKGL |
| PSSIEKTISKAKGQPREPQVYTLPPSQEEMTKNQVSLTCLVKGFYPSDIAVEWE |
| SNGQPENNYKTTPPVLDSDGSFFLYSRLTVDKSRWQEGNVFSCSVMHEALHNHY |
| TQKSLSLSLGGGGSGGGGSGGGGSDIVMTQSPDSLAVSLGERATINCKASQDVY |
| IAVAWYQQKPGQPPKLLIYWASTRDTGVPDRFSGSGSGTDFTLTISSLQAEDVA |
| VYYCHQYSSYPPTFGCGTKVEIKGGGGSGGGGSGGGGSGGGGSQVQLVQSGAEV |
| KKPGSSVKVSCKASGYSFTDYNMVWVRQAPGQCLEWMGYIDPYNGGTGYNQKFE |
| GRVTITADESTSTAYMELSSLRSEDTAVYYCARTRDRYDVWYFDVWGQGTLVTV |
| SS |
| |
| (LCVR of antibody- Compound C and Compound F) |
| SEQ ID NO: 13 |
| DIQMTQSPSSVSASVGDRVTITCRASRGIDNWLTWYQQKPGKAPKLLIYEASSL |
| QSGVPSRFSGSGSGTDFTLTISSLQPEDFATYYCQQAKAFPPTFGGGTKVDIK |
| |
| (LCVR of antibody- Compound D) |
| SEQ ID NO: 14 |
| DIQMTQSPSSVSASVGDRVTITCRASQGIDNWLTWYQQKPGKAPKLLIVEASSL |
| QSGVPSRFSGSGSGTDFTLTISSLQPEDFATYYCQQAKRFPPTFGGGTKVDIK |
| |
| (LCVR of antibody- Compound E) |
| SEQ ID NO: 15 |
| DIQMTQSPSSVSASVGDRVTITCRASQGIDNWLTWYQQKPGKAPKLLIVEASSL |
| QSGVPSRFSGSGSGTDFTLTISSLQPEDFATYYCQQAKAFPPTFGGGTKVDIK |
| |
| (LC of antibody- Compound C and Compound F) |
| SEQ ID NO: 16 |
| DIQMTQSPSSVSASVGDRVTITCRASRGIDNWLTWYQQKPGKAPKLLIYEASSL |
| QSGVPSRFSGSGSGTDFTLTISSLQPEDFATYYCQQAKAFPPTFGGGTKVDIKR |
| TVAAPSVFIFPPSDEQLKSGTASVVCLLNNFYPREAKVQWKVDNALQSGNSQES |
| VTEQDSKDSTYSLSSTLTLSKADYEKHKVYACEVTHQGLSSPVTKSFNRGEC |
| |
| (LC of antibody- Compound D) |
| SEQ ID NO: 17 |
| DIQMTQSPSSVSASVGDRVTITCRASQGIDNWLTWYQQKPGKAPKLLIVEASSL |
| QSGVPSRFSGSGSGTDFTLTISSLQPEDFATYYCQQAKRFPPTFGGGTKVDIKR |

| Amino Acid and Nucleotide Sequences |
|---|

TVAAPSVFIFPPSDEQLKSGTASVVCLLNNFYPREAKVQWKVDNALQSGNSQES

VTEQDSKDSTYSLSSTLTLSKADYEKHKVYACEVTHQGLSSPVTKSFNRGEC (LC of antibody- Compound E)
SEQ ID NO: 18
DIQMTQSPSSVSASVGDRVTITCRASQGIDNWLTWYQQKPGKAPKLLIVEASSL

QSGVPSRFSGSGSGTDFTLTISSLQPEDFATYYCQQAKAFPPTFGGGTKVDIKR

TVAAPSVFIFPPSDEQLKSGTASVVCLLNNFYPREAKVQWKVDNALQSGNSQES

VTEQDSKDSTYSLSSTLTLSKADYEKHKVYACEVTHQGLSSPVTKSFNRGEC (scFv polypeptide- Compound C, Compound D, Compound E)
SEQ ID NO: 19
QVQLVQSGAEVKKPGASVKVSCKASGYSFTDYNMVWVRQAPGQCLEWMGYIDPY

NGGTGYNQKFEGRVTMTTDTSTSTAYMELRSLRSDDTAVYYCARTRDRYDVWYF

DVWGQGTLVTVSSGGGGSGGGGSGGGGSGGGGSGGGGSDIQMTQSPSSVSASVG

DRVTITCKASQDVYIAVAWYQQKPGKAPKLLIYWASTRDTGVPSRFSGSGSGTD

FTLTISSLQPEDFATYYCHQYSSYPPTFGCGTKVEIK (scFv polypeptide- Compound F)
SEQ ID NO: 20
DIVMTQSPDSLAVSLGERATINCKASQDVYIAVAWYQQKPGQPPKLLIYWASTR

DTGVPDRFSGSGSGTDFTLTISSLQAEDVAVYYCHQYSSYPPTFGCGTKVEIKG

GGGSGGGGSGGGGSGGGGSQVQLVQSGAEVKKPGSSVKVSCKASGYSFTDYNMV

WVRQAPGQCLEWMGYIDPYNGGTGYNQKFEGRVTITADESTSTAYMELSSLRSE

DTAVYYCARTRDRYDVWYFDVWGQGTLVTVSS (HCVR of scFv polypeptide- Compound C, Compound D,
Compound E)
SEQ ID NO: 21
QVQLVQSGAEVKKPGASVKVSCKASGYSFTDYNMVWVRQAPGQCLEWMGYIDPY

NGGTGYNQKFEGRVTMTTDTSTSTAYMELRSLRSDDTAVYYCARTRDRYDVWYF

DVWGQGTLVTVSS (HCVR of scFv polypeptide- Compound F)
SEQ ID NO: 22
QVQLVQSGAEVKKPGSSVKVSCKASGYSFTDYNMVWVRQAPGQCLEWMGYIDPY

NGGTGYNQKFEGRVTITADESTSTAYMELSSLRSEDTAVYYCARTRDRYDVWYF

DVWGQGTLVTVSS (LCVR of scFv polypeptide- Compound C, Compound D,
Compound E)
SEQ ID NO: 23
DIQMTQSPSSVSASVGDRVTITCKASQDVYIAVAWYQQKPGKAPKLLIYWASTR

DTGVPSRFSGSGSGTDFTLTISSLQPEDFATYYCHQYSSYPPTFGCGTKVEIK (LCVR of scFv polypeptide- Compound F)
SEQ ID NO: 24
DIVMTQSPDSLAVSLGERATINCKASQDVYIAVAWYQQKPGQPPKLLIYWASTR

DTGVPDRFSGSGSGTDFTLTISSLQAEDVAVYYCHQYSSYPPTFGCGTKVEIK (DNA of HC of antibody/linker/scFv polypeptide-
Compound C)
SEQ ID NO: 25
GAGGTCCAGCTGGTGCAGTCTGGGGGAGGCCTGGTCAAGCCTGGGGGGTCCCTG

AGACTCTCCTGTGCAGCCTCTGGATTCACCTTCAGTAGCTATAGCATGAACTGG

GTCCGCCAGGCTCCAGGGAAGGGGCTGGAGTGGGTCTCAGCCATTAGTAGTAGT

| Amino Acid and Nucleotide Sequences |
|---|
| AGTAGTTACATATACTACGCAGACTCAGTGAAGGGCCGATTCACCATCTCCAGA |
| GACAACGCCAAGAACTCACTGTATCTGCAAATGAACAGCCTGAGAGCCGAGGAC |
| ACGGCTGTGTATTACTGTGCGAGAGTCACAGAGGCTTTTGATATCTGGGGCCAA |
| GGGACACTGGTCACCGTCTCAAGCGCCTCCACCAAGGGCCCATCGGTCTTCCCG |
| CTAGCGCCCTGCTCCAGGAGCACCTCCGAGAGCACAGCCGCCCTGGGCTGCCTG |
| GTCAAGGACTACTTCCCCGAACCGGTGACGGTGTCGTGGAACTCAGGCGCCCTG |
| ACCAGCGGCGTGCACACCTTCCCGGCTGTCCTACAGTCCTCAGGACTCTACTCC |
| CTCAGCAGCGTGGTGACCGTGCCCTCCAGCAGCTTGGGCACGAAGACCTACACC |
| TGCAACGTAGATCACAAGCCCAGCAACACCAAGGTGGACAAGAGAGTTGAGTCC |
| AAATATGGTCCCCCATGCCCACCCTGCCCAGCACCTGAGGCCGCCGGGGGACCA |
| TCAGTCTTCCTGTTCCCCCAAAACCCAAGGACACTCTCATGATCTCCCGGACC |
| CCTGAGGTCACGTGCGTGGTGGTGGACGTGAGCCAGGAAGACCCCGAGGTCCAG |
| TTCAACTGGTACGTGGATGGCGTGGAGGTGCATAATGCCAAGACAAAGCCGCGG |
| GAGGAGCAGTTCAACAGCACGTACCGTGTGGTCAGCGTCCTCACCGTCCTGCAC |
| CAGGACTGGCTGAACGGCAAGGAGTACAAGTGCAAGGTCTCCAACAAAGGCCTC |
| CCGTCCTCCATCGAGAAAACCATCTCCAAAGCCAAAGGGCAGCCCCGAGAGCCA |
| CAGGTGTACACCCTGCCCCCATCCCAGGAGGAGATGACCAAGAACCAGGTCAGC |
| CTGACCTGCCTGGTCAAAGGCTTCTACCCCAGCGACATCGCCGTGGAGTGGGAA |
| AGCAATGGGCAGCCGGAGAACAACTACAAGACCACGCCTCCCGTGCTGGACTCC |
| GACGGCTCCTTCTTCCTCTACAGCAGGCTAACCGTGGACAAGAGCAGGTGGCAG |
| GAGGGGAATGTCTTCTCATGCTCCGTGATGCATGAGGCTCTGCACAACCACTAC |
| ACACAGAAGAGCCTCTCCCTGTCTCTGGGTGGCGGAGGCTCCGGGGAGGGGGT |
| AGCGGAGGAGGGGGATCCCAGGTTCAGCTGGTGCAGTCTGGAGCTGAGGTGAAG |
| AAGCCTGGGGCCTCAGTGAAGGTCTCCTGCAAGGCTTCTGGTTACTCATTCACT |
| GACTACAACATGGTGTGGGTGCGACAGGCCCCTGGACAATGCCTTGAGTGGATG |
| GGATATATTGATCCTTACAATGGTGGTACTGGCTACAACCAGAAGTTCGAGGGC |
| AGAGTCACCATGACCACAGACACATCCACGAGCACAGCCTACATGGAGCTGAGG |
| AGCCTGAGATCTGACGACACGGCCGTGTATTACTGTGCGAGAACGAGGGATAGA |
| TACGACGTCTGGTACTTCGATGTCTGGGGCCAGGGAACCCTGGTCACCGTCTCC |
| TCAGGAGGCGGAGGTTCCGGGGGAGGGGGCAGCGGAGGAGGCGGATCGGGCGGA |
| GGAGGAAGTGGAGGCGGAGGCAGCGACATCCAGATGACCCAGTCTCCATCTTCC |
| GTGTCTGCATCTGTTGGCGACAGAGTCACCATCACTTGTAAGGCCAGTCAGGAT |
| GTGTATATTGCTGTAGCCTGGTATCAGCAGAAACCAGGGAAAGCCCCTAAGCTC |
| CTGATCTATTGGGCATCCACCCGGGACACTGGGGTCCCATCAAGGTTCAGCGGC |
| AGTGGATCTGGGACAGATTTCACTCTCACCATCAGCAGCCTGCAGCCTGAAGAT |
| TTTGCAACTTACTATTGTCACCAATATAGCAGCTATCCTCCTACGTTCGGCTGC |
| GGGACCAAGGTGGAGATCAAA |

| Amino Acid and Nucleotide Sequences |
| --- |

(DNA of LC of antibody- Compound C and Compound F)

SEQ ID NO: 26

GACATCCAGATGACCCAGTCTCCATCTTCTGTGTCTGCATCTGTAGGAGACAGA

GTCACCATCACTTGTCGGGCGAGTCGTGGTATTGACAACTGGTTAACGTGGTAT

CAGCAGAAACCAGGGAAAGCCCCTAAGCTCCTGATTTACGAAGCATCCAGTTTG

CAATCAGGGGTCCCATCAAGGTTCAGCGGCAGTGGATCTGGGACAGATTTCACT

CTCACTATCAGCAGCCTGCAGCCTGAAGATTTTGCAACTTACTATTGTCAACAA

GCTAAGGCTTTTCCTCCCACTTTCGGCGGAGGGACCAAGGTGGACATCAAACGA

ACTGTGGCTGCACCATCTGTCTTCATCTTCCCGCCATCTGATGAGCAGTTGAAA

TCTGGAACTGCCTCTGTTGTGTGCCTGCTGAATAACTTCTATCCCAGAGAGGCC

AAAGTACAGTGGAAGGTGGATAACGCCCTCCAATCGGGTAACTCCCAGGAGAGT

GTCACAGAGCAGGACAGCAAGGACAGCACCTACAGCCTCAGCAGCACCCTGACG

CTGAGCAAAGCAGACTACGAGAAACACAAAGTCTACGCCTGCGAAGTCACCCAT

CAGGGCCTGAGCTCGCCCGTCACAAAGAGCTTCAACAGGGGAGAGTGC (DNA of HC of antibody/linker/scFv polypeptide-
Compound D)

SEQ ID NO: 27

GAGGTCCAGCTGGTGCAGTCTGGGGGAGGCCTGGTCAAGCCTGGGGGGTCCCTG

AGACTCTCCTGTGCAGCCTCTGGATTCACCTTCAGTAGCTATAGCATGCTTTGG

GTCCGCCAGGCTCCAGGGAAGGGGCTGGAGTGGGTCTCAGCCATTAGTAGTAGT

AGTAGTTACACCTACTACGCAGACTCAGTGAAGGGCCGATTCACCATCTCCAGA

GACAACGCCAAGAACTCACTGTATCTGCAAATGAACAGCCTGAGAGCCGAGGAC

ACGGCTGTGTATTACTGTGCGAGAGTCACAGATGCTTTTGATATCTGGGGCCAA

GGGACACTGGTCACCGTCTCAAGCGCCTCCACCAAGGGCCCATCGGTCTTCCCG

CTAGCGCCCTGCTCCAGGAGCACCTCCGAGAGCACAGCCGCCCTGGGCTGCCTG

GTCAAGGACTACTTCCCCGAACCGGTGACGGTGTCGTGGAACTCAGGCGCCCTG

ACCAGCGGCGTGCACACCTTCCCGGCTGTCCTACAGTCCTCAGGACTCTACTCC

CTCAGCAGCGTGGTGACCGTGCCCTCCAGCAGCTTGGGCACGAAGACCTACACC

TGCAACGTAGATCACAAGCCCAGCAACACCAAGGTGGACAAGAGAGTTGAGTCC

AAATATGGTCCCCCATGCCCACCCTGCCCAGCACCTGAGGCCGCCGGGGGACCA

TCAGTCTTCCTGTTCCCCCCAAAACCCAAGGACACTCTCATGATCTCCCGGACC

CCTGAGGTCACGTGCGTGGTGGTGGACGTGAGCCAGGAAGACCCCGAGGTCCAG

TTCAACTGGTACGTGGATGGCGTGGAGGTGCATAATGCCAAGACAAAGCCGCGG

GAGGAGCAGTTCAACAGCACGTACCGTGTGGTCAGCGTCCTCACCGTCCTGCAC

CAGGACTGGCTGAACGGCAAGGAGTACAAGTGCAAGGTCTCCAACAAAGGCCTC

CCGTCCTCCATCGAGAAAACCATCTCCAAAGCCAAAGGGCAGCCCCGAGAGCCA

CAGGTGTACACCCTGCCCCCATCCCAGGAGGAGATGACCAAGAACCAGGTCAGC

CTGACCTGCCTGGTCAAAGGCTTCTACCCCAGCGACATCGCCGTGGAGTGGGAA

AGCAATGGGCAGCCGGAGAACAACTACAAGACCACGCCTCCCGTGCTGGACTCC

GACGGCTCCTTCTTCCTCTACAGCAGGCTAACCGTGGACAAGAGCAGGTGGCAG

GAGGGGAATGTCTTCTCATGCTCCGTGATGCATGAGGCTCTGCACAACCACTAC

| Amino Acid and Nucleotide Sequences |
|---|
| ACACAGAAGAGCCTCTCCCTGTCTCTGGGTGGCGGAGGCTCCGGGGAGGGGGT |
| AGCGGAGGAGGGGGATCCCAGGTTCAGCTGGTGCAGTCTGGAGCTGAGGTGAAG |
| AAGCCTGGGGCCTCAGTGAAGGTCTCCTGCAAGGCTTCTGGTTACTCATTCACT |
| GACTACAACATGGTGTGGGTGCGACAGGCCCCTGGACAATGCCTTGAGTGGATG |
| GGATATATTGATCCTTACAATGGTGGTACTGGCTACAACCAGAAGTTCGAGGGC |
| AGAGTCACCATGACCACAGACACATCCACGAGCACAGCCTACATGGAGCTGAGG |
| AGCCTGAGATCTGACGACACGGCCGTGTATTACTGTGCGAGAACGAGGGATAGA |
| TACGACGTCTGGTACTTCGATGTCTGGGGCCAGGGAACCCTGGTCACCGTCTCC |
| TCAGGAGGCGGAGGTTCCGGGGGAGGGGGCAGCGGAGGAGGCGGATCGGGCGGA |
| GGAGGAAGTGGAGGCGGAGGCAGCGACATCCAGATGACCCAGTCTCCATCTTCC |
| GTGTCTGCATCTGTTGGCGACAGAGTCACCATCACTTGTAAGGCCAGTCAGGAT |
| GTGTATATTGCTGTAGCCTGGTATCAGCAGAAACCAGGGAAAGCCCCTAAGCTC |
| CTGATCTATTGGGCATCCACCCGGGACACTGGGGTCCCATCAAGGTTCAGCGGC |
| AGTGGATCTGGGACAGATTTCACTCTCACCATCAGCAGCCTGCAGCCTGAAGAT |
| TTTGCAACTTACTATTGTCACCAATATAGCAGCTATCCTCCTACGTTCGGCTGC |
| GGGACCAAGGTGGAGATCAAA |

(DNA of LC of antibody- Compound D)
SEQ ID NO: 28

GACATCCAGATGACCCAGTCTCCATCTTCTGTGTCTGCATCTGTAGGAGACAGA
GTCACCATCACTTGTCGGGCGAGTCAGGGTATTGACAACTGGTTAACGTGGTAT
CAGCAGAAACCAGGGAAAGCCCCTAAGCTCCTGATCGTCGAGGCATCCAGTTTG
CAATCAGGGGTCCCATCAAGGTTCAGCGGCAGTGGATCTGGGACAGATTTCACT
CTCACTATCAGCAGCCTGCAGCCTGAAGATTTTGCAACTTACTATTGTCAACAG
GCTAAGAGGTTTCCTCCCACTTTCGGCGGAGGGACCAAGGTGGACATCAAACGA
ACTGTGGCTGCACCATCTGTCTTCATCTTCCCGCCATCTGATGAGCAGTTGAAA
TCTGGAACTGCCTCTGTTGTGTGCCTGCTGAATAACTTCTATCCCAGAGAGGCC
AAAGTACAGTGGAAGGTGGATAACGCCCTCCAATCGGGTAACTCCCAGGAGAGT
GTCACAGAGCAGGACAGCAAGGACAGCACCTACAGCCTCAGCAGCACCCTGACG
CTGAGCAAAGCAGACTACGAGAAACACAAAGTCTACGCCTGCGAAGTCACCCAT
CAGGGCCTGAGCTCGCCCGTCACAAAGAGCTTCAACAGGGGAGAGTGC (DNA of HC of antibody/linker/scFv polypeptide-
Compound E)
SEQ ID NO: 29

GAGGTCCAGCTGGTGCAGTCTGGGGGAGGCCTGGTCAAGCCTGGGGGGTCCCTG
AGACTCTCCTGTGCAGCCTCTGGATTCACCTTCAGTAGCTATAGCATGAACTGG
GTCCGCCAGGCTCCAGGGAAGGGGCTGGAGTGGGTCTCAGCGATTAGTAGTAGT
AGTAGTTACATATACTACGCAGACTCAGTGAAGGGCCGATTCACCATCTCCAGA
GACAACGCCAAGAACTCACTGTATCTGCAAATGAACAGCCTGAGAGCCGAGGAC
ACGGCTGTGTATTACTGTGCGAGAGTCACAGATGCTTTTGATATCTGGGGCCAA
GGGACACTGGTCACCGTCTCAAGCGCCTCCACCAAGGGCCCATCGGTCTTCCCG
CTAGCGCCCTGCTCCAGGAGCACCTCCGAGAGCACAGCCGCCCTGGGCTGCCTG

| Amino Acid and Nucleotide Sequences |
|---|
| GTCAAGGACTACTTCCCCGAACCGGTGACGGTGTCGTGGAACTCAGGCGCCCTG |
| ACCAGCGGCGTGCACACCTTCCCGGCTGTCCTACAGTCCTCAGGACTCTACTCC |
| CTCAGCAGCGTGGTGACCGTGCCCTCCAGCAGCTTGGGCACGAAGACCTACACC |
| TGCAACGTAGATCACAAGCCCAGCAACACCAAGGTGGACAAGAGAGTTGAGTCC |
| AAATATGGTCCCCCATGCCCACCCTGCCCAGCACCTGAGGCCGCCGGGGGACCA |
| TCAGTCTTCCTGTTCCCCCCAAAACCCAAGGACACTCTCATGATCTCCCGGACC |
| CCTGAGGTCACGTGCGTGGTGGTGGACGTGAGCCAGGAAGACCCCGAGGTCCAG |
| TTCAACTGGTACGTGGATGGCGTGGAGGTGCATAATGCCAAGACAAAGCCGCGG |
| GAGGAGCAGTTCAACAGCACGTACCGTGTGGTCAGCGTCCTCACCGTCCTGCAC |
| CAGGACTGGCTGAACGGCAAGGAGTACAAGTGCAAGGTCTCCAACAAAGGCCTC |
| CCGTCCTCCATCGAGAAAACCATCTCCAAAGCCAAAGGGCAGCCCCGAGAGCCA |
| CAGGTGTACACCCTGCCCCCATCCCAGGAGGAGATGACCAAGAACCAGGTCAGC |
| CTGACCTGCCTGGTCAAAGGCTTCTACCCCAGCGACATCGCCGTGGAGTGGGAA |
| AGCAATGGGCAGCCGGAGAACAACTACAAGACCACGCCTCCCGTGCTGGACTCC |
| GACGGCTCCTTCTTCCTCTACAGCAGGCTAACCGTGGACAAGAGCAGGTGGCAG |
| GAGGGGAATGTCTTCTCATGCTCCGTGATGCATGAGGCTCTGCACAACCACTAC |
| ACACAGAAGAGCCTCTCCCTGTCTCTGGGTGGCGGAGGCTCCGGGGGAGGGGGT |
| AGCGGAGGAGGGGGATCCCAGGTTCAGCTGGTGCAGTCTGGAGCTGAGGTGAAG |
| AAGCCTGGGGCCTCAGTGAAGGTCTCCTGCAAGGCTTCTGGTTACTCATTCACT |
| GACTACAACATGGTGTGGGTGCGACAGGCCCCTGGACAATGCCTTGAGTGGATG |
| GGATATATTGATCCTTACAATGGTGGTACTGGCTACAACCAGAAGTTCGAGGGC |
| AGAGTCACCATGACCACAGACACATCCACGAGCACAGCCTACATGGAGCTGAGG |
| AGCCTGAGATCTGACGACACGGCCGTGTATTACTGTGCGAGAACGAGGGATAGA |
| TACGACGTCTGGTACTTCGATGTCTGGGGCCAGGGAACCCTGGTCACCGTCTCC |
| TCAGGAGGCGGAGGTTCCGGGGGAGGGGGCAGCGGAGGAGGCGGATCGGGCGGA |
| GGAGGAAGTGGAGGCGGAGGCAGCGACATCCAGATGACCCAGTCTCCATCTTCC |
| GTGTCTGCATCTGTTGGCGACAGAGTCACCATCACTTGTAAGGCCAGTCAGGAT |
| GTGTATATTGCTGTAGCCTGGTATCAGCAGAAACCAGGGAAAGCCCCTAAGCTC |
| CTGATCTATTGGGCATCCACCCGGGACACTGGGGTCCCATCAAGGTTCAGCGGC |
| AGTGGATCTGGGACAGATTTCACTCTCACCATCAGCAGCCTGCAGCCTGAAGAT |
| TTTGCAACTTACTATTGTCACCAATATAGCAGCTATCCTCCTACGTTCGGCTGC |
| GGGACCAAGGTGGAGATCAAA |
| (DNA of LC of antibody- Compound E) |
| SEQ ID NO: 30 |
| GACATCCAGATGACCCAGTCTCCATCTTCTGTGTCTGCATCTGTAGGAGACAGA |
| GTCACCATCACTTGTCGGGCGAGTCAGGGTATTGACAACTGGTTAACGTGGTAT |
| CAGCAGAAACCAGGGAAAGCCCCTAAGCTCCTGATCGTCGAGGCATCCAGTTTG |
| CAATCAGGGGTCCCATCAAGGTTCAGCGGCAGTGGATCTGGGACAGATTTCACT |
| CTCACTATCAGCAGCCTGCAGCCTGAAGATTTTGCAACTTACTATTGTCAACAG |

| Amino Acid and Nucleotide Sequences |
| --- |
| GCTAAGGCTTTTCCTCCCACTTTCGGCGGAGGGACCAAGGTGGACATCAAACGA |
| ACTGTGGCTGCACCATCTGTCTTCATCTTCCCGCCATCTGATGAGCAGTTGAAA |
| TCTGGAACTGCCTCTGTTGTGTGCCTGCTGAATAACTTCTATCCCAGAGAGGCC |
| AAAGTACAGTGGAAGGTGGATAACGCCCTCCAATCGGGTAACTCCCAGGAGAGT |
| GTCACAGAGCAGGACAGCAAGGACAGCACCTACAGCCTCAGCAGCACCCTGACG |
| CTGAGCAAAGCAGACTACGAGAAACACAAAGTCTACGCCTGCGAAGTCACCCAT |
| CAGGGCCTGAGCTCGCCCGTCACAAAGAGCTTCAACAGGGGAGAGTGC |
| (DNA of HC of antibody/linker/scFv polypeptide-Compound F) SEQ ID NO: 31 |
| GAGGTCCAGCTGGTGCAGTCTGGGGGAGGCCTGGTCAAGCCTGGGGGGTCCCTG |
| AGACTCTCCTGTGCAGCCTCTGGATTCACCTTCAGTAGCTATAGCATGCTTTGG |
| GTCCGCCAGGCTCCAGGGAAGGGGCTGGAGTGGGTCTCAGCCATTAGTAGTAGT |
| AGTAGTTACATATACTACGCAGACTCAGTGAAGGGCCGATTCACCATCTCCAGA |
| GACAACGCCAAGAACTCACTGTATCTGCAAATGAACAGCCTGAGAGCCGAGGAC |
| ACGGCTGTGTATTACTGTGCGAGAGTCACAGATGCTTTTGATATCTGGGGCCAA |
| GGGACACTGGTCACCGTCTCAAGCGCCTCCACCAAGGGCCCATCGGTCTTCCCG |
| CTAGCGCCCTGCTCCAGGAGCACCTCCGAGAGCACAGCCGCCCTGGGCTGCCTG |
| GTCAAGGACTACTTCCCCGAACCGGTGACGGTGTCGTGGAACTCAGGCGCCCTG |
| ACCAGCGGCGTGCACACCTTCCCGGCTGTCCTACAGTCCTCAGGACTCTACTCC |
| CTCAGCAGCGTGGTGACCGTGCCCTCCAGCAGCTTGGGCACGAAGACCTACACC |
| TGCAACGTAGATCACAAGCCCAGCAACACCAAGGTGGACAAGAGAGTTGAGTCC |
| AAATATGGTCCCCCATGCCCACCCTGCCCAGCACCTGAGGCCGCCGGGGGACCA |
| TCAGTCTTCCTGTTCCCCCCAAAACCCAAGGACACTCTCATGATCTCCCGGACC |
| CCTGAGGTCACGTGCGTGGTGGTGGACGTGAGCCAGGAAGACCCCGAGGTCCAG |
| TTCAACTGGTACGTGGATGGCGTGGAGGTGCATAATGCCAAGACAAAGCCGCGG |
| GAGGAGCAGTTCAACAGCACGTACCGTGTGGTCAGCGTCCTCACCGTCCTGCAC |
| CAGGACTGGCTGAACGGCAAGGAGTACAAGTGCAAGGTCTCCAACAAAGGCCTC |
| CCGTCCTCCATCGAGAAAACCATCTCCAAAGCCAAAGGGCAGCCCCGAGAGCCA |
| CAGGTGTACACCCTGCCCCCATCCCAGGAGGAGATGACCAAGAACCAGGTCAGC |
| CTGACCTGCCTGGTCAAAGGCTTCTACCCCAGCGACATCGCCGTGGAGTGGGAA |
| AGCAATGGGCAGCCGGAGAACAACTACAAGACCACGCCTCCCGTGCTGGACTCC |
| GACGGCTCCTTCTTCCTCTACAGCAGGCTAACCGTGGACAAGAGCAGGTGGCAG |
| GAGGGGAATGTCTTCTCATGCTCCGTGATGCATGAGGCTCTGCACAACCACTAC |
| ACACAGAAGAGCCTCTCCCTGTCTCTGGGTGGCGGAGGCTCCGGGGAGGGGGT |
| AGCGGAGGAGGGGGATCCGACATCGTGATGACCCAGTCTCCAGACTCCCTGGCT |
| GTGTCTCTGGGCGAGAGGGCCACCATCAACTGCAAGGCCAGTCAGGATGTGTAT |
| ATTGCTGTAGCCTGGTACCAGCAGAAACCAGGACAGCCTCCTAAGCTGCTCATT |
| TACTGGGCATCCACCCGGGACACTGGGGTCCCTGACCGATTCAGTGGCAGCGGG |
| TCTGGGACAGATTTCACTCTCACCATCAGCAGCCTGCAGGCTGAAGATGTGGCA |

| Amino Acid and Nucleotide Sequences |
|---|
| GTTTATTACTGTCACCAATATAGCAGCTATCCTCCTACGTTCGGCTGCGGGACC |
| AAGGTGGAGATCAAAGGTGGCGGAGGATCTGGTGGAGGTGGCTCAGGAGGTGGC |
| GGAAGCGGCGGAGGTGGAAGTCAGGTGCAGCTGGTGCAGTCTGGGGCTGAGGTG |
| AAGAAGCCTGGGTCCTCGGTGAAGGTCTCCTGCAAGGCTTCTGGTTACTCATTC |
| ACTGACTACAACATGGTGTGGGTGCGACAGGCCCCTGGACAATGCCTTGAGTGG |
| ATGGGATATATTGATCCTTACAATGGTGGTACTGGCTACAACCAGAAGTTCGAG |
| GGCAGAGTCACGATTACCGCGGACGAATCCACGAGCACAGCCTACATGGAGCTG |
| AGCAGCCTGAGATCTGAGGACACGGCCGTGTATTACTGTGCGAGAACGAGGGAT |
| AGGTACGACGTCTGGTACTTCGATGTCTGGGGCCAGGGAACCCTGGTCACCGTC |
| TCCTCA |

(human VEGFR2 ECD)                                          SEQ ID NO: 32
ASVGLPSVSLDLPRLSIQKDILTIKANTTLQITCRGQRDLDWLWPNNQSGSEQR
VEVTECSDGLFCKTLTIPKVIGNDTGAYKCFYRETDLASVIYVYVQDYRSPFIA
SVSDQHGVVYITENKNKTVVIPCLGSISNLNVSLCARYPEKRFVPDGNRISWDS
KKGFTIPSYMISYAGMVFCEAKINDESYQSIMYIVVVVGYRIYDVVLSPSHGIE
LSVGEKLVLNCTARTELNVGIDFNWEYPSSKHQHKKLVNRDLKTQSGSEMKKFL
STLTIDGVTRSDQGLYTCAASSGLMTKKNSTFVRVHEKPFVAFGSGMESLVEAT
VGERVRIPAKYLGYPPPEIKWYKNGIPLESNHTIKAGHVLTIMEVSERDTGNYT
VILTNPISKEKQSHVVSLVVYVPPQIGEKSLISPVDSYQYGTTQTLTCTVYAIP
PPHHIHWYWQLEEECANEPSQAVSVTNPYPCEEWRSVEDFQGGNKIEVNKNQFA
LIEGKNKTVSTLVIQAANVSALYKCEAVNKVGRGERVISFHVTRGPEITLQPDM
QPTEQESVSLWCTADRSTFENLTWYKLGPQPLPIHVGELPTPVCKNLDTLWKLN
ATMFSNSTNDILIMELKNASLQDQGDYVCLAQDRTKKRHCVVRQLTVLERVAP
TITGNLENQTTSIGESIEVSCTASGNPPPQIMWFKDNETLVEDSGIVLKDGNRN
LTIRRVRKEDEGLYTCQACSVLGCAKVEAFFIIEGAQEKTNLE (human Ang2)                                                SEQ ID NO: 33
YNNFRKSMDSIGKKQYQVQHGSCSYTFLLPEMDNCRSSSSPYVSNAVQRDAPLE
YDDSVQRLQVLENIMENNTQWLMKLENYIQDNMKKEMVEIQQNAVQNQTAVMIE
IGTNLLNQTAEQTRKLTDVEAQVLNQTTRLELQLLEHSLSTNKLEKQILDQTSE
INKLQDKNSFLEKKVLAMEDKHIIQLQSIKEEKDQLQVLVSKQNSIIEELEKKI
VTATVNNSVLQKQQHDLMETVNNLLTMMSTSNSAKDPTVAKEEQISFRDCAEVF
KSGHTTNGIYTLTFPNSTEEIKAYCDMEAGGGWTHQRREDGSVDFQRTWKEYK
VGFGNPSGEYWLGNEFVSQLTNQQRYVLKIHLKDWEGNEAYSLYEHFYLSSEEL
NYRIHLKGLTGTAGKISSISQPGNDFSTKDGNDKCICKCSQMLTGGWWFDACG
PSNLNGMYYPQRQNTNKFNGIKWYYWKGSGYSLKATTMMIRPADF

SEQ ID NO: 34
GGGGSGGGGS

SEQ ID NO: 35
GGGGSGGGGSGGGGS

Amino Acid and Nucleotide Sequences

SEQ ID NO: 36
GGGGSGGGGSGGGGSGGGGS

SEQ ID NO: 37
GGGGSGGGGSGGGGSGGGGSGGGGS (HC of antibody/linker/scFv polypeptide- Compound A)
SEQ ID NO: 38
EVQLVQSGGGLVKPGGSLRLSCAASGFTFSSYSMNWVRQAPGKGLEWVSSISSS
SSYIYYADSVKGRFTISRDNAKNSLYLQMNSLRAEDTAVYYCARVTDAFDIWGQ
GTMVTVSSASTKGPSVFPLAPSSKSTSGGTAALGCLVKDYFPEPVTVSWNSGAL
TSGVHTFPAVLQSSGLYSLSSVVTVPSSSLGTQTYICNVNHKPSNTKVDKRVEP
KSCDKTHTCPPCPAPELLGGPSVFLFPPKPKDTLMISRTPEVTCVVVDVSHEDP
EVKFNWYVDGVEVHNAKTKPREEQYNSTYRVVSVLTVLHQDWLNGKEYKCKVSN
KALPAPIEKTISKAKGQPREPQVYTLPPSREEMTKNQVSLTCLVKGFYPSDIAV
EWESNGQPENNYKTTPPVLDSDGSFFLYSKLTVDKSRWQQGNVFSCSVMHEALH
NHYTQKSLSLSPGGGGSGGGGSGGGGSQVQLVQSGAEVKKPGASVKVSCKASGY
SFTDYNMVWVRQAPGQCLEWMGYIDPYNGGTYNQKFEGRVTMTTDTSTSTAYM
ELRSLRSDDTAVYYCARTRDRYDVWYFDVWGQGTLVTVSSGGGGSGGGGSGGGG
SGGGGSGGGGSDIQMTQSPSSVSASVGDRVTITCKASQDVYIAVAWYQQKPGKA
PKLLIYWASTRDTGVPSRFSGSGSGTDFTLTISSLQPEDFATYYCHQYSSYPPT
FGCGTKVEIK (LC of antibody- Compound A and Compound B)
SEQ ID NO: 39
DIQMTQSPSSVSASIGDRVTITCRASQGIDNWLGWYQQKPGKAPKLLIYDASNL
DTGVPSRFSGSGSGTYFTLTISSLQAEDFAVYFCQQAKAFPPTFGGGTKVDIKR
TVAAPSVFIFPPSDEQLKSGTASVVCLLNNFYPREAKVQWKVDNALQSGNSQES
VTEQDSKDSTYSLSSTLTLSKADYEKHKVYACEVTHQGLSSPVTKSFNRGEC (HC of antibody/linker/scFv polypeptide- Compound B)
SEQ ID NO: 40
EVQLVQSGGGLVKPGGSLRLSCAASGFTFSSYSMNWVRQAPGKGLEWVSSISSS
SSYIYYADSVKGRFTISRDNAKNSLYLQMNSLRAEDTAVYYCARVTDAFDIWGQ
GTMVTVSSASTKGPSVFPLAPCSRSTSESTAALGCLVKDYFPEPVTVSWNSGAL
TSGVHTFPAVLQSSGLYSLSSVVTVPSSSLGTKTYTCNVDHKPSNTKVDKRVES
KYGPPCPPCPAPEAAGGPSVFLFPPKPKDTLMISRTPEVTCVVVDVSQEDPEVQ
FNWYVDGVEVHNAKTKPREEQFNSTYRVVSVLTVLHQDWLNGKEYKCKVSNKGL
PSSIEKTISKAKGQPREPQVYTLPPSQEEMTKNQVSLTCLVKGFYPSDIAVEWE
SNGQPENNYKTTPPVLDSDGSFFLYSRLTVDKSRWQEGNVFSCSVMHEALHNHY
TQKSLSLSLGGGGSGGGGSGGGGSQVQLVQSGAEVKKPGASVKVSCKASGYSFT
DYNMVWVRQAPGQCLEWMGYIDPYNGGTYNQKFEGRVTMTTDTSTSTAYMELR
SLRSDDTAVYYCARTRDRYDVWYFDVWGQGTLVTVSSGGGGSGGGGSGGGGSGG
GGSGGGGSDIQMTQSPSSVSASVGDRVTITCKASQDVYIAVAWYQQKPGKAPKL
LIYWASTRDTGVPSRFSGSGSGTDFTLTISSLQPEDFATYYCHQYSSYPPTFGC
GTKVEIK

We claim:

1. A compound, comprising an antibody fused by two linkers to two single chain Fv (scFv) polypeptides, wherein:
   a) the antibody comprises two identical heavy chains (HCs) and two identical light chains (LCs), wherein each HC comprises a heavy chain variable region (HCVR) whose amino acid sequence is given in SEQ ID NO: 4, and wherein each LC comprises a light chain variable region (LVCR) whose amino acid sequence is given in SEQ ID NO: 13,
   b) the two scFv polypeptides are identical and each comprise an HCVR operably linked to an LCVR, wherein each HCVR has the amino acid sequence given in SEQ ID NO: 22, and wherein each LCVR has the amino acid sequence given in SEQ ID NO: 24, and
   c) the two linkers are identical glycine-rich linkers that each operably link the carboxy-terminus of one HC of the antibody to the amino-terminus of one of the scFv polypeptides.

2. The compound of claim 1, wherein the two scFv polypeptides each comprise the carboxy-terminus of the LCVR of one scFv polypeptide operably linked to the amino-terminus of the HCVR of one scFv polypeptide.

3. The compound of claims 1 or 2, wherein the antibody comprises two heavy chains (HCs) and two light chains (LCs), wherein each HC has the amino acid sequence given in SEQ ID NO: 8, and each LC has the amino acid sequence given in SEQ ID NO: 16.

4. The compound of claim 1, wherein each scFv polypeptide has the identical amino acid sequence given in SEQ ID NO: 20.

5. A compound comprising two first polypeptides and two second polypeptides wherein each of the first polypeptides has the amino acid sequence of SEQ ID NO: 12, and each of the second polypeptides has the amino acid sequence of SEQ ID NO: 16.

6. The compound of claim 5, wherein each of the first polypeptides forms an inter-chain disulfide bond with each of the second polypeptides, and the first polypeptide forms two inter-chain disulfide bonds with the other first polypeptide, and each of the first polypeptides forms an intra-chain disulfide bond.

7. A pharmaceutical composition, comprising the compound of claim 1, and an acceptable carrier, diluent, or excipient.

8. A method of treating cancer, comprising administering to a human patient in need thereof, an effective amount of the compound of claim 1.

9. The method of claim 8, wherein the cancer is breast cancer, ovarian cancer, gastric cancer, colorectal cancer, non-small cell lung cancer, biliary tract cancer, or hepatocellular carcinoma.

10. The method of claim 8, wherein the cancer is breast cancer, ovarian cancer, gastric cancer, colorectal cancer, or hepatocellular carcinoma.

\* \* \* \* \*

SEQUENCE LISTING

<160> NUMBER OF SEQ ID NOS: 40

<210> SEQ ID NO 1
<211> LENGTH: 116
<212> TYPE: PRT
<213> ORGANISM: Artificial Sequence
<220> FEATURE:
<223> OTHER INFORMATION: Synthetic Construct

<400> SEQUENCE: 1

Glu Val Gln Leu Val Gln Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ala Ile Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Val Thr Glu Ala Phe Asp Ile Trp Gly Gln Gly Thr Leu Val
            100                 105                 110

Thr Val Ser Ser
        115

<210> SEQ ID NO 2
<211> LENGTH: 116
<212> TYPE: PRT
<213> ORGANISM: Artificial Sequence
<220> FEATURE:
<223> OTHER INFORMATION: Synthetic Construct

<400> SEQUENCE: 2

Glu Val Gln Leu Val Gln Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Leu Trp Val Arg Gln Ala Pro Gly Lys Gly Leu Glu Trp Val
        35                  40                  45

Ser Ala Ile Ser Ser Ser Ser Tyr Thr Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Val Thr Asp Ala Phe Asp Ile Trp Gly Gln Gly Thr Leu Val
            100                 105                 110

Thr Val Ser Ser
        115

<210> SEQ ID NO 3
<211> LENGTH: 116
<212> TYPE: PRT
<213> ORGANISM: Artificial Sequence
<220> FEATURE:
<223> OTHER INFORMATION: Synthetic Construct

<400> SEQUENCE: 3

```
Glu Val Gln Leu Val Gln Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ala Ile Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Val Thr Asp Ala Phe Asp Ile Trp Gly Gln Gly Thr Leu Val
            100                 105                 110

Thr Val Ser Ser
        115

<210> SEQ ID NO 4
<211> LENGTH: 116
<212> TYPE: PRT
<213> ORGANISM: Artificial Sequence
<220> FEATURE:
<223> OTHER INFORMATION: Synthetic Construct

<400> SEQUENCE: 4

Glu Val Gln Leu Val Gln Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Leu Trp Val Arg Gln Ala Pro Gly Lys Gly Leu Glu Trp Val
        35                  40                  45

Ser Ala Ile Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Val Thr Asp Ala Phe Asp Ile Trp Gly Gln Gly Thr Leu Val
            100                 105                 110

Thr Val Ser Ser
        115

<210> SEQ ID NO 5
<211> LENGTH: 442
<212> TYPE: PRT
<213> ORGANISM: Artificial Sequence
<220> FEATURE:
<223> OTHER INFORMATION: Synthetic Construct

<400> SEQUENCE: 5

Glu Val Gln Leu Val Gln Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ala Ile Ser Ser Ser Ser Ser Tyr Ile Tyr Tyr Ala Asp Ser Val
```

```
            50                  55                  60
Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Val Thr Glu Ala Phe Asp Ile Trp Gly Gln Gly Thr Leu Val
                100                 105                 110

Thr Val Ser Ser Ala Ser Thr Lys Gly Pro Ser Val Phe Pro Leu Ala
            115                 120                 125

Pro Cys Ser Arg Ser Thr Ser Glu Ser Thr Ala Ala Leu Gly Cys Leu
        130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Lys Thr Tyr Thr Cys Asn Val Asp His Lys Pro Ser Asn Thr
        195                 200                 205

Lys Val Asp Lys Arg Val Glu Ser Lys Tyr Gly Pro Pro Cys Pro Pro
210                 215                 220

Cys Pro Ala Pro Glu Ala Ala Gly Gly Pro Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser Gln Glu Asp Pro Glu Val Gln Phe Asn
            260                 265                 270

Trp Tyr Val Asp Gly Val Glu Val His Asn Ala Lys Thr Lys Pro Arg
        275                 280                 285

Glu Glu Gln Phe Asn Ser Thr Tyr Arg Val Val Ser Val Leu Thr Val
    290                 295                 300

Leu His Gln Asp Trp Leu Asn Gly Lys Glu Tyr Lys Cys Lys Val Ser
305                 310                 315                 320

Asn Lys Gly Leu Pro Ser Ser Ile Glu Lys Thr Ile Ser Lys Ala Lys
                325                 330                 335

Gly Gln Pro Arg Glu Pro Gln Val Tyr Thr Leu Pro Pro Ser Gln Glu
            340                 345                 350

Glu Met Thr Lys Asn Gln Val Ser Leu Thr Cys Leu Val Lys Gly Phe
        355                 360                 365

Tyr Pro Ser Asp Ile Ala Val Glu Trp Glu Ser Asn Gly Gln Pro Glu
    370                 375                 380

Asn Asn Tyr Lys Thr Thr Pro Pro Val Leu Asp Ser Asp Gly Ser Phe
385                 390                 395                 400

Phe Leu Tyr Ser Arg Leu Thr Val Asp Lys Ser Arg Trp Gln Glu Gly
                405                 410                 415

Asn Val Phe Ser Cys Ser Val Met His Glu Ala Leu His Asn His Tyr
            420                 425                 430

Thr Gln Lys Ser Leu Ser Leu Ser Leu Gly
        435                 440

<210> SEQ ID NO 6
<211> LENGTH: 442
<212> TYPE: PRT
<213> ORGANISM: Artificial Sequence
```

<220> FEATURE:
<223> OTHER INFORMATION: Synthetic Construct

<400> SEQUENCE: 6

```
Glu Val Gln Leu Val Gln Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Leu Trp Val Arg Gln Ala Pro Gly Lys Gly Leu Glu Trp Val
        35                  40                  45

Ser Ala Ile Ser Ser Ser Ser Tyr Thr Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Val Thr Asp Ala Phe Asp Ile Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Cys Ser Arg Ser Thr Ser Glu Ser Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Lys Thr Tyr Thr Cys Asn Val Asp His Lys Pro Ser Asn Thr
        195                 200                 205

Lys Val Asp Lys Arg Val Glu Ser Lys Tyr Gly Pro Pro Cys Pro Pro
    210                 215                 220

Cys Pro Ala Pro Glu Ala Ala Gly Gly Pro Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser Gln Glu Asp Pro Glu Val Gln Phe Asn
            260                 265                 270

Trp Tyr Val Asp Gly Val Glu Val His Asn Ala Lys Thr Lys Pro Arg
        275                 280                 285

Glu Glu Gln Phe Asn Ser Thr Tyr Arg Val Val Ser Val Leu Thr Val
    290                 295                 300

Leu His Gln Asp Trp Leu Asn Gly Lys Glu Tyr Lys Cys Lys Val Ser
305                 310                 315                 320

Asn Lys Gly Leu Pro Ser Ser Ile Glu Lys Thr Ile Ser Lys Ala Lys
                325                 330                 335

Gly Gln Pro Arg Glu Pro Gln Val Tyr Thr Leu Pro Pro Ser Gln Glu
            340                 345                 350

Glu Met Thr Lys Asn Gln Val Ser Leu Thr Cys Leu Val Lys Gly Phe
        355                 360                 365

Tyr Pro Ser Asp Ile Ala Val Glu Trp Glu Ser Asn Gly Gln Pro Glu
    370                 375                 380

Asn Asn Tyr Lys Thr Thr Pro Pro Val Leu Asp Ser Asp Gly Ser Phe
385                 390                 395                 400
```

```
Phe Leu Tyr Ser Arg Leu Thr Val Asp Lys Ser Arg Trp Gln Glu Gly
                405                 410                 415

Asn Val Phe Ser Cys Ser Val Met His Glu Ala Leu His Asn His Tyr
            420                 425                 430

Thr Gln Lys Ser Leu Ser Leu Ser Leu Gly
        435                 440
```

<210> SEQ ID NO 7
<211> LENGTH: 442
<212> TYPE: PRT
<213> ORGANISM: Artificial Sequence
<220> FEATURE:
<223> OTHER INFORMATION: Synthetic Construct

<400> SEQUENCE: 7

```
Glu Val Gln Leu Val Gln Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ala Ile Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Val Thr Asp Ala Phe Asp Ile Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Cys Ser Arg Ser Thr Ser Glu Ser Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Lys Thr Tyr Thr Cys Asn Val Asp His Lys Pro Ser Asn Thr
        195                 200                 205

Lys Val Asp Lys Arg Val Glu Ser Lys Tyr Gly Pro Pro Cys Pro Pro
    210                 215                 220

Cys Pro Ala Pro Glu Ala Ala Gly Gly Pro Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser Gln Glu Asp Pro Glu Val Gln Phe Asn
            260                 265                 270

Trp Tyr Val Asp Gly Val Glu Val His Asn Ala Lys Thr Lys Pro Arg
        275                 280                 285

Glu Glu Gln Phe Asn Ser Thr Tyr Arg Val Val Ser Val Leu Thr Val
    290                 295                 300

Leu His Gln Asp Trp Leu Asn Gly Lys Glu Tyr Lys Cys Lys Val Ser
305                 310                 315                 320
```

Asn Lys Gly Leu Pro Ser Ser Ile Glu Lys Thr Ile Ser Lys Ala Lys
            325                 330                 335

Gly Gln Pro Arg Glu Pro Gln Val Tyr Thr Leu Pro Pro Ser Gln Glu
        340                 345                 350

Glu Met Thr Lys Asn Gln Val Ser Leu Thr Cys Leu Val Lys Gly Phe
    355                 360                 365

Tyr Pro Ser Asp Ile Ala Val Glu Trp Glu Ser Asn Gly Gln Pro Glu
370                 375                 380

Asn Asn Tyr Lys Thr Thr Pro Pro Val Leu Asp Ser Asp Gly Ser Phe
385                 390                 395                 400

Phe Leu Tyr Ser Arg Leu Thr Val Asp Lys Ser Arg Trp Gln Glu Gly
                405                 410                 415

Asn Val Phe Ser Cys Ser Val Met His Glu Ala Leu His Asn His Tyr
            420                 425                 430

Thr Gln Lys Ser Leu Ser Leu Ser Leu Gly
        435                 440

<210> SEQ ID NO 8
<211> LENGTH: 442
<212> TYPE: PRT
<213> ORGANISM: Artificial Sequence
<220> FEATURE:
<223> OTHER INFORMATION: Synthetic Construct

<400> SEQUENCE: 8

Glu Val Gln Leu Val Gln Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Leu Trp Val Arg Gln Ala Pro Gly Lys Gly Leu Glu Trp Val
        35                  40                  45

Ser Ala Ile Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Val Thr Asp Ala Phe Asp Ile Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Cys Ser Arg Ser Thr Ser Glu Ser Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Lys Thr Tyr Thr Cys Asn Val Asp His Lys Pro Ser Asn Thr
        195                 200                 205

Lys Val Asp Lys Arg Val Glu Ser Lys Tyr Gly Pro Pro Cys Pro Pro
    210                 215                 220

Cys Pro Ala Pro Glu Ala Ala Gly Gly Pro Ser Val Phe Leu Phe Pro
225                 230                 235                 240

```
Pro Lys Pro Lys Asp Thr Leu Met Ile Ser Arg Thr Pro Glu Val Thr
            245                 250                 255
Cys Val Val Val Asp Val Ser Gln Glu Asp Pro Glu Val Gln Phe Asn
            260                 265                 270
Trp Tyr Val Asp Gly Val Glu Val His Asn Ala Lys Thr Lys Pro Arg
            275                 280                 285
Glu Glu Gln Phe Asn Ser Thr Tyr Arg Val Val Ser Val Leu Thr Val
            290                 295                 300
Leu His Gln Asp Trp Leu Asn Gly Lys Glu Tyr Lys Cys Lys Val Ser
305                 310                 315                 320
Asn Lys Gly Leu Pro Ser Ser Ile Glu Lys Thr Ile Ser Lys Ala Lys
            325                 330                 335
Gly Gln Pro Arg Glu Pro Gln Val Tyr Thr Leu Pro Pro Ser Gln Glu
            340                 345                 350
Glu Met Thr Lys Asn Gln Val Ser Leu Thr Cys Leu Val Lys Gly Phe
            355                 360                 365
Tyr Pro Ser Asp Ile Ala Val Glu Trp Glu Ser Asn Gly Gln Pro Glu
            370                 375                 380
Asn Asn Tyr Lys Thr Thr Pro Pro Val Leu Asp Ser Asp Gly Ser Phe
385                 390                 395                 400
Phe Leu Tyr Ser Arg Leu Thr Val Asp Lys Ser Arg Trp Gln Glu Gly
            405                 410                 415
Asn Val Phe Ser Cys Ser Val Met His Glu Ala Leu His Asn His Tyr
            420                 425                 430
Thr Gln Lys Ser Leu Ser Leu Ser Leu Gly
            435                 440

<210> SEQ ID NO 9
<211> LENGTH: 709
<212> TYPE: PRT
<213> ORGANISM: Artificial Sequence
<220> FEATURE:
<223> OTHER INFORMATION: Synthetic Construct

<400> SEQUENCE: 9

Glu Val Gln Leu Val Gln Ser Gly Gly Gly Leu Val Lys Pro Gly Gly
1               5                   10                  15
Ser Leu Arg Leu Ser Cys Ala Ala Ser Gly Phe Thr Phe Ser Ser Tyr
            20                  25                  30
Ser Met Asn Trp Val Arg Gln Ala Pro Gly Lys Gly Leu Glu Trp Val
            35                  40                  45
Ser Ala Ile Ser Ser Ser Ser Tyr Ile Tyr Tyr Ala Asp Ser Val
            50                  55                  60
Lys Gly Arg Phe Thr Ile Ser Arg Asp Asn Ala Lys Asn Ser Leu Tyr
65                  70                  75                  80
Leu Gln Met Asn Ser Leu Arg Ala Glu Asp Thr Ala Val Tyr Tyr Cys
            85                  90                  95
Ala Arg Val Thr Glu Ala Phe Asp Ile Trp Gly Gln Gly Thr Leu Val
            100                 105                 110
Thr Val Ser Ser Ala Ser Thr Lys Gly Pro Ser Val Phe Pro Leu Ala
            115                 120                 125
Pro Cys Ser Arg Ser Thr Ser Glu Ser Thr Ala Ala Leu Gly Cys Leu
            130                 135                 140
Val Lys Asp Tyr Phe Pro Glu Pro Val Thr Val Ser Trp Asn Ser Gly
145                 150                 155                 160
```

```
Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Lys Thr Tyr Thr Cys Asn Val Asp His Lys Pro Ser Asn Thr
        195                 200                 205

Lys Val Asp Lys Arg Val Glu Ser Lys Tyr Gly Pro Pro Cys Pro Pro
    210                 215                 220

Cys Pro Ala Pro Glu Ala Ala Gly Gly Pro Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser Gln Glu Asp Pro Glu Val Gln Phe Asn
            260                 265                 270

Trp Tyr Val Asp Gly Val Glu Val His Asn Ala Lys Thr Lys Pro Arg
        275                 280                 285

Glu Glu Gln Phe Asn Ser Thr Tyr Arg Val Val Ser Val Leu Thr Val
    290                 295                 300

Leu His Gln Asp Trp Leu Asn Gly Lys Glu Tyr Lys Cys Lys Val Ser
305                 310                 315                 320

Asn Lys Gly Leu Pro Ser Ser Ile Glu Lys Thr Ile Ser Lys Ala Lys
                325                 330                 335

Gly Gln Pro Arg Glu Pro Gln Val Tyr Thr Leu Pro Pro Ser Gln Glu
            340                 345                 350

Glu Met Thr Lys Asn Gln Val Ser Leu Thr Cys Leu Val Lys Gly Phe
        355                 360                 365

Tyr Pro Ser Asp Ile Ala Val Glu Trp Glu Ser Asn Gly Gln Pro Glu
    370                 375                 380

Asn Asn Tyr Lys Thr Thr Pro Pro Val Leu Asp Ser Asp Gly Ser Phe
385                 390                 395                 400

Phe Leu Tyr Ser Arg Leu Thr Val Asp Lys Ser Arg Trp Gln Glu Gly
                405                 410                 415

Asn Val Phe Ser Cys Ser Val Met His Glu Ala Leu His Asn His Tyr
            420                 425                 430

Thr Gln Lys Ser Leu Ser Leu Ser Leu Gly Gly Gly Gly Ser Gly Gly
        435                 440                 445

Gly Gly Ser Gly Gly Gly Ser Gln Val Gln Leu Val Gln Ser Gly
    450                 455                 460

Ala Glu Val Lys Lys Pro Gly Ala Ser Val Lys Val Ser Cys Lys Ala
465                 470                 475                 480

Ser Gly Tyr Ser Phe Thr Asp Tyr Asn Met Val Trp Val Arg Gln Ala
                485                 490                 495

Pro Gly Gln Cys Leu Glu Trp Met Gly Tyr Ile Asp Pro Tyr Asn Gly
            500                 505                 510

Gly Thr Gly Tyr Asn Gln Lys Phe Glu Gly Arg Val Thr Met Thr Thr
        515                 520                 525

Asp Thr Ser Thr Ser Thr Ala Tyr Met Glu Leu Arg Ser Leu Arg Ser
    530                 535                 540

Asp Asp Thr Ala Val Tyr Tyr Cys Ala Arg Thr Arg Asp Arg Tyr Asp
545                 550                 555                 560

Val Trp Tyr Phe Asp Val Trp Gly Gln Gly Thr Leu Val Thr Val Ser
                565                 570                 575
```

Ser Gly Gly Gly Gly Ser Gly Gly Gly Ser Gly Gly Gly Ser
                580                 585                 590

Gly Gly Gly Gly Ser Gly Gly Gly Ser Asp Ile Gln Met Thr Gln
            595                 600                 605

Ser Pro Ser Ser Val Ser Ala Ser Val Gly Asp Arg Val Thr Ile Thr
610                 615                 620

Cys Lys Ala Ser Gln Asp Val Tyr Ile Ala Val Ala Trp Tyr Gln Gln
625                 630                 635                 640

Lys Pro Gly Lys Ala Pro Lys Leu Leu Ile Tyr Trp Ala Ser Thr Arg
                645                 650                 655

Asp Thr Gly Val Pro Ser Arg Phe Ser Gly Ser Gly Ser Gly Thr Asp
            660                 665                 670

Phe Thr Leu Thr Ile Ser Ser Leu Gln Pro Glu Asp Phe Ala Thr Tyr
        675                 680                 685

Tyr Cys His Gln Tyr Ser Ser Tyr Pro Pro Thr Phe Gly Cys Gly Thr
    690                 695                 700

Lys Val Glu Ile Lys
705

<210> SEQ ID NO 10
<211> LENGTH: 709
<212> TYPE: PRT
<213> ORGANISM: Artificial Sequence
<220> FEATURE:
<223> OTHER INFORMATION: Synthetic Construct

<400> SEQUENCE: 10

Glu Val Gln Leu Val Gln Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Leu Trp Val Arg Gln Ala Pro Gly Lys Gly Leu Glu Trp Val
        35                  40                  45

Ser Ala Ile Ser Ser Ser Ser Tyr Thr Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Val Thr Asp Ala Phe Asp Ile Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Cys Ser Arg Ser Thr Ser Glu Ser Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Lys Thr Tyr Thr Cys Asn Val Asp His Lys Pro Ser Asn Thr
        195                 200                 205

Lys Val Asp Lys Arg Val Glu Ser Lys Tyr Gly Pro Pro Cys Pro Pro
    210                 215                 220

-continued

```
Cys Pro Ala Pro Glu Ala Ala Gly Gly Pro Ser Val Phe Leu Phe Pro
225                 230                 235                 240

Pro Lys Pro Lys Asp Thr Leu Met Ile Ser Arg Thr Pro Glu Val Thr
            245                 250                 255

Cys Val Val Val Asp Val Ser Gln Glu Asp Pro Glu Val Gln Phe Asn
        260                 265                 270

Trp Tyr Val Asp Gly Val Glu Val His Asn Ala Lys Thr Lys Pro Arg
    275                 280                 285

Glu Glu Gln Phe Asn Ser Thr Tyr Arg Val Val Ser Val Leu Thr Val
290                 295                 300

Leu His Gln Asp Trp Leu Asn Gly Lys Glu Tyr Lys Cys Lys Val Ser
305                 310                 315                 320

Asn Lys Gly Leu Pro Ser Ser Ile Glu Lys Thr Ile Ser Lys Ala Lys
                325                 330                 335

Gly Gln Pro Arg Glu Pro Gln Val Tyr Thr Leu Pro Pro Ser Gln Glu
            340                 345                 350

Glu Met Thr Lys Asn Gln Val Ser Leu Thr Cys Leu Val Lys Gly Phe
        355                 360                 365

Tyr Pro Ser Asp Ile Ala Val Glu Trp Glu Ser Asn Gly Gln Pro Glu
    370                 375                 380

Asn Asn Tyr Lys Thr Thr Pro Pro Val Leu Asp Ser Asp Gly Ser Phe
385                 390                 395                 400

Phe Leu Tyr Ser Arg Leu Thr Val Asp Lys Ser Arg Trp Gln Glu Gly
                405                 410                 415

Asn Val Phe Ser Cys Ser Val Met His Glu Ala Leu His Asn His Tyr
            420                 425                 430

Thr Gln Lys Ser Leu Ser Leu Ser Leu Gly Gly Gly Ser Gly Gly
        435                 440                 445

Gly Gly Ser Gly Gly Gly Ser Gln Val Gln Leu Val Gln Ser Gly
    450                 455                 460

Ala Glu Val Lys Lys Pro Gly Ala Ser Val Lys Val Ser Cys Lys Ala
465                 470                 475                 480

Ser Gly Tyr Ser Phe Thr Asp Tyr Asn Met Val Trp Val Arg Gln Ala
                485                 490                 495

Pro Gly Gln Cys Leu Glu Trp Met Gly Tyr Ile Asp Pro Tyr Asn Gly
            500                 505                 510

Gly Thr Gly Tyr Asn Gln Lys Phe Glu Gly Arg Val Thr Met Thr Thr
        515                 520                 525

Asp Thr Ser Thr Ser Thr Ala Tyr Met Glu Leu Arg Ser Leu Arg Ser
    530                 535                 540

Asp Asp Thr Ala Val Tyr Tyr Cys Ala Arg Thr Arg Asp Arg Tyr Asp
545                 550                 555                 560

Val Trp Tyr Phe Asp Val Trp Gly Gln Gly Thr Leu Val Thr Val Ser
                565                 570                 575

Ser Gly Gly Gly Gly Ser Gly Gly Gly Gly Ser Gly Gly Gly Gly Ser
            580                 585                 590

Gly Gly Gly Gly Ser Gly Gly Gly Gly Ser Asp Ile Gln Met Thr Gln
        595                 600                 605

Ser Pro Ser Ser Val Ser Ala Ser Val Gly Asp Arg Val Thr Ile Thr
    610                 615                 620

Cys Lys Ala Ser Gln Asp Val Tyr Ile Ala Val Ala Trp Tyr Gln Gln
625                 630                 635                 640

Lys Pro Gly Lys Ala Pro Lys Leu Leu Ile Tyr Trp Ala Ser Thr Arg
```

```
            645                 650                 655
Asp Thr Gly Val Pro Ser Arg Phe Ser Gly Ser Gly Ser Gly Thr Asp
            660                 665                 670

Phe Thr Leu Thr Ile Ser Ser Leu Gln Pro Glu Asp Phe Ala Thr Tyr
            675                 680                 685

Tyr Cys His Gln Tyr Ser Ser Tyr Pro Pro Thr Phe Gly Cys Gly Thr
            690                 695                 700

Lys Val Glu Ile Lys
705

<210> SEQ ID NO 11
<211> LENGTH: 709
<212> TYPE: PRT
<213> ORGANISM: Artificial Sequence
<220> FEATURE:
<223> OTHER INFORMATION: Synthetic Construct

<400> SEQUENCE: 11

Glu Val Gln Leu Val Gln Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
            35                  40                  45

Ser Ala Ile Ser Ser Ser Ser Tyr Ile Tyr Tyr Ala Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Val Thr Asp Ala Phe Asp Ile Trp Gly Gln Gly Thr Leu Val
            100                 105                 110

Thr Val Ser Ser Ala Ser Thr Lys Gly Pro Ser Val Phe Pro Leu Ala
            115                 120                 125

Pro Cys Ser Arg Ser Thr Ser Glu Ser Thr Ala Ala Leu Gly Cys Leu
        130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Lys Thr Tyr Thr Cys Asn Val Asp His Lys Pro Ser Asn Thr
            195                 200                 205

Lys Val Asp Lys Arg Val Glu Ser Lys Tyr Gly Pro Pro Cys Pro Pro
        210                 215                 220

Cys Pro Ala Pro Glu Ala Ala Gly Gly Pro Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser Gln Glu Asp Pro Glu Val Gln Phe Asn
            260                 265                 270

Trp Tyr Val Asp Gly Val Glu Val His Asn Ala Lys Thr Lys Pro Arg
            275                 280                 285

Glu Glu Gln Phe Asn Ser Thr Tyr Arg Val Val Ser Val Leu Thr Val
```

```
              290                 295                 300
Leu His Gln Asp Trp Leu Asn Gly Lys Glu Tyr Lys Cys Lys Val Ser
305                 310                 315                 320

Asn Lys Gly Leu Pro Ser Ser Ile Glu Lys Thr Ile Ser Lys Ala Lys
                325                 330                 335

Gly Gln Pro Arg Glu Pro Gln Val Tyr Thr Leu Pro Pro Ser Gln Glu
                340                 345                 350

Glu Met Thr Lys Asn Gln Val Ser Leu Thr Cys Leu Val Lys Gly Phe
            355                 360                 365

Tyr Pro Ser Asp Ile Ala Val Glu Trp Glu Ser Asn Gly Gln Pro Glu
        370                 375                 380

Asn Asn Tyr Lys Thr Thr Pro Pro Val Leu Asp Ser Asp Gly Ser Phe
385                 390                 395                 400

Phe Leu Tyr Ser Arg Leu Thr Val Asp Lys Ser Arg Trp Gln Glu Gly
                405                 410                 415

Asn Val Phe Ser Cys Ser Val Met His Glu Ala Leu His Asn His Tyr
                420                 425                 430

Thr Gln Lys Ser Leu Ser Leu Ser Leu Gly Gly Gly Ser Gly Gly
            435                 440                 445

Gly Gly Ser Gly Gly Gly Ser Gln Val Gln Leu Val Gln Ser Gly
        450                 455                 460

Ala Glu Val Lys Lys Pro Gly Ala Ser Val Lys Val Ser Cys Lys Ala
465                 470                 475                 480

Ser Gly Tyr Ser Phe Thr Asp Tyr Asn Met Val Trp Val Arg Gln Ala
                485                 490                 495

Pro Gly Gln Cys Leu Glu Trp Met Gly Tyr Ile Asp Pro Tyr Asn Gly
                500                 505                 510

Gly Thr Gly Tyr Asn Gln Lys Phe Glu Gly Arg Val Thr Met Thr Thr
            515                 520                 525

Asp Thr Ser Thr Ser Thr Ala Tyr Met Glu Leu Arg Ser Leu Arg Ser
        530                 535                 540

Asp Asp Thr Ala Val Tyr Tyr Cys Ala Arg Thr Arg Asp Arg Tyr Asp
545                 550                 555                 560

Val Trp Tyr Phe Asp Val Trp Gly Gln Gly Thr Leu Val Thr Val Ser
                565                 570                 575

Ser Gly Gly Gly Gly Ser Gly Gly Gly Ser Gly Gly Gly Gly Ser
            580                 585                 590

Gly Gly Gly Gly Ser Gly Gly Gly Ser Asp Ile Gln Met Thr Gln
        595                 600                 605

Ser Pro Ser Ser Val Ser Ala Ser Val Gly Asp Arg Val Thr Ile Thr
610                 615                 620

Cys Lys Ala Ser Gln Asp Val Tyr Ile Ala Val Ala Trp Tyr Gln Gln
625                 630                 635                 640

Lys Pro Gly Lys Ala Pro Lys Leu Leu Ile Tyr Trp Ala Ser Thr Arg
                645                 650                 655

Asp Thr Gly Val Pro Ser Arg Phe Ser Gly Ser Gly Ser Gly Thr Asp
                660                 665                 670

Phe Thr Leu Thr Ile Ser Ser Leu Gln Pro Glu Asp Phe Ala Thr Tyr
            675                 680                 685

Tyr Cys His Gln Tyr Ser Ser Tyr Pro Pro Thr Phe Gly Cys Gly Thr
        690                 695                 700

Lys Val Glu Ile Lys
705
```

<210> SEQ ID NO 12
<211> LENGTH: 704
<212> TYPE: PRT
<213> ORGANISM: Artificial Sequence
<220> FEATURE:
<223> OTHER INFORMATION: Synthetic Construct

<400> SEQUENCE: 12

```
Glu Val Gln Leu Val Gln Ser Gly Gly Gly Leu Val Lys Pro Gly Gly
 1               5                  10                  15

Ser Leu Arg Leu Ser Cys Ala Ala Ser Gly Phe Thr Phe Ser Ser Tyr
            20                  25                  30

Ser Met Leu Trp Val Arg Gln Ala Pro Gly Lys Gly Leu Glu Trp Val
        35                  40                  45

Ser Ala Ile Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                85                  90                  95

Ala Arg Val Thr Asp Ala Phe Asp Ile Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Cys Ser Arg Ser Thr Ser Glu Ser Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Lys Thr Tyr Thr Cys Asn Val Asp His Lys Pro Ser Asn Thr
        195                 200                 205

Lys Val Asp Lys Arg Val Glu Ser Lys Tyr Gly Pro Pro Cys Pro Pro
    210                 215                 220

Cys Pro Ala Pro Glu Ala Ala Gly Gly Pro Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser Gln Glu Asp Pro Glu Val Gln Phe Asn
            260                 265                 270

Trp Tyr Val Asp Gly Val Glu Val His Asn Ala Lys Thr Lys Pro Arg
        275                 280                 285

Glu Glu Gln Phe Asn Ser Thr Tyr Arg Val Val Ser Val Leu Thr Val
    290                 295                 300

Leu His Gln Asp Trp Leu Asn Gly Lys Glu Tyr Lys Cys Lys Val Ser
305                 310                 315                 320

Asn Lys Gly Leu Pro Ser Ser Ile Glu Lys Thr Ile Ser Lys Ala Lys
                325                 330                 335

Gly Gln Pro Arg Glu Pro Gln Val Tyr Thr Leu Pro Pro Ser Gln Glu
            340                 345                 350

Glu Met Thr Lys Asn Gln Val Ser Leu Thr Cys Leu Val Lys Gly Phe
        355                 360                 365
```

Tyr Pro Ser Asp Ile Ala Val Glu Trp Glu Ser Asn Gly Gln Pro Glu
        370                 375                 380

Asn Asn Tyr Lys Thr Thr Pro Pro Val Leu Asp Ser Asp Gly Ser Phe
385                 390                 395                 400

Phe Leu Tyr Ser Arg Leu Thr Val Asp Lys Ser Arg Trp Gln Glu Gly
            405                 410                 415

Asn Val Phe Ser Cys Ser Val Met His Glu Ala Leu His Asn His Tyr
        420                 425                 430

Thr Gln Lys Ser Leu Ser Leu Ser Leu Gly Gly Gly Ser Gly Gly
            435                 440                 445

Gly Gly Ser Gly Gly Gly Gly Ser Asp Ile Val Met Thr Gln Ser Pro
        450                 455                 460

Asp Ser Leu Ala Val Ser Leu Gly Glu Arg Ala Thr Ile Asn Cys Lys
465                 470                 475                 480

Ala Ser Gln Asp Val Tyr Ile Ala Val Ala Trp Tyr Gln Gln Lys Pro
            485                 490                 495

Gly Gln Pro Pro Lys Leu Leu Ile Tyr Trp Ala Ser Thr Arg Asp Thr
        500                 505                 510

Gly Val Pro Asp Arg Phe Ser Gly Ser Gly Ser Gly Thr Asp Phe Thr
        515                 520                 525

Leu Thr Ile Ser Ser Leu Gln Ala Glu Asp Val Ala Val Tyr Tyr Cys
530                 535                 540

His Gln Tyr Ser Ser Tyr Pro Pro Thr Phe Gly Cys Gly Thr Lys Val
545                 550                 555                 560

Glu Ile Lys Gly Gly Gly Gly Ser Gly Gly Gly Gly Ser Gly Gly Gly
            565                 570                 575

Gly Ser Gly Gly Gly Gly Ser Gln Val Gln Leu Val Gln Ser Gly Ala
        580                 585                 590

Glu Val Lys Lys Pro Gly Ser Ser Val Lys Val Ser Cys Lys Ala Ser
            595                 600                 605

Gly Tyr Ser Phe Thr Asp Tyr Asn Met Val Trp Val Arg Gln Ala Pro
        610                 615                 620

Gly Gln Cys Leu Glu Trp Met Gly Tyr Ile Asp Pro Tyr Asn Gly Gly
625                 630                 635                 640

Thr Gly Tyr Asn Gln Lys Phe Glu Gly Arg Val Thr Ile Thr Ala Asp
            645                 650                 655

Glu Ser Thr Ser Thr Ala Tyr Met Glu Leu Ser Ser Leu Arg Ser Glu
        660                 665                 670

Asp Thr Ala Val Tyr Tyr Cys Ala Arg Thr Arg Asp Arg Tyr Asp Val
            675                 680                 685

Trp Tyr Phe Asp Val Trp Gly Gln Gly Thr Leu Val Thr Val Ser Ser
        690                 695                 700

<210> SEQ ID NO 13
<211> LENGTH: 107
<212> TYPE: PRT
<213> ORGANISM: Artificial Sequence
<220> FEATURE:
<223> OTHER INFORMATION: Synthetic Construct

<400> SEQUENCE: 13

Asp Ile Gln Met Thr Gln Ser Pro Ser Val Ser Ala Ser Val Gly
1               5                   10                  15

Asp Arg Val Thr Ile Thr Cys Arg Ala Ser Arg Gly Ile Asp Asn Trp
            20                  25                  30

-continued

Leu Thr Trp Tyr Gln Gln Lys Pro Gly Lys Ala Pro Lys Leu Leu Ile
            35                  40                  45

Tyr Glu Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ala Lys Ala Phe Pro Pro
                 85                  90                  95

Thr Phe Gly Gly Gly Thr Lys Val Asp Ile Lys
            100                 105

<210> SEQ ID NO 14
<211> LENGTH: 107
<212> TYPE: PRT
<213> ORGANISM: Artificial Sequence
<220> FEATURE:
<223> OTHER INFORMATION: Synthetic Construct

<400> SEQUENCE: 14

Asp Ile Gln Met Thr Gln Ser Pro Ser Ser Val Ser Ala Ser Val Gly
 1               5                  10                  15

Asp Arg Val Thr Ile Thr Cys Arg Ala Ser Gln Gly Ile Asp Asn Trp
                 20                  25                  30

Leu Thr Trp Tyr Gln Gln Lys Pro Gly Lys Ala Pro Lys Leu Leu Ile
            35                  40                  45

Val Glu Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ala Lys Arg Phe Pro Pro
                 85                  90                  95

Thr Phe Gly Gly Gly Thr Lys Val Asp Ile Lys
            100                 105

<210> SEQ ID NO 15
<211> LENGTH: 107
<212> TYPE: PRT
<213> ORGANISM: Artificial Sequence
<220> FEATURE:
<223> OTHER INFORMATION: Synthetic Construct

<400> SEQUENCE: 15

Asp Ile Gln Met Thr Gln Ser Pro Ser Ser Val Ser Ala Ser Val Gly
 1               5                  10                  15

Asp Arg Val Thr Ile Thr Cys Arg Ala Ser Gln Gly Ile Asp Asn Trp
                 20                  25                  30

Leu Thr Trp Tyr Gln Gln Lys Pro Gly Lys Ala Pro Lys Leu Leu Ile
            35                  40                  45

Val Glu Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ala Lys Ala Phe Pro Pro
                 85                  90                  95

Thr Phe Gly Gly Gly Thr Lys Val Asp Ile Lys
            100                 105

```
<210> SEQ ID NO 16
<211> LENGTH: 214
<212> TYPE: PRT
<213> ORGANISM: Artificial Sequence
<220> FEATURE:
<223> OTHER INFORMATION: Synthetic Construct

<400> SEQUENCE: 16

Asp Ile Gln Met Thr Gln Ser Pro Ser Ser Val Ser Ala Ser Val Gly
1               5                   10                  15

Asp Arg Val Thr Ile Thr Cys Arg Ala Ser Arg Gly Ile Asp Asn Trp
            20                  25                  30

Leu Thr Trp Tyr Gln Gln Lys Pro Gly Lys Ala Pro Lys Leu Leu Ile
        35                  40                  45

Tyr Glu Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Lys Ala Phe Pro Pro
                85                  90                  95

Thr Phe Gly Gly Gly Thr Lys Val Asp Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 17
<211> LENGTH: 214
<212> TYPE: PRT
<213> ORGANISM: Artificial Sequence
<220> FEATURE:
<223> OTHER INFORMATION: Synthetic Construct

<400> SEQUENCE: 17

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Asp Asn Trp
            20                  25                  30

Leu Thr Trp Tyr Gln Gln Lys Pro Gly Lys Ala Pro Lys Leu Leu Ile
        35                  40                  45

Val Glu Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Lys Arg Phe Pro Pro
                85                  90                  95
```

```
Thr Phe Gly Gly Gly Thr Lys Val Asp Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 18
<211> LENGTH: 214
<212> TYPE: PRT
<213> ORGANISM: Artificial Sequence
<220> FEATURE:
<223> OTHER INFORMATION: Synthetic Construct

<400> SEQUENCE: 18

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Asp Asn Trp
            20                  25                  30

Leu Thr Trp Tyr Gln Gln Lys Pro Gly Lys Ala Pro Lys Leu Leu Ile
        35                  40                  45

Val Glu Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Lys Ala Phe Pro Pro
                85                  90                  95

Thr Phe Gly Gly Gly Thr Lys Val Asp Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 19
<211> LENGTH: 253
```

```
<212> TYPE: PRT
<213> ORGANISM: Artificial Sequence
<220> FEATURE:
<223> OTHER INFORMATION: Synthetic Construct

<400> SEQUENCE: 19

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Asp Tyr
            20                  25                  30

Asn Met Val Trp Val Arg Gln Ala Pro Gly Gln Cys Leu Glu Trp Met
        35                  40                  45

Gly Tyr Ile Asp Pro Tyr Asn Gly Gly Thr Gly Tyr Asn Gln Lys Phe
    50                  55                  60

Glu Gly Arg Val Thr Met Thr Thr Asp Thr Ser Thr Ser Thr Ala Tyr
65                  70                  75                  80

Met Glu Leu Arg Ser Leu Arg Ser Asp Thr Ala Val Tyr Tyr Cys
                85                  90                  95

Ala Arg Thr Arg Asp Arg Tyr Asp Val Trp Tyr Phe Asp Val Trp Gly
            100                 105                 110

Gln Gly Thr Leu Val Thr Val Ser Ser Gly Gly Gly Ser Gly Gly
            115                 120                 125

Gly Gly Ser Gly Gly Gly Ser Gly Gly Gly Ser Gly Gly
    130                 135                 140

Gly Ser Asp Ile Gln Met Thr Gln Ser Pro Ser Ser Val Ser Ala Ser
145                 150                 155                 160

Val Gly Asp Arg Val Thr Ile Thr Cys Lys Ala Ser Gln Asp Val Tyr
                165                 170                 175

Ile Ala Val Ala Trp Tyr Gln Gln Lys Pro Gly Lys Ala Pro Lys Leu
            180                 185                 190

Leu Ile Tyr Trp Ala Ser Thr Arg Asp Thr Gly Val Pro Ser Arg Phe
        195                 200                 205

Ser Gly Ser Gly Ser Gly Thr Asp Phe Thr Leu Thr Ile Ser Ser Leu
    210                 215                 220

Gln Pro Glu Asp Phe Ala Thr Tyr Tyr Cys His Gln Tyr Ser Ser Tyr
225                 230                 235                 240

Pro Pro Thr Phe Gly Cys Gly Thr Lys Val Glu Ile Lys
                245                 250

<210> SEQ ID NO 20
<211> LENGTH: 248
<212> TYPE: PRT
<213> ORGANISM: Artificial Sequence
<220> FEATURE:
<223> OTHER INFORMATION: Synthetic Construct

<400> SEQUENCE: 20

Asp Ile Val Met Thr Gln Ser Pro Asp Ser Leu Ala Val Ser Leu Gly
1               5                   10                  15

Glu Arg Ala Thr Ile Asn Cys Lys Ala Ser Gln Asp Val Tyr Ile Ala
            20                  25                  30

Val Ala Trp Tyr Gln Gln Lys Pro Gly Gln Pro Pro Lys Leu Leu Ile
        35                  40                  45

Tyr Trp Ala Ser Thr Arg Asp Thr Gly Val Pro Asp Arg Phe Ser Gly
    50                  55                  60

Ser Gly Ser Gly Thr Asp Phe Thr Leu Thr Ile Ser Ser Leu Gln Ala
65                  70                  75                  80
```

```
Glu Asp Val Ala Val Tyr Tyr Cys His Gln Tyr Ser Ser Tyr Pro Pro
                85                  90                  95

Thr Phe Gly Cys Gly Thr Lys Val Glu Ile Lys Gly Gly Gly Gly Ser
            100                 105                 110

Gly Gly Gly Gly Ser Gly Gly Gly Ser Gly Gly Gly Gly Ser Gln
        115                 120                 125

Val Gln Leu Val Gln Ser Gly Ala Glu Val Lys Lys Pro Gly Ser Ser
130                 135                 140

Val Lys Val Ser Cys Lys Ala Ser Gly Tyr Ser Phe Thr Asp Tyr Asn
145                 150                 155                 160

Met Val Trp Val Arg Gln Ala Pro Gly Gln Cys Leu Glu Trp Met Gly
                165                 170                 175

Tyr Ile Asp Pro Tyr Asn Gly Gly Thr Gly Tyr Asn Gln Lys Phe Glu
            180                 185                 190

Gly Arg Val Thr Ile Thr Ala Asp Glu Ser Ser Thr Ala Tyr Met
        195                 200                 205

Glu Leu Ser Ser Leu Arg Ser Glu Asp Thr Ala Val Tyr Tyr Cys Ala
210                 215                 220

Arg Thr Arg Asp Arg Tyr Asp Val Trp Tyr Phe Asp Val Trp Gly Gln
225                 230                 235                 240

Gly Thr Leu Val Thr Val Ser Ser
                245

<210> SEQ ID NO 21
<211> LENGTH: 121
<212> TYPE: PRT
<213> ORGANISM: Artificial Sequence
<220> FEATURE:
<223> OTHER INFORMATION: Synthetic Construct

<400> SEQUENCE: 21

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Asp Tyr
            20                  25                  30

Asn Met Val Trp Val Arg Gln Ala Pro Gly Gln Cys Leu Glu Trp Met
        35                  40                  45

Gly Tyr Ile Asp Pro Tyr Asn Gly Gly Thr Gly Tyr Asn Gln Lys Phe
    50                  55                  60

Glu Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Thr Arg Asp Arg Tyr Asp Val Trp Tyr Phe Asp Val Trp Gly
            100                 105                 110

Gln Gly Thr Leu Val Thr Val Ser Ser
        115                 120

<210> SEQ ID NO 22
<211> LENGTH: 121
<212> TYPE: PRT
<213> ORGANISM: Artificial Sequence
<220> FEATURE:
<223> OTHER INFORMATION: Synthetic Construct

<400> SEQUENCE: 22

Gln Val Gln Leu Val Gln Ser Gly Ala Glu Val Lys Lys Pro Gly Ser
```

-continued

```
1               5                   10                  15
Ser Val Lys Val Ser Cys Lys Ala Ser Gly Tyr Ser Phe Thr Asp Tyr
                20                  25                  30
Asn Met Val Trp Val Arg Gln Ala Pro Gly Gln Cys Leu Glu Trp Met
                35                  40                  45
Gly Tyr Ile Asp Pro Tyr Asn Gly Gly Thr Gly Tyr Asn Gln Lys Phe
            50                  55                  60
Glu Gly Arg Val Thr Ile Thr Ala Asp Glu Ser Thr Ser Thr Ala Tyr
65                  70                  75                  80
Met Glu Leu Ser Ser Leu Arg Ser Glu Asp Thr Ala Val Tyr Tyr Cys
                85                  90                  95
Ala Arg Thr Arg Asp Arg Tyr Asp Val Trp Tyr Phe Asp Val Trp Gly
                100                 105                 110
Gln Gly Thr Leu Val Thr Val Ser Ser
                115                 120
```

<210> SEQ ID NO 23
<211> LENGTH: 107
<212> TYPE: PRT
<213> ORGANISM: Artificial Sequence
<220> FEATURE:
<223> OTHER INFORMATION: Synthetic Construct

<400> SEQUENCE: 23

```
Asp Ile Gln Met Thr Gln Ser Pro Ser Ser Val Ser Ala Ser Val Gly
1               5                   10                  15
Asp Arg Val Thr Ile Thr Cys Lys Ala Ser Gln Asp Val Tyr Ile Ala
                20                  25                  30
Val Ala Trp Tyr Gln Gln Lys Pro Gly Lys Ala Pro Lys Leu Leu Ile
                35                  40                  45
Tyr Trp Ala Ser Thr Arg Asp Thr Gly Val Pro Ser Arg Phe Ser Gly
            50                  55                  60
Ser Gly Ser Gly Thr Asp Phe Thr Leu Thr Ile Ser Ser Leu Gln Pro
65                  70                  75                  80
Glu Asp Phe Ala Thr Tyr Tyr Cys His Gln Tyr Ser Ser Tyr Pro Pro
                85                  90                  95
Thr Phe Gly Cys Gly Thr Lys Val Glu Ile Lys
                100                 105
```

<210> SEQ ID NO 24
<211> LENGTH: 107
<212> TYPE: PRT
<213> ORGANISM: Artificial Sequence
<220> FEATURE:
<223> OTHER INFORMATION: Synthetic Construct

<400> SEQUENCE: 24

```
Asp Ile Val Met Thr Gln Ser Pro Asp Ser Leu Ala Val Ser Leu Gly
1               5                   10                  15
Glu Arg Ala Thr Ile Asn Cys Lys Ala Ser Gln Asp Val Tyr Ile Ala
                20                  25                  30
Val Ala Trp Tyr Gln Gln Lys Pro Gly Gln Pro Pro Lys Leu Leu Ile
                35                  40                  45
Tyr Trp Ala Ser Thr Arg Asp Thr Gly Val Pro Asp Arg Phe Ser Gly
            50                  55                  60
Ser Gly Ser Gly Thr Asp Phe Thr Leu Thr Ile Ser Ser Leu Gln Ala
65                  70                  75                  80
```

Glu Asp Val Ala Val Tyr Tyr Cys His Gln Tyr Ser Ser Tyr Pro Pro
            85                  90                  95

Thr Phe Gly Cys Gly Thr Lys Val Glu Ile Lys
            100                 105

<210> SEQ ID NO 25
<211> LENGTH: 2127
<212> TYPE: DNA
<213> ORGANISM: Artificial Sequence
<220> FEATURE:
<223> OTHER INFORMATION: Synthetic Construct

<400> SEQUENCE: 25

| | | | | | |
|---|---|---|---|---|---|
| gaggtccagc | tggtgcagtc | tgggggaggc | tggtcaagc | ctgggggtc | cctgagactc | 60 |
| tcctgtgcag | cctctggatt | caccttcagt | agctatagca | tgaactgggt | ccgccaggct | 120 |
| ccagggaagg | ggctggagtg | ggtctcagcc | attagtagta | gtagtagtta | catatactac | 180 |
| gcagactcag | tgaagggccg | attcaccatc | tccagagaca | acgccaagaa | ctcactgtat | 240 |
| ctgcaaatga | acagcctgag | agccgaggac | acggctgtgt | attactgtgc | gagagtcaca | 300 |
| gaggcttttg | atatctgggg | ccaagggaca | ctggtcaccg | tctcaagcgc | ctccaccaag | 360 |
| ggcccatcgg | tcttccccct | ggcgccctgc | tccaggagca | cctccgagag | cacagccgcc | 420 |
| ctgggctgcc | tggtcaagga | ctacttcccc | gaaccggtga | cggtgtcgtg | gaactcaggc | 480 |
| gccctgacca | gcggcgtgca | caccttcccg | gctgtcctac | agtcctcagg | actctactcc | 540 |
| ctcagcagcg | tggtgaccgt | gccctccagc | agcttgggca | cgaagaccta | cacctgcaac | 600 |
| gtagatcaca | agcccagcaa | caccaaggtg | gacaagagag | ttgagtccaa | atatggtccc | 660 |
| ccatgcccac | cctgcccagc | acctgaggcc | gccggggac | catcagtctt | cctgttcccc | 720 |
| ccaaaaccca | aggacactct | catgatctcc | cggacccctg | aggtcacgtg | cgtggtggtg | 780 |
| gacgtgagcc | aggaagaccc | cgaggtccag | ttcaactggt | acgtggatgg | cgtggaggtg | 840 |
| cataatgcca | agacaaagcc | gcgggaggag | cagttcaaca | gcacgtaccg | tgtggtcagc | 900 |
| gtcctcaccg | tcctgcacca | ggactggctg | aacggcaagg | agtacaagtg | caaggtctcc | 960 |
| aacaaaggcc | tcccgtcctc | catcgagaaa | accatctcca | aagccaaagg | gcagccccga | 1020 |
| gagccacagg | tgtacaccct | gccccatcc | caggaggaga | tgaccaagaa | ccaggtcagc | 1080 |
| ctgacctgcc | tggtcaaagg | cttctacccc | agcgacatcg | ccgtggagtg | ggaaagcaat | 1140 |
| gggcagccgg | agaacaacta | caagaccacg | cctcccgtgc | tggactccga | cggctccttc | 1200 |
| ttcctctaca | gcaggctaac | cgtggacaag | agcaggtggc | aggagggaa | tgtcttctca | 1260 |
| tgctccgtga | tgcatgaggc | tctgcacaac | cactacacac | agaagagcct | ctccctgtct | 1320 |
| ctgggtggcg | gaggctccgg | gggaggggg | agcggaggag | gggatccca | ggttcagctg | 1380 |
| gtgcagtctg | gagctgaggt | gaagaagcct | ggggcctcag | tgaaggtctc | ctgcaaggct | 1440 |
| tctggttact | cattcactga | ctacaacatg | gtgtgggtgc | gacaggcccc | tggacaatgc | 1500 |
| cttgagtgga | tgggatatat | tgatcccta | aatggtggta | ctggctacaa | ccagaagttc | 1560 |
| gagggcagag | tcaccatgac | cacagacaca | tccacgagca | cagcctacat | ggagctgagg | 1620 |
| agcctgagat | ctgacgacac | ggccgtgtat | tactgtgcga | gaacgaggga | tagatacgac | 1680 |
| gtctggtact | tcgatgtctg | gggccaggga | accctggtca | ccgtctcctc | aggaggcgga | 1740 |
| ggttccgggg | gaggggcag | cggaggaggc | ggatcgggcg | gaggaggaag | tggaggcgga | 1800 |
| ggcagcgaca | tccagatgac | ccagtctcca | tcttccgtgt | ctgcatctgt | tggcgacaga | 1860 |
| gtcaccatca | cttgtaaggc | cagtcaggat | gtgtatattg | ctgtagcctg | gtatcagcag | 1920 |

| aaaccaggga aagcccctaa gctcctgatc tattgggcat ccacccggga cactggggtc | 1980 |
| ccatcaaggt tcagcggcag tggatctggg acagatttca ctctcaccat cagcagcctg | 2040 |
| cagcctgaag attttgcaac ttactattgt caccaatata gcagctatcc tcctacgttc | 2100 |
| ggctgcggga ccaaggtgga gatcaaa | 2127 |

<210> SEQ ID NO 26
<211> LENGTH: 642
<212> TYPE: DNA
<213> ORGANISM: Artificial Sequence
<220> FEATURE:
<223> OTHER INFORMATION: Synthetic Construct

<400> SEQUENCE: 26

| gacatccaga tgacccagtc tccatcttct gtgtctgcat ctgtaggaga cagagtcacc |  60 |
| atcacttgtc gggcgagtcg tggtattgac aactggttaa cgtggtatca gcagaaacca | 120 |
| gggaaagccc ctaagctcct gatttacgaa gcatccagtt tgcaatcagg gtcccatca | 180 |
| aggttcagcg gcagtggatc tgggacagat ttcactctca ctatcagcag cctgcagcct | 240 |
| gaagattttg caacttacta ttgtcaacaa gctaaggctt ttcctcccac tttcggcgga | 300 |
| gggaccaagg tggacatcaa acgaactgtg gctgcaccat ctgtcttcat cttcccgcca | 360 |
| tctgatgagc agttgaaatc tggaactgcc tctgttgtgt gcctgctgaa taacttctat | 420 |
| cccagagagg ccaaagtaca gtggaaggtg gataacgccc tccaatcggg taactcccag | 480 |
| gagagtgtca cagagcagga cagcaaggac agcacctaca gcctcagcag cacccctgacg | 540 |
| ctgagcaaag cagactacga aaacacaaa gtctacgcct gcgaagtcac ccatcagggc | 600 |
| ctgagctcgc ccgtcacaaa gagcttcaac aggggagagt gc | 642 |

<210> SEQ ID NO 27
<211> LENGTH: 2127
<212> TYPE: DNA
<213> ORGANISM: Artificial Sequence
<220> FEATURE:
<223> OTHER INFORMATION: Synthetic Construct

<400> SEQUENCE: 27

| gaggtccagc tggtgcagtc tggggggaggc ctggtcaagc ctgggggggtc cctgagactc |  60 |
| tcctgtgcag cctctggatt caccttcagt agctatagca tgctttgggt ccgccaggct | 120 |
| ccagggaagg gctggagtg gtctcagcc attagtagta gtagtagtta cacctactac | 180 |
| gcagactcag tgaagggccg attcaccatc tccagagaca cgccaagaa ctcactgtat | 240 |
| ctgcaaatga acagcctgag agccgaggac acggctgtgt attactgtgc gagagtcaca | 300 |
| gatgcttttg atatctgggg ccaagggaca ctggtcaccg tctcaagcgc ctccaccaag | 360 |
| ggcccatcgg tcttccccgct agcgccctgc tccaggagca cctccgagag cacagccgcc | 420 |
| ctgggctgcc tggtcaagga ctacttcccc gaaccggtga cggtgtcgtg gaactcaggc | 480 |
| gccctgacca gcggcgtgca ccttcccg gctgtcctac agtcctcagg actctactcc | 540 |
| ctcagcagcg tggtgaccgt gccctccagc agcttgggca cgaagaccta cacctgcaac | 600 |
| gtagatcaca agcccagcaa caccaaggtg gacaagagag ttgagtccaa atatggtccc | 660 |
| ccatgcccac cctgcccagc acctgaggcc gccgggggac catcagtctt cctgttcccc | 720 |
| ccaaaaccca aggacactct catgatctcc cggacccctg aggtcacgtg cgtggtggtg | 780 |
| gacgtgagcc aggaagaccc cgaggtccag ttcaactggt acgtggatgg cgtggaggtg | 840 |

```
cataatgcca agacaaagcc gcgggaggag cagttcaaca gcacgtaccg tgtggtcagc      900
gtcctcaccg tcctgcacca ggactggctg aacggcaagg agtacaagtg caaggtctcc      960
aacaaaggcc tcccgtcctc catcgagaaa accatctcca aagccaaagg gcagccccga     1020
gagccacagg tgtacaccct gcccccatcc caggaggaga tgaccaagaa ccaggtcagc     1080
ctgacctgcc tggtcaaagg cttctacccc agcgacatcg ccgtggagtg ggaaagcaat     1140
gggcagccgg agaacaacta caagaccacg cctcccgtgc tggactccga cggctccttc     1200
ttcctctaca gcaggctaac cgtggacaag agcaggtggc aggaggggaa tgtcttctca     1260
tgctccgtga tgcatgaggc tctgcacaac cactacacac agaagagcct ctccctgtct     1320
ctgggtggcg gaggctccgg ggagggggt agcggaggag ggggatccca ggttcagctg     1380
gtgcagtctg gagctgaggt gaagaagcct ggggcctcag tgaaggtctc ctgcaaggct     1440
tctggttact cattcactga ctacaacatg gtgtgggtgc gacaggcccc tggacaatgc     1500
cttgagtgga tgggatatat tgatccttac aatggtggta ctggctacaa ccagaagttc     1560
gagggcagag tcaccatgac cacagacaca tccacgagca gcctacat ggagctgagg     1620
agcctgagat ctgacgacac ggccgtgtat tactgtgcga gaacgaggga tagatacgac     1680
gtctggtact cgatgtctg gggccaggga accctggtca ccgtctcctc aggaggcgga     1740
ggttccgggg gagggggcag cggaggaggc ggatcgggcg gaggaggaag tggaggcgga     1800
ggcagcgaca tccagatgac ccagtctcca tcttccgtgt ctgcatctgt ggcgacaga     1860
gtcaccatca cttgtaaggc cagtcaggat gtgtatattg ctgtagcctg gtatcagcag     1920
aaaccaggga aagcccctaa gctcctgatc tattgggcat ccacccggga cactgggtc     1980
ccatcaaggt tcagcggcag tggatctggg acagatttca ctctcaccat cagcagcctg     2040
cagcctgaag attttgcaac ttactattgt caccaatata gcagctatcc tcctacgttc     2100
ggctgcggga ccaaggtgga gatcaaa                                         2127

<210> SEQ ID NO 28
<211> LENGTH: 642
<212> TYPE: DNA
<213> ORGANISM: Artificial Sequence
<220> FEATURE:
<223> OTHER INFORMATION: Synthetic Construct

<400> SEQUENCE: 28
gacatccaga tgacccagtc tccatcttct gtgtctgcat ctgtaggaga cagagtcacc       60
atcacttgtc gggcgagtca gggtattgac aactggttaa cgtggtatca gcagaaacca      120
gggaaagccc ctaagctcct gatcgtcgag gcatccagtt tgcaatcagg ggtcccatca      180
aggttcagcg gcagtggatc tgggacagat ttcactctca ctatcagcag cctgcagcct      240
gaagattttg caacttacta ttgtcaacag gctaagaggt ttcctcccac tttcggcgga      300
gggaccaagg tggacatcaa acgaactgtg gctgcaccat ctgtcttcat cttcccgcca      360
tctgatgagc agttgaaatc tggaactgcc tctgttgtgt gcctgctgaa taacttctat      420
cccagagagg ccaaagtaca gtggaaggtg gataacgccc tccaatcggg taactcccag      480
gagagtgtca cagagcagga cagcaaggac agcacctaca gcctcagcag cacccctgacg      540
ctgagcaaag cagactacga gaaacacaaa gtctacgcct gcgaagtcac ccatcagggc      600
ctgagctcgc ccgtcacaaa gagcttcaac aggggagagt gc                         642

<210> SEQ ID NO 29
<211> LENGTH: 2127
```

```
<212> TYPE: DNA
<213> ORGANISM: Artificial Sequence
<220> FEATURE:
<223> OTHER INFORMATION: Synthetic Construct

<400> SEQUENCE: 29
gaggtccagc tggtgcagtc tgggggaggc ctggtcaagc ctggggggtc cctgagactc      60
tcctgtgcag cctctggatt caccttcagt agctatagca tgaactgggt ccgccaggct     120
ccagggaagg ggctggagtg ggtctcagcg attagtagta gtagtagtta catatactac     180
gcagactcag tgaagggccg attcaccatc tccagagaca acgccaagaa ctcactgtat     240
ctgcaaatga acagcctgag agccgaggac acggctgtgt attactgtgc gagagtcaca     300
gatgcttttg atatctgggg ccaagggaca ctggtcaccg tctcaagcgc ctccaccaag     360
ggcccatcgg tcttccccgc tagcgccctg tccaggagca cctccgagag cacagccgcc     420
ctgggctgcc tggtcaagga ctacttcccc gaaccggtga cggtgtcgtg gaactcaggc     480
gccctgacca gcggcgtgca caccttcccg gctgtcctac agtcctcagg actctactcc     540
ctcagcagcg tggtgaccgt gccctccagc agcttgggca cgaagaccta cacctgcaac     600
gtagatcaca agcccagcaa caccaaggtg gacaagagag ttgagtccaa atatggtccc     660
ccatgcccac cctgcccagc acctgaggcc gccggggac catcagtctt cctgttcccc      720
ccaaaaccca aggacactct catgatctcc cggacccctg aggtcacgtg cgtggtggtg     780
gacgtgagcc aggaagaccc cgaggtccag ttcaactggt acgtggatgg cgtggaggtg     840
cataatgcca agacaaagcc gcgggaggag cagttcaaca gcacgtaccg tgtggtcagc     900
gtcctcaccg tcctgcacca ggactggctg aacggcaagg agtacaagtg caaggtctcc     960
aacaaaggcc tcccgtcctc catcgagaaa accatctcca aagccaaagg gcagccccga    1020
gagccacagg tgtacaccct gcccccatcc caggaggaga tgaccaagaa ccaggtcagc    1080
ctgacctgcc tggtcaaagg cttctacccc agcgacatcg ccgtggagtg ggaaagcaat    1140
gggcagccgg agaacaacta caagaccacg cctcccgtgc tggactccga cggctccttc    1200
ttcctctaca gcaggctaac cgtggacaag agcaggtggc aggagggaa tgtcttctca     1260
tgctccgtga tgcatgaggc tctgcacaac cactacacac agaagagcct ctccctgtct    1320
ctgggtggcg gaggctccgg gggaggggt agcggaggag ggggatccca ggttcagctg     1380
gtgcagtctg gagctgaggt gaagaagcct ggggcctcag tgaaggtctc ctgcaaggct    1440
tctggttact cattcactga ctacaacatg gtgtgggtgc gacaggcccc tggacaatgc    1500
cttgagtgga tgggatatat tgatccttac aatggtggta ctggctacaa ccagaagttc    1560
gagggcagag tcaccatgac cacagacaca tccacgagca gcctacat ggagctgagg     1620
agcctgagat ctgacgacac ggccgtgtat tactgtgcga gaacgaggga tagatacgac    1680
gtctggtact cgatgtctg gggccaggga accctggtca ccgtctcctc aggaggcgga    1740
ggttccgggg aggggggcag cggaggaggc ggatcgggcg gaggaggaag tggaggcgga    1800
ggcagcgaca tccagatgac ccagtctcca tcttccgtgt ctgcatctgt tggcgacaga    1860
gtcaccatca cttgtaaggc cagtcaggat gtgtatattg ctgtagcctg gtatcagcag    1920
aaaccaggga aagcccctaa gctcctgatc tattgggcat ccacccggga cactgggtc     1980
ccatcaaggt tcagcggcag tggatctggg acagatttca ctctcaccat cagcagcctg    2040
cagcctgaag attttgcaac ttactattgt caccaatata gcagctatcc tcctacgttc    2100
ggctgcggga ccaaggtgga gatcaaa                                        2127
```

<210> SEQ ID NO 30
<211> LENGTH: 642
<212> TYPE: DNA
<213> ORGANISM: Artificial Sequence
<220> FEATURE:
<223> OTHER INFORMATION: Synthetic Construct

<400> SEQUENCE: 30

```
gacatccaga tgacccagtc tccatcttct gtgtctgcat ctgtaggaga cagagtcacc    60
atcacttgtc gggcgagtca gggtattgac aactggttaa cgtggtatca gcagaaacca   120
gggaaagccc ctaagctcct gatcgtcgag gcatccagtt tgcaatcagg ggtcccatca   180
aggttcagcg gcagtggatc tgggacagat ttcactctca ctatcagcag cctgcagcct   240
gaagattttg caacttacta ttgtcaacag gctaaggctt ttcctcccac tttcggcgga   300
gggaccaagg tggacatcaa acgaactgtg gctgcaccat ctgtcttcat cttcccgcca   360
tctgatgagc agttgaaatc tggaactgcc tctgttgtgt gcctgctgaa taacttctat   420
cccagagagg ccaaagtaca gtggaaggtg gataacgccc tccaatcggg taactcccag   480
gagagtgtca cagagcagga cagcaaggac agcacctaca gcctcagcag cacccctgacg   540
ctgagcaaag cagactacga gaaacacaaa gtctacgcct gcgaagtcac ccatcagggc   600
ctgagctcgc ccgtcacaaa gagcttcaac aggggagagt gc   642
```

<210> SEQ ID NO 31
<211> LENGTH: 2112
<212> TYPE: DNA
<213> ORGANISM: Artificial Sequence
<220> FEATURE:
<223> OTHER INFORMATION: Synthetic Construct

<400> SEQUENCE: 31

```
gaggtccagc tggtgcagtc tgggggaggc ctggtcaagc ctggggggtc cctgagactc    60
tcctgtgcag cctctggatt caccttcagt agctatagca tgctttgggt ccgccaggct   120
ccagggaagg ggctggagtg ggtctcagcc attagtagta gtagtagtta catatactac   180
gcagactcag tgaagggccg attcaccatc tccagagaca acgccaagaa ctcactgtat   240
ctgcaaatga acagcctgag agccgaggac acggctgtgt attactgtgc gagagtcaca   300
gatgcttttg atatctgggg ccaagggaca ctggtcaccg tctcagcgc ctccaccaag   360
ggcccatcgg tcttccccgct agcgccctgc tccaggagca cctccgagag cacagccgcc   420
ctgggctgcc tggtcaagga ctacttcccc gaaccggtga cggtgtcgtg gaactcaggc   480
gccctgacca gcggcgtgca caccttcccg gctgtcctac agtcctcagg actctactcc   540
ctcagcagcg tggtgaccgt gccctccagc agcttgggca cgaagaccta cacctgcaac   600
gtagatcaca agcccagcaa caccaaggtg gacaagagag ttgagtccaa atatggtccc   660
ccatgcccac cctgcccagc acctgaggcc gccgggggac catcagtctt cctgttcccc   720
ccaaaaccca aggacactct catgatctcc cggacccctg aggtcacgtg cgtggtggtg   780
gacgtgagcc aggaagaccc cgaggtccag ttcaactggt acgtggatgg cgtggaggtg   840
cataatgcca agacaaagcc gcgggaggag cagttcaaca gcacgtaccg tgtggtcagc   900
gtcctcaccg tcctgcacca ggactggctg aacggcaagg agtacaagtg caaggtctcc   960
aacaaaggcc tcccgtcctc catcgagaaa accatctcca aagccaaagg gcagccccga  1020
gagccacagg tgtacaccct gcccccatcc caggaggaga tgaccaagaa ccaggtcagc  1080
ctgacctgcc tggtcaaagg cttctacccc agcgacatcg ccgtggagtg ggaaagcaat  1140
```

```
gggcagccgg agaacaacta caagaccacg cctcccgtgc tggactccga cggctccttc    1200
ttcctctaca gcaggctaac cgtggacaag agcaggtggc aggaggggaa tgtcttctca    1260
tgctccgtga tgcatgaggc tctgcacaac cactacacac agaagagcct ctccctgtct    1320
ctgggtggcg gaggctccgg gggaggggt agcggaggag ggggatccga catcgtgatg    1380
acccagtctc cagactccct ggctgtgtct ctgggcgaga gggccaccat caactgcaag    1440
gccagtcagg atgtgtatat tgctgtagcc tggtaccagc agaaaccagg acagcctcct    1500
aagctgctca tttactgggc atccacccgg gacactgggg tccctgaccg attcagtggc    1560
agcgggtctg ggacagattt cactctcacc atcagcagcc tgcaggctga agatgtggca    1620
gtttattact gtcaccaata tagcagctat cctcctacgt tcggctgcgg gaccaaggtg    1680
gagatcaaag gtggcggagg atctggtgga ggtggctcag gaggtggcgg aagcggcgga    1740
ggtggaagtc aggtgcagct ggtgcagtct ggggctgagg tgaagaagcc tgggtcctcg    1800
gtgaaggtct cctgcaaggc ttctggttac tcattcactg actacaacat ggtgtgggtg    1860
cgacaggccc ctggacaatg ccttgagtgg atgggatata ttgatcctta caatggtggt    1920
actggctaca accagaagtt cgagggcaga gtcacgatta ccgcggacga atccacgagc    1980
acagcctaca tggagctgag cagcctgaga tctgaggaca cggccgtgta ttactgtgcg    2040
agaacgaggg ataggtacga cgtctggtac ttcgatgtct ggggccaggg aaccctggtc    2100
accgtctcct ca                                                        2112
```

<210> SEQ ID NO 32
<211> LENGTH: 745
<212> TYPE: PRT
<213> ORGANISM: Homo sapiens

<400> SEQUENCE: 32

```
Ala Ser Val Gly Leu Pro Ser Val Ser Leu Asp Leu Pro Arg Leu Ser
1               5                   10                  15

Ile Gln Lys Asp Ile Leu Thr Ile Lys Ala Asn Thr Thr Leu Gln Ile
            20                  25                  30

Thr Cys Arg Gly Gln Arg Asp Leu Asp Trp Leu Trp Pro Asn Asn Gln
        35                  40                  45

Ser Gly Ser Glu Gln Arg Val Glu Val Thr Glu Cys Ser Asp Gly Leu
    50                  55                  60

Phe Cys Lys Thr Leu Thr Ile Pro Lys Val Ile Gly Asn Asp Thr Gly
65                  70                  75                  80

Ala Tyr Lys Cys Phe Tyr Arg Glu Thr Asp Leu Ala Ser Val Ile Tyr
                85                  90                  95

Val Tyr Val Gln Asp Tyr Arg Ser Pro Phe Ile Ala Ser Val Ser Asp
            100                 105                 110

Gln His Gly Val Val Tyr Ile Thr Glu Asn Lys Asn Lys Thr Val Val
        115                 120                 125

Ile Pro Cys Leu Gly Ser Ile Ser Asn Leu Asn Val Ser Leu Cys Ala
    130                 135                 140

Arg Tyr Pro Glu Lys Arg Phe Val Pro Asp Gly Asn Arg Ile Ser Trp
145                 150                 155                 160

Asp Ser Lys Lys Gly Phe Thr Ile Pro Ser Tyr Met Ile Ser Tyr Ala
                165                 170                 175

Gly Met Val Phe Cys Glu Ala Lys Ile Asn Asp Glu Ser Tyr Gln Ser
            180                 185                 190
```

-continued

```
Ile Met Tyr Ile Val Val Val Gly Tyr Arg Ile Tyr Asp Val Val
        195                 200                 205

Leu Ser Pro Ser His Gly Ile Glu Leu Ser Val Gly Glu Lys Leu Val
    210                 215                 220

Leu Asn Cys Thr Ala Arg Thr Glu Leu Asn Val Gly Ile Asp Phe Asn
225                 230                 235                 240

Trp Glu Tyr Pro Ser Ser Lys His Gln His Lys Lys Leu Val Asn Arg
                    245                 250                 255

Asp Leu Lys Thr Gln Ser Gly Ser Glu Met Lys Lys Phe Leu Ser Thr
                260                 265                 270

Leu Thr Ile Asp Gly Val Thr Arg Ser Asp Gln Gly Leu Tyr Thr Cys
            275                 280                 285

Ala Ala Ser Ser Gly Leu Met Thr Lys Lys Asn Ser Thr Phe Val Arg
        290                 295                 300

Val His Glu Lys Pro Phe Val Ala Phe Gly Ser Gly Met Glu Ser Leu
305                 310                 315                 320

Val Glu Ala Thr Val Gly Glu Arg Val Arg Ile Pro Ala Lys Tyr Leu
                    325                 330                 335

Gly Tyr Pro Pro Pro Glu Ile Lys Trp Tyr Lys Asn Gly Ile Pro Leu
                340                 345                 350

Glu Ser Asn His Thr Ile Lys Ala Gly His Val Leu Thr Ile Met Glu
            355                 360                 365

Val Ser Glu Arg Asp Thr Gly Asn Tyr Thr Val Ile Leu Thr Asn Pro
        370                 375                 380

Ile Ser Lys Glu Lys Gln Ser His Val Val Ser Leu Val Val Tyr Val
385                 390                 395                 400

Pro Pro Gln Ile Gly Glu Lys Ser Leu Ile Ser Pro Val Asp Ser Tyr
                    405                 410                 415

Gln Tyr Gly Thr Thr Gln Thr Leu Thr Cys Thr Val Tyr Ala Ile Pro
                420                 425                 430

Pro Pro His His Ile His Trp Tyr Trp Gln Leu Glu Glu Glu Cys Ala
            435                 440                 445

Asn Glu Pro Ser Gln Ala Val Ser Val Thr Asn Pro Tyr Pro Cys Glu
        450                 455                 460

Glu Trp Arg Ser Val Glu Asp Phe Gln Gly Gly Asn Lys Ile Glu Val
465                 470                 475                 480

Asn Lys Asn Gln Phe Ala Leu Ile Glu Gly Lys Asn Lys Thr Val Ser
                    485                 490                 495

Thr Leu Val Ile Gln Ala Ala Asn Val Ser Ala Leu Tyr Lys Cys Glu
                500                 505                 510

Ala Val Asn Lys Val Gly Arg Gly Glu Arg Val Ile Ser Phe His Val
            515                 520                 525

Thr Arg Gly Pro Glu Ile Thr Leu Gln Pro Asp Met Gln Pro Thr Glu
        530                 535                 540

Gln Glu Ser Val Ser Leu Trp Cys Thr Ala Asp Arg Ser Thr Phe Glu
545                 550                 555                 560

Asn Leu Thr Trp Tyr Lys Leu Gly Pro Gln Pro Leu Pro Ile His Val
                    565                 570                 575

Gly Glu Leu Pro Thr Pro Val Cys Lys Asn Leu Asp Thr Leu Trp Lys
                580                 585                 590

Leu Asn Ala Thr Met Phe Ser Asn Ser Thr Asn Asp Ile Leu Ile Met
            595                 600                 605

Glu Leu Lys Asn Ala Ser Leu Gln Asp Gln Gly Asp Tyr Val Cys Leu
```

```
                  610                 615                 620
Ala Gln Asp Arg Lys Thr Lys Arg His Cys Val Arg Gln Leu
625                 630                 635                 640

Thr Val Leu Glu Arg Val Ala Pro Thr Ile Thr Gly Asn Leu Glu Asn
                    645                 650                 655

Gln Thr Thr Ser Ile Gly Glu Ser Ile Glu Val Ser Cys Thr Ala Ser
                660                 665                 670

Gly Asn Pro Pro Pro Gln Ile Met Trp Phe Lys Asp Asn Glu Thr Leu
                675                 680                 685

Val Glu Asp Ser Gly Ile Val Leu Lys Asp Gly Asn Arg Asn Leu Thr
                690                 695                 700

Ile Arg Arg Val Arg Lys Glu Asp Glu Gly Leu Tyr Thr Cys Gln Ala
705                 710                 715                 720

Cys Ser Val Leu Gly Cys Ala Lys Val Glu Ala Phe Phe Ile Ile Glu
                    725                 730                 735

Gly Ala Gln Glu Lys Thr Asn Leu Glu
                740                 745

<210> SEQ ID NO 33
<211> LENGTH: 478
<212> TYPE: PRT
<213> ORGANISM: Homo sapiens

<400> SEQUENCE: 33

Tyr Asn Asn Phe Arg Lys Ser Met Asp Ser Ile Gly Lys Lys Gln Tyr
1               5                   10                  15

Gln Val Gln His Gly Ser Cys Ser Tyr Thr Phe Leu Leu Pro Glu Met
                20                  25                  30

Asp Asn Cys Arg Ser Ser Ser Pro Tyr Val Ser Asn Ala Val Gln
                35                  40                  45

Arg Asp Ala Pro Leu Glu Tyr Asp Asp Ser Val Gln Arg Leu Gln Val
            50                  55                  60

Leu Glu Asn Ile Met Glu Asn Asn Thr Gln Trp Leu Met Lys Leu Glu
65                  70                  75                  80

Asn Tyr Ile Gln Asp Asn Met Lys Lys Glu Met Val Glu Ile Gln Gln
                85                  90                  95

Asn Ala Val Gln Asn Gln Thr Ala Val Met Ile Glu Ile Gly Thr Asn
                100                 105                 110

Leu Leu Asn Gln Thr Ala Glu Gln Thr Arg Lys Leu Thr Asp Val Glu
            115                 120                 125

Ala Gln Val Leu Asn Gln Thr Thr Arg Leu Glu Leu Gln Leu Leu Glu
            130                 135                 140

His Ser Leu Ser Thr Asn Lys Leu Glu Lys Gln Ile Leu Asp Gln Thr
145                 150                 155                 160

Ser Glu Ile Asn Lys Leu Gln Asp Lys Asn Ser Phe Leu Glu Lys Lys
                165                 170                 175

Val Leu Ala Met Glu Asp Lys His Ile Ile Gln Leu Gln Ser Ile Lys
                180                 185                 190

Glu Glu Lys Asp Gln Leu Gln Val Leu Val Ser Lys Gln Asn Ser Ile
            195                 200                 205

Ile Glu Glu Leu Glu Lys Lys Ile Val Thr Ala Thr Val Asn Asn Ser
            210                 215                 220

Val Leu Gln Lys Gln Gln His Asp Leu Met Glu Thr Val Asn Asn Leu
225                 230                 235                 240
```

```
Leu Thr Met Met Ser Thr Ser Asn Ser Ala Lys Asp Pro Thr Val Ala
                245                 250                 255

Lys Glu Glu Gln Ile Ser Phe Arg Asp Cys Ala Glu Val Phe Lys Ser
            260                 265                 270

Gly His Thr Thr Asn Gly Ile Tyr Thr Leu Thr Phe Pro Asn Ser Thr
        275                 280                 285

Glu Glu Ile Lys Ala Tyr Cys Asp Met Glu Ala Gly Gly Gly Gly Trp
    290                 295                 300

Thr Ile Ile Gln Arg Arg Glu Asp Gly Ser Val Asp Phe Gln Arg Thr
305                 310                 315                 320

Trp Lys Glu Tyr Lys Val Gly Phe Gly Asn Pro Ser Gly Glu Tyr Trp
                325                 330                 335

Leu Gly Asn Glu Phe Val Ser Gln Leu Thr Asn Gln Gln Arg Tyr Val
            340                 345                 350

Leu Lys Ile His Leu Lys Asp Trp Glu Gly Asn Glu Ala Tyr Ser Leu
        355                 360                 365

Tyr Glu His Phe Tyr Leu Ser Ser Glu Glu Leu Asn Tyr Arg Ile His
    370                 375                 380

Leu Lys Gly Leu Thr Gly Thr Ala Gly Lys Ile Ser Ser Ile Ser Gln
385                 390                 395                 400

Pro Gly Asn Asp Phe Ser Thr Lys Asp Gly Asp Asn Asp Lys Cys Ile
                405                 410                 415

Cys Lys Cys Ser Gln Met Leu Thr Gly Gly Trp Trp Phe Asp Ala Cys
            420                 425                 430

Gly Pro Ser Asn Leu Asn Gly Met Tyr Tyr Pro Gln Arg Gln Asn Thr
        435                 440                 445

Asn Lys Phe Asn Gly Ile Lys Trp Tyr Tyr Trp Lys Gly Ser Gly Tyr
    450                 455                 460

Ser Leu Lys Ala Thr Thr Met Met Ile Arg Pro Ala Asp Phe
465                 470                 475

<210> SEQ ID NO 34
<211> LENGTH: 10
<212> TYPE: PRT
<213> ORGANISM: Artificial Sequence
<220> FEATURE:
<223> OTHER INFORMATION: Synthetic Construct

<400> SEQUENCE: 34

Gly Gly Gly Gly Ser Gly Gly Gly Gly Ser
1               5                   10

<210> SEQ ID NO 35
<211> LENGTH: 15
<212> TYPE: PRT
<213> ORGANISM: Artificial Sequence
<220> FEATURE:
<223> OTHER INFORMATION: Synthetic Construct

<400> SEQUENCE: 35

Gly Gly Gly Gly Ser Gly Gly Gly Gly Ser Gly Gly Gly Gly Ser
1               5                   10                  15

<210> SEQ ID NO 36
<211> LENGTH: 20
<212> TYPE: PRT
<213> ORGANISM: Artificial Sequence
<220> FEATURE:
<223> OTHER INFORMATION: Synthetic Construct
```

-continued

```
<400> SEQUENCE: 36

Gly Gly Gly Gly Ser Gly Gly Gly Ser Gly Gly Gly Ser Gly
1               5                   10                  15

Gly Gly Gly Ser
            20

<210> SEQ ID NO 37
<211> LENGTH: 25
<212> TYPE: PRT
<213> ORGANISM: Artificial Sequence
<220> FEATURE:
<223> OTHER INFORMATION: Synthetic Construct

<400> SEQUENCE: 37

Gly Gly Gly Gly Ser Gly Gly Gly Ser Gly Gly Gly Ser Gly
1               5                   10                  15

Gly Gly Gly Ser Gly Gly Gly Gly Ser
            20                  25

<210> SEQ ID NO 38
<211> LENGTH: 712
<212> TYPE: PRT
<213> ORGANISM: Artificial Sequence
<220> FEATURE:
<223> OTHER INFORMATION: Synthetic Construct

<400> SEQUENCE: 38

Glu Val Gln Leu Val Gln Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Val Thr Asp Ala Phe Asp Ile Trp Gly Gln Gly Thr Met Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Arg Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240
```

-continued

```
Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Gly Gly Gly
        435                 440                 445

Ser Gly Gly Gly Gly Ser Gly Gly Gly Gly Ser Gln Val Gln Leu Val
    450                 455                 460

Gln Ser Gly Ala Glu Val Lys Lys Pro Gly Ala Ser Val Lys Val Ser
465                 470                 475                 480

Cys Lys Ala Ser Gly Tyr Ser Phe Thr Asp Tyr Asn Met Val Trp Val
                485                 490                 495

Arg Gln Ala Pro Gly Gln Cys Leu Glu Trp Met Gly Tyr Ile Asp Pro
            500                 505                 510

Tyr Asn Gly Gly Thr Gly Tyr Asn Gln Lys Phe Glu Gly Arg Val Thr
        515                 520                 525

Met Thr Thr Asp Thr Ser Thr Ala Tyr Met Glu Leu Arg Ser
    530                 535                 540

Leu Arg Ser Asp Asp Thr Ala Val Tyr Tyr Cys Ala Arg Thr Arg Asp
545                 550                 555                 560

Arg Tyr Asp Val Trp Tyr Phe Asp Val Trp Gly Gln Gly Thr Leu Val
                565                 570                 575

Thr Val Ser Ser Gly Gly Gly Ser Gly Gly Gly Gly Ser Gly Gly
            580                 585                 590

Gly Gly Ser Gly Gly Gly Gly Ser Gly Gly Gly Gly Ser Asp Ile Gln
        595                 600                 605

Met Thr Gln Ser Pro Ser Ser Val Ser Ala Ser Val Gly Asp Arg Val
    610                 615                 620

Thr Ile Thr Cys Lys Ala Ser Gln Asp Val Tyr Ile Ala Val Ala Trp
625                 630                 635                 640

Tyr Gln Gln Lys Pro Gly Lys Ala Pro Lys Leu Leu Ile Tyr Trp Ala
                645                 650                 655

Ser Thr Arg Asp Thr Gly Val Pro Ser Arg Phe Ser Gly Ser Gly Ser
```

```
                    660                 665                 670
Gly Thr Asp Phe Thr Leu Thr Ile Ser Ser Leu Gln Pro Glu Asp Phe
                675                 680                 685

Ala Thr Tyr Tyr Cys His Gln Tyr Ser Ser Tyr Pro Pro Thr Phe Gly
            690                 695                 700

Cys Gly Thr Lys Val Glu Ile Lys
705                 710

<210> SEQ ID NO 39
<211> LENGTH: 214
<212> TYPE: PRT
<213> ORGANISM: Artificial Sequence
<220> FEATURE:
<223> OTHER INFORMATION: Synthetic Construct

<400> SEQUENCE: 39

Asp Ile Gln Met Thr Gln Ser Pro Ser Ser Val Ser Ala Ser Ile Gly
1               5                   10                  15

Asp Arg Val Thr Ile Thr Cys Arg Ala Ser Gln Gly Ile Asp Asn Trp
            20                  25                  30

Leu Gly Trp Tyr Gln Gln Lys Pro Gly Lys Ala Pro Lys Leu Leu Ile
        35                  40                  45

Tyr Asp Ala Ser Asn Leu Asp Thr Gly Val Pro Ser Arg Phe Ser Gly
    50                  55                  60

Ser Gly Ser Gly Thr Tyr Phe Thr Leu Thr Ile Ser Ser Leu Gln Ala
65                  70                  75                  80

Glu Asp Phe Ala Val Tyr Phe Cys Gln Gln Ala Lys Ala Phe Pro Pro
                85                  90                  95

Thr Phe Gly Gly Gly Thr Lys Val Asp Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 40
<211> LENGTH: 709
<212> TYPE: PRT
<213> ORGANISM: Artificial Sequence
<220> FEATURE:
<223> OTHER INFORMATION: Synthetic Construct

<400> SEQUENCE: 40

Glu Val Gln Leu Val Gln Ser Gly Gly Gly Leu Val Lys Pro Gly Gly
1               5                   10                  15

Ser Leu Arg Leu Ser Cys Ala Ser Gly Phe Thr Phe Ser Ser Tyr
            20                  25                  30
```

Ser Met Asn Trp Val Arg Gln Ala Pro Gly Lys Gly Leu Glu Trp Val
         35                  40                  45

Ser Ser Ile Ser Ser Ser Ser Tyr Ile Tyr Tyr Ala Asp Ser Val
     50                  55                  60

Lys Gly Arg Phe Thr Ile Ser Arg Asp Asn Ala Lys Asn Ser Leu Tyr
65                   70                  75                  80

Leu Gln Met Asn Ser Leu Arg Ala Glu Asp Thr Ala Val Tyr Tyr Cys
                 85                  90                  95

Ala Arg Val Thr Asp Ala Phe Asp Ile Trp Gly Gln Gly Thr Met Val
             100                 105                 110

Thr Val Ser Ser Ala Ser Thr Lys Gly Pro Ser Val Phe Pro Leu Ala
             115                 120                 125

Pro Cys Ser Arg Ser Thr Ser Glu Ser Thr Ala Ala Leu Gly Cys Leu
         130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                 165                 170                 175

Gly Leu Tyr Ser Leu Ser Ser Val Val Thr Val Pro Ser Ser Ser Leu
             180                 185                 190

Gly Thr Lys Thr Tyr Thr Cys Asn Val Asp His Lys Pro Ser Asn Thr
         195                 200                 205

Lys Val Asp Lys Arg Val Glu Ser Lys Tyr Gly Pro Pro Cys Pro Pro
    210                 215                 220

Cys Pro Ala Pro Glu Ala Ala Gly Gly Pro Ser Val Phe Leu Phe Pro
225                 230                 235                 240

Pro Lys Pro Lys Asp Thr Leu Met Ile Ser Arg Thr Pro Glu Val Thr
                 245                 250                 255

Cys Val Val Val Asp Val Ser Gln Glu Asp Pro Glu Val Gln Phe Asn
             260                 265                 270

Trp Tyr Val Asp Gly Val Glu Val His Asn Ala Lys Thr Lys Pro Arg
         275                 280                 285

Glu Glu Gln Phe Asn Ser Thr Tyr Arg Val Val Ser Val Leu Thr Val
    290                 295                 300

Leu His Gln Asp Trp Leu Asn Gly Lys Glu Tyr Lys Cys Lys Val Ser
305                 310                 315                 320

Asn Lys Gly Leu Pro Ser Ser Ile Glu Lys Thr Ile Ser Lys Ala Lys
                 325                 330                 335

Gly Gln Pro Arg Glu Pro Gln Val Tyr Thr Leu Pro Pro Ser Gln Glu
             340                 345                 350

Glu Met Thr Lys Asn Gln Val Ser Leu Thr Cys Leu Val Lys Gly Phe
         355                 360                 365

Tyr Pro Ser Asp Ile Ala Val Glu Trp Glu Ser Asn Gly Gln Pro Glu
    370                 375                 380

Asn Asn Tyr Lys Thr Thr Pro Pro Val Leu Asp Ser Asp Gly Ser Phe
385                 390                 395                 400

Phe Leu Tyr Ser Arg Leu Thr Val Asp Lys Ser Arg Trp Gln Glu Gly
                 405                 410                 415

Asn Val Phe Ser Cys Ser Val Met His Glu Ala Leu His Asn His Tyr
             420                 425                 430

Thr Gln Lys Ser Leu Ser Leu Ser Leu Gly Gly Gly Gly Ser Gly Gly
         435                 440                 445

Gly Gly Ser Gly Gly Gly Gly Ser Gln Val Gln Leu Val Gln Ser Gly

```
                450             455             460
Ala Glu Val Lys Lys Pro Gly Ala Ser Val Lys Val Ser Cys Lys Ala
465                 470                 475                 480

Ser Gly Tyr Ser Phe Thr Asp Tyr Asn Met Val Trp Val Arg Gln Ala
                485                 490                 495

Pro Gly Gln Cys Leu Glu Trp Met Gly Tyr Ile Asp Pro Tyr Asn Gly
                500                 505                 510

Gly Thr Gly Tyr Asn Gln Lys Phe Glu Gly Arg Val Thr Met Thr Thr
                515                 520                 525

Asp Thr Ser Thr Ser Thr Ala Tyr Met Glu Leu Arg Ser Leu Arg Ser
                530                 535                 540

Asp Asp Thr Ala Val Tyr Tyr Cys Ala Arg Thr Arg Asp Arg Tyr Asp
545                 550                 555                 560

Val Trp Tyr Phe Asp Val Trp Gly Gln Gly Thr Leu Val Thr Val Ser
                565                 570                 575

Ser Gly Gly Gly Gly Ser Gly Gly Gly Gly Ser Gly Gly Gly Gly Ser
                580                 585                 590

Gly Gly Gly Gly Ser Gly Gly Gly Gly Ser Asp Ile Gln Met Thr Gln
                595                 600                 605

Ser Pro Ser Ser Val Ser Ala Ser Val Gly Asp Arg Val Thr Ile Thr
                610                 615                 620

Cys Lys Ala Ser Gln Asp Val Tyr Ile Ala Val Ala Trp Tyr Gln Gln
625                 630                 635                 640

Lys Pro Gly Lys Ala Pro Lys Leu Leu Ile Tyr Trp Ala Ser Thr Arg
                645                 650                 655

Asp Thr Gly Val Pro Ser Arg Phe Ser Gly Ser Gly Ser Gly Thr Asp
                660                 665                 670

Phe Thr Leu Thr Ile Ser Ser Leu Gln Pro Glu Asp Phe Ala Thr Tyr
                675                 680                 685

Tyr Cys His Gln Tyr Ser Ser Tyr Pro Pro Thr Phe Gly Cys Gly Thr
                690                 695                 700

Lys Val Glu Ile Lys
705
```